US010227349B2

(12) United States Patent
Clark et al.

(10) Patent No.: US 10,227,349 B2
(45) Date of Patent: Mar. 12, 2019

(54) PYRAZOLO[1,5-A]PYRIMIDINE COMPOUND

(71) Applicant: Eisai R&D Management Co., Ltd., Bunkyo-ku, Tokyo (JP)

(72) Inventors: Richard Clark, Tsuchiura (JP); Tetsuya Kawahara, Ami-machi (JP); Daisuke Iida, Tsukuba (JP); Shinsuke Hirota, Tsukuba (JP); Yasuaki Kamada, Tokyo (JP); Toshiyuki Ohfusa, Nagareyama (JP); Naoki Yoneda, Tsukuba (JP); Fumiyoshi Matsuura, Tsukuba (JP); So Yasui, Tsukubamirai (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/689,481

(22) Filed: Aug. 29, 2017

(65) Prior Publication Data

US 2018/0057499 A1    Mar. 1, 2018

(30) Foreign Application Priority Data

Aug. 31, 2016 (JP) ................. 2016-169507

(51) Int. Cl.
| | | |
|---|---|---|
| *C07D 487/04* | (2006.01) | |
| *A61K 31/519* | (2006.01) | |
| *A61P 17/06* | (2006.01) | |
| *A61P 29/00* | (2006.01) | |

(52) U.S. Cl.
CPC .......... *C07D 487/04* (2013.01); *A61K 31/519* (2013.01); *A61P 17/06* (2018.01); *A61P 29/00* (2018.01)

(58) Field of Classification Search
None
See application file for complete search history.

(56) References Cited

FOREIGN PATENT DOCUMENTS

| JP | 2003-286171 | 10/2003 |
|---|---|---|
| JP | 2004-170323 | 6/2004 |
| JP | 2013-060438 | 4/2013 |
| JP | 2013-520399 | 6/2013 |
| WO | WO 2003/037900 | 5/2003 |
| WO | WO 2005/030773 | 4/2005 |
| WO | WO 2011/105628 | 9/2011 |
| WO | WO 2012/101453 | 8/2012 |
| WO | WO 2015/048245 | 4/2015 |

OTHER PUBLICATIONS

Afkhami-Goli et al., "Proteinase-Activated Receptor-2 Exerts Protective and Pathogenic Cell Type-Specific Effects in Alzheimer's Disease," The Journal of Immunology, 2007, 179(8): p. 5493-p. 5503.
Bohm et al., "Molecular cloning, expression and potential functions of the human proteinase-activated receptor-2," Biochem. J., 1996, 314: p. 1009-p. 1016.
Dale et al., "Protease Signaling to G Protein-Coupled Receptors: Implications for Inflammation and Pain," Journal of Receptors and Signal Transduction, 2008, 28: p. 29-p. 37.
D'Andrea et al., "Characterization of protease-activated receptor-2 immunoreactivity in normal human tissues," The Journal of Histochemistry & Cytochemistry, 1998, 46(2): p. 157-p. 164.
Dery et al., "Proteinase-activated receptors: novel mechanisms of signaling by serine proteases," The American Physiological Society (Cell Physiol.)., 1998, 274: p. C1429-p. C1452.
Hachem et al., "Serine Protease Signaling of Epidermal Permeability Barrier Homeostasis," Journal of Investigative Dermatology, 2006, 126(9): p. 2074-p. 2086.
International Search Report in International Patent Application PCT/JP2017/030865, dated Sep. 26, 2017, 2 pages.
Macfarlane et al., "Proteinase-Activated Receptors," Pharmacological Reviews, 2001, 53(2): p. 245- p. 282.
Rothmeier and Ruf, "Protease-activated receptor 2 signaling in inflammation," Semin Immunopathol, 2012, 34(1): p. 133-p. 149.
Seyfarth et al., "Dry skin, barrier function, and irritant contact dermatitis in the elderly," Clinics in Dermatology, 2011, 29(1): p. 31-p. 36.
Yamaguchi and Hearing, "Physiological factors that regulate skin pigmentation," J. Biofactors., 2009, 35(2): p. 193-p. 199.
Yau et al., "Toward Drugs for Protease-Activated Receptor 2 (PAR2)," Journal of Medicinal Chemistry, 2013, 56(19): p. 7477-p. 7497.

*Primary Examiner* — Susanna Moore

(74) *Attorney, Agent, or Firm* — Fish & Richardson P.C.

(57) ABSTRACT

The disclosure provides pyrazolo[1,5-a]pyrimidine compounds, and pharmaceutically acceptable salts thereof, having protease-activated receptor 2 (PAR2) inhibitory action, pharmaceutical compositions containing the same, and methods of treatment using the same.

16 Claims, No Drawings
Specification includes a Sequence Listing.

PYRAZOLO[1,5-A]PYRIMIDINE COMPOUND

CROSS-REFERENCE TO RELATED APPLICATION

This application claims the benefit of Japanese application No. 2016-169507 filed on Aug. 31, 2016, the disclosure of which is herein incorporated by reference in its entirety.

TECHNICAL FIELD

The present invention relates to a pyrazolo[1,5-a]pyrimidine compound having a PAR2 inhibitory action and a pharmaceutically acceptable salt thereof, and a pharmaceutical composition containing the same.

BACKGROUND

Protease-activated receptor (PAR) is a type of trimeric G protein-coupled seven-transmembrane receptors and belongs to the receptor family mediating the cell action of serine proteases, and four molecules, PAR1, PAR2, PAR3 and PAR4, have been cloned so far.

Serine proteases cleave an extracellular amino-terminal peptide chain of the PAR molecule at a specific site and thus expose a new amino-terminal peptide chain having a receptor activation sequence consisting of 5 or 6 amino acid residues. The newly exposed amino-terminal peptide chain cleaved by a serine protease bonds as a chain-like ligand to the extracellular loop 2, which is the active site of PAR2 itself and thus activates PAR2. PAR2 is known to be activated by trypsin, tryptase, kallikrein (mainly kallikreins 2, 4, 5, 6 and 14), blood coagulation factor VIIa, blood coagulation factor Xa, and the like, and also activated when a synthetic peptide consisting of 5 or 6 amino acids synthesized based on the receptor activation sequence enters exogenously (see Non Patent Literatures 1 to 3).

PAR2 herein is widely distributed in vivo such as blood vessel, prostate gland, small intestine, large intestine, liver, kidney, pancreas, stomach, lung, brain and skin, and known to be an aggravating factor in various diseases such as neurogenic inflammation, pain, itch, inflammation and allergy (see Patent Literatures 1 and 2, and Non Patent Literatures 4 to 6). For this reason, a PAR2 inhibitor is expected to be a possible treatment drug for these diseases and suggested to be, for example, a treatment drug for inflammatory bowel diseases, a treatment drug for dermatitis, a treatment drug for allergic diseases, or a preventive drug for skin pigmentation (see Patent Literatures 3 to 5 and Non Patent Literatures 3 and 6 to 11).

CITATION LIST

Patent Literature

[Patent Literature 1] JP-A-2003-286171
[Patent Literature 2] JP-A-2004-170323
[Patent Literature 3] WO 2012/101453
[Patent Literature 4] WO 2015/048245
[Patent Literature 5] WO 2005/030773

Non Patent Literature

[Non Patent Literature 1] Dery, O. et al. Am. J. Physiol (Cell Physiol.). 274, C1429-1452, 1998
[Non Patent Literature 2] Macfarlane, S. R. et al. Pharmacol. Rev. 53, 245-282, 2001
[Non Patent Literature 3] Yau, M. K. et al. Journal of Medicinal Chemistry, 56, 7477-7497, 2013
[Non Patent Literature 4] Bohm, S. K. et al. Biochem. J. 15; 314, 1009-1016, 1996
[Non Patent Literature 5] D'Andrea, M. R. et al. J. Histochem. Cytochem. 46(2): 157-164, 1998
[Non Patent Literature 6] Rothmeier, A. S., Ruf, W. Semin. Immunopathol. 34(1): 133-149, 2012
[Non Patent Literature 7] Yamaguchi, Y., Hearing, V. J. Biofactors. 35(2): 193-199, 2009
[Non Patent Literature 8] Afkhami-Goli, A. et al. The Journal of Immunology. 179: 5493-5503, 2007
[Non Patent Literature 9] Dale, C. et al. Journal of Receptors and Signal Transduction. 28:29-37, 2008
[Non Patent Literature 10] Hachem, J. P. et al. Journal of Investigative Dermatology. 126: 2074-2086, 2006
[Non Patent Literature 11] Seyfarth, F. et al. Clinics in Dermatology. 29: 31-36, 2011

SUMMARY

An object of the present invention is to provide a pyrazolo[1,5-a]pyrimidine compound having a PAR2 inhibitory action and a pharmaceutically acceptable salt thereof, and a pharmaceutical composition containing the same.

The present inventors diligently conducted studies to achieve the above object and consequently found novel pyrazolo[1,5-a]pyrimidine compounds having the PAR2 inhibitory action.

More specifically, the present invention relates to the following [1] to [57].

[1] A compound selected from the group consisting of:
2-((3R*,4S*)-1-(7-((2,6-dimethylphenyl)(methyl)amino)-5-(3,4,5-trifluorophenyl)pyrazolo[1,5-a]pyrimidine-2-carbonyl)-3-fluoropiperidin-4-yl)acetic acid represented by chemical formula (I):

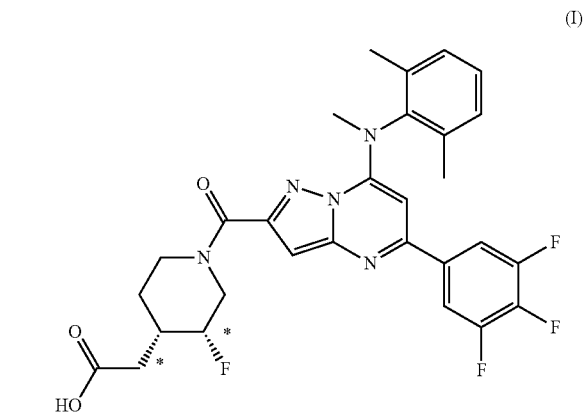 [SMILES: Cc1cccc(C)c1N(C)c1cc(-c2cc(F)c(F)c(F)c2)nc2cc(C(=O)N3CC[C@@H](CC(=O)O)[C@@H](F)C3)nn12]

2-((3R*,4S*)-1-(7-((2,6-dimethylphenyl)(methyl)amino)-5-(3,4,5-trifluorophenyl)pyrazolo[1,5-a]pyrimidine-2-carbonyl)-3-methoxypiperidin-4-yl)acetic acid represented by chemical formula (II):

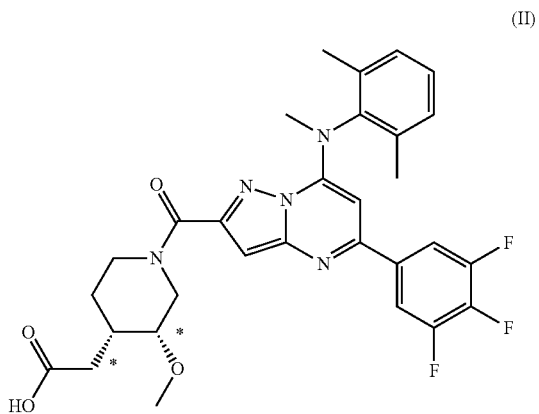 [SMILES: CO[C@H]1CN(C(=O)c2cc3nc(-c4cc(F)c(F)c(F)c4)cc(N(C)c4c(C)cccc4C)n3n2)CC[C@H]1CC(=O)O]

(II)

2-((3R*,4S*)-1-(5-(4,4-dimethylcyclohexyl)-7-((2,6-dimethylphenyl)(methyl)amino)pyrazolo[1,5-a]pyrimidine-2-carbonyl)-3-fluoropiperidin-4-yl) acetic acid represented by chemical formula (III):

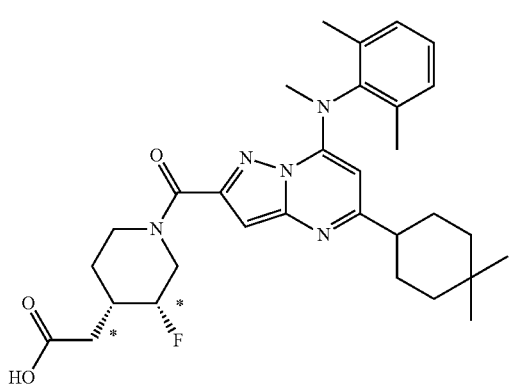

(III)

2-((3R*,4S*)-1-(5-(3-chloro-4-fluorophenyl)-7-((2,6-dimethylphenyl)(methyl)amino)pyrazolo[1,5-a]pyrimidine-2-carbonyl)-3-methoxypiperidin-4-yl)acetic acid represented by chemical formula (IV):

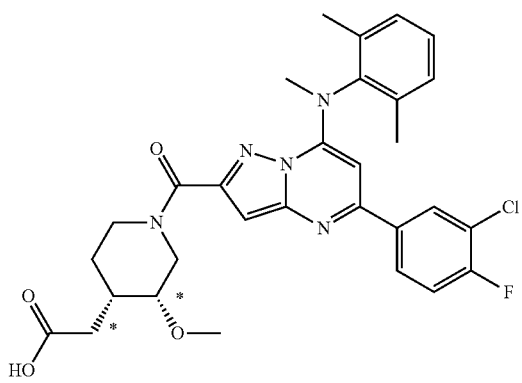

(IV)

2-((3R*,4S*)-3-fluoro-1-(7-((2-methoxy-6-methylphenyl)(methyl)amino)-5-(3,4,5-trifluorophenyl)pyrazolo[1,5-a]pyrimidine-2-carbonyl)piperidin-4-yl)acetic acid represented by chemical formula (V):

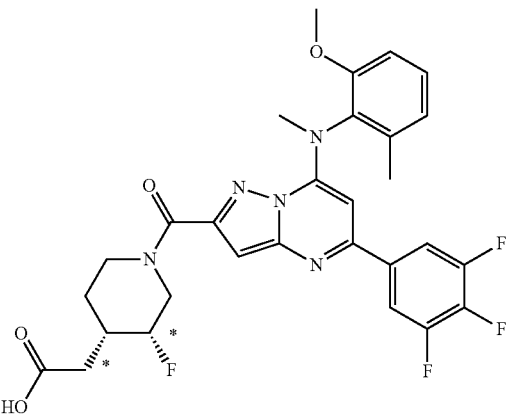

(V)

2-((3R*,4S*)-3-methoxy-1-(7-((2-methoxy-6-methylphenyl)(methyl)amino)-5-(3,4,5-trifluorophenyl)pyrazolo[1,5-a]pyrimidine-2-carbonyl)piperidin-4-yl) acetic acid represented by chemical formula (VI):

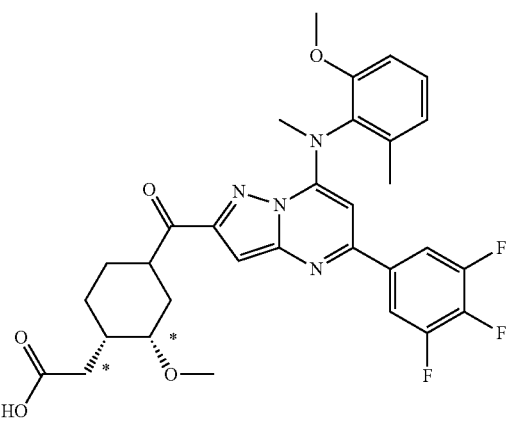

(VI)

(R)-3-(7-((2-fluoro-6-methoxyphenyl)(methyl)amino)-N-methyl-5-(3,4,5-trifluorophenyl)pyrazolo[1,5-a]pyrimidine-2-carboxamide)butanoic acid represented by chemical formula (VII):

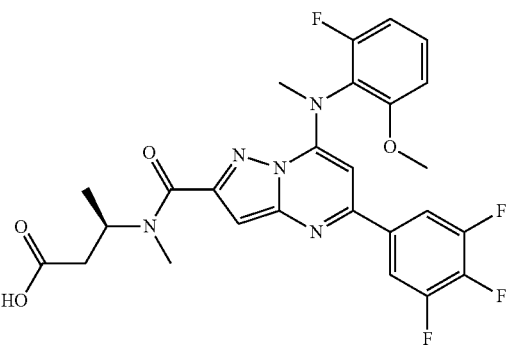

(VII)

2-((1α,5α,6α)-3-(5-(4-chloro-3,5-difluorophenyl)-7-(isobutyl((R)-3-methylbutan-2-yl)amino)pyrazolo[1,5-a]pyrimidine-2-carbonyl)-3-azabicyclo[3.1.0]hexan-6-yl)acetic acid represented by chemical formula (VIII)

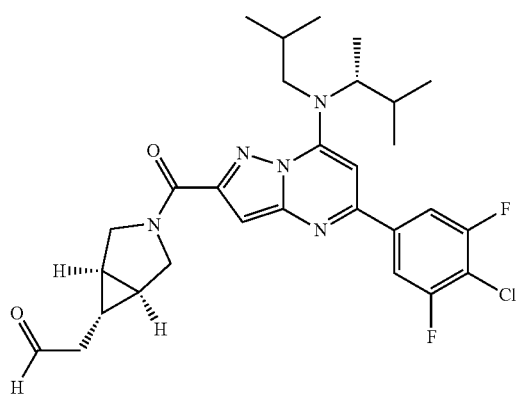

(R)-3-(7-(isobutyl((R)-3-methylbutan-2-yl)amino)-N-methyl-5-(3,4,5-trifluorophenyl)pyrazolo[1,5-a]pyrimidine-2-carboxamide)butanoic acid represented by chemical formula (IX):

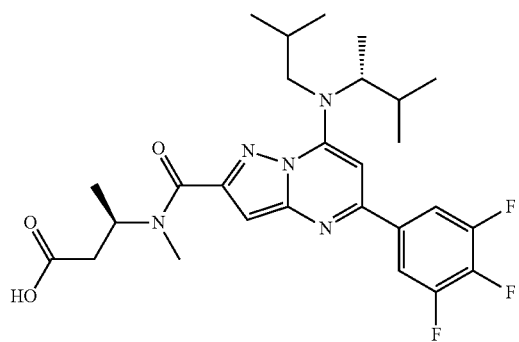

2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid represented by chemical formula (X):

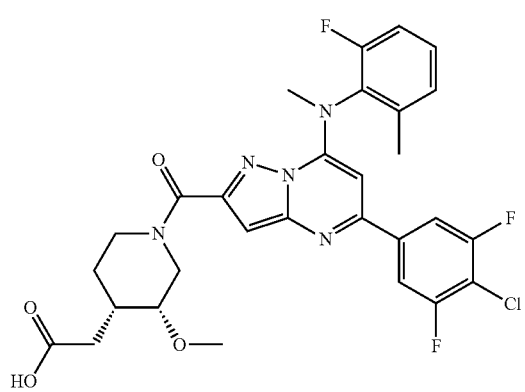

2-((3R*,4S*)-1-(5-(4-chloro-3-fluorophenyl)-7-((2-chloro-6-methylphenyl)(methyl)amino)pyrazolo[1,5-a]pyrimidine-2-carbonyl)-3-methoxypiperidin-4-yl)acetic acid represented by chemical formula (XI):

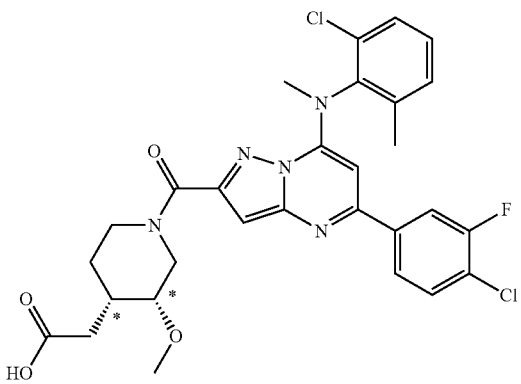

2-((3R*,4S*)-1-(5-(4-chloro-3,5-difluorophenyl)-7-((2-chloro-6-methylphenyl)(methyl)amino)pyrazolo[1,5-a]pyrimidine-2-carbonyl)-3-methoxypiperidin-4-yl)acetic acid represented by chemical formula (XII):

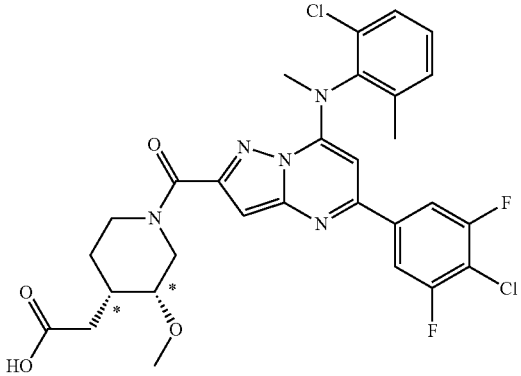

2-((3R*,4S*)-1-(7-((2-chloro-6-fluorophenyl)(methyl)amino)-5-(3,4,5-trifluorophenyl)pyrazolo[1,5-a]pyrimidine-2-carbonyl)-3-fluoropiperidin-4-yl)acetic acid represented by chemical formula (XIII):

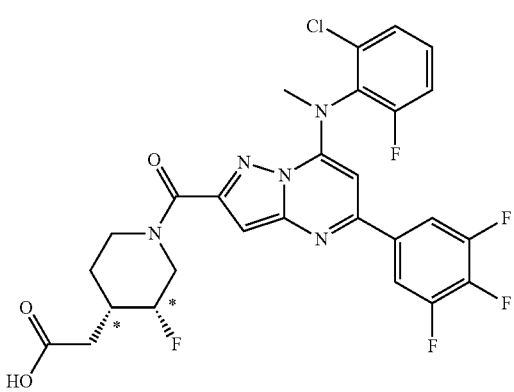

2-((3R*,4S*)-1-(5-(4-chloro-3,5-difluorophenyl)-7-((2-chlorophenyl)(methyl)amino)pyrazolo[1,5-a]pyrimidine-2-carbonyl)-3-fluoropiperidin-4-yl) acetic acid represented by chemical formula (XIV):

(XIV)

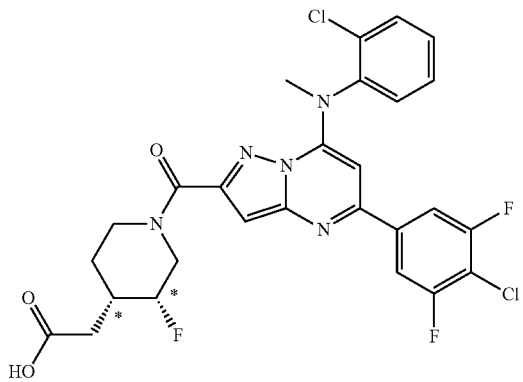

2-((1α,5α,6α)-3-(5-(4-chloro-3,5-difluorophenyl)-7-(isopropyl(propyl)amino)pyrazolo[1,5-a]pyrimidine-2-carbonyl)-3-azabicyclo[3.1.0]hexan-6-yl)acetic acid represented by chemical formula (XV):

(XV)

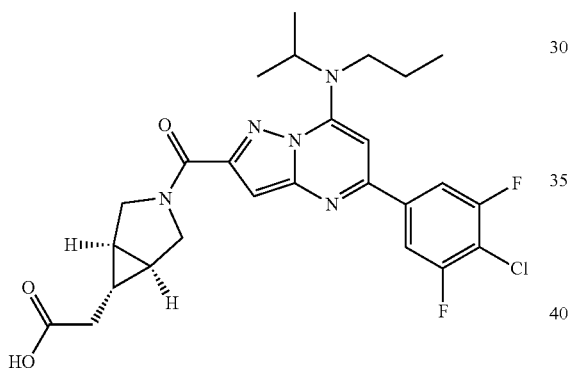

2-((1α,5α,6α)-3-(7-(isobutyl((S)-1-phenylethyl)amino)-5-(3,4,5-trifluorophenyl)pyrazolo[1,5-a]pyrimidine-2-carbonyl)-3-azabicyclo[3.1.0]hexan-6-yl)acetic acid represented by chemical formula (XVI):

(XVI)

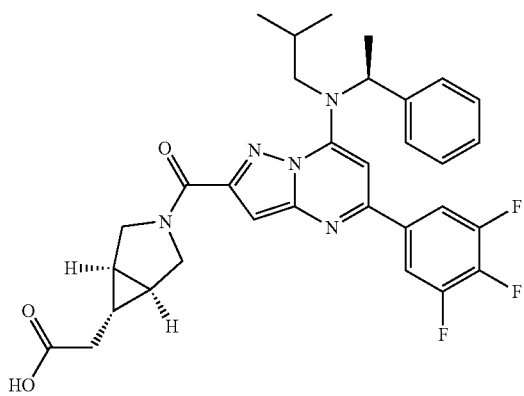

2-(1-(7-((2-chloro-6-fluorophenyl)methyl)amino)-5-(3,4,5-trifluorophenyl)pyrazolo[1,5-a]pyrimidine-2-carbonyl)piperidin-4-yl)acetic acid represented by chemical formula (XVII):

(XVII)

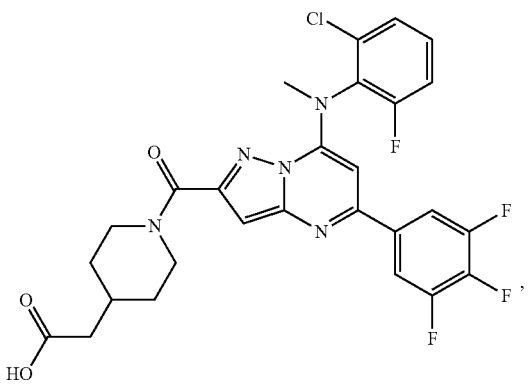

and 2-((3R*,4S*)-1-(5-(4-chloro-3,5-difluorophenyl)-7-(isopropyl(propyl)amino)pyrazolo[1,5-a]pyrimidine-2-carbonyl)-3-methylpiperidin-4-yl)acetic acid represented by chemical formula (XVIII):

(XVIII)

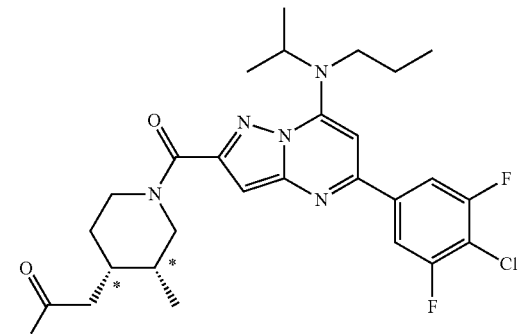

or a pharmaceutically acceptable salt thereof.

[2] 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid represented by chemical formula (X):

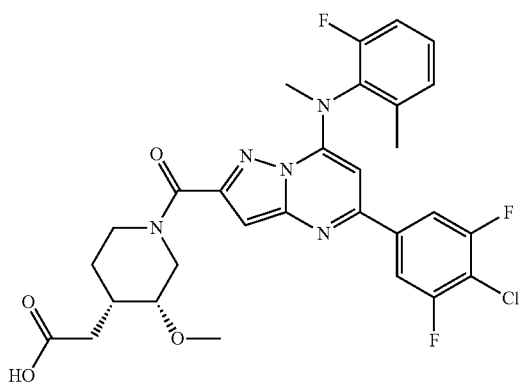

or a pharmaceutically acceptable salt thereof.

[3] 2-((3R*,4S*)-3-methoxy-1-(7-((2-methoxy-6-methylphenyl)(methyl)amino)-5-(3,4,5-trifluorophenyl)pyrazolo[1,5-a]pyrimidine-2-carbonyl)piperidin-4-yl)acetic acid represented by chemical

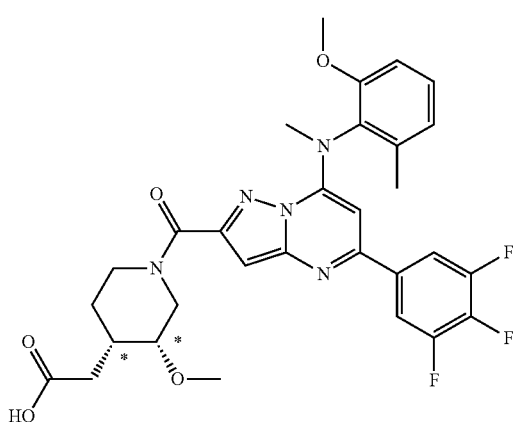

or a pharmaceutically acceptable salt thereof.

[4] (R)-3-(7-((2-fluoro-6-methoxyphenyl)(methyl)amino)-N-methyl-5-(3,4,5-trifluorophenyl)pyrazolo[1,5-a]pyrimidine-2-carboxamide)butanoic acid represented by chemical formula (VII):

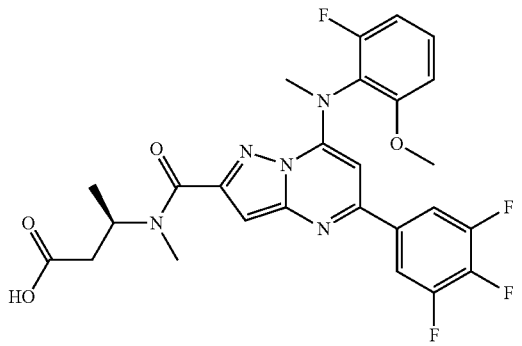

or a pharmaceutically acceptable salt thereof.

[5] 2-((1α,5α,6α)-3-(5-(4-chloro-3,5-difluorophenyl)-7-(isopropyl(propyl)amino)pyrazolo[1,5-a]pyrimidine-2-carbonyl)-3-azabicyclo[3.1.0]hexan-6-yl)acetic acid represented by chemical formula (XV):

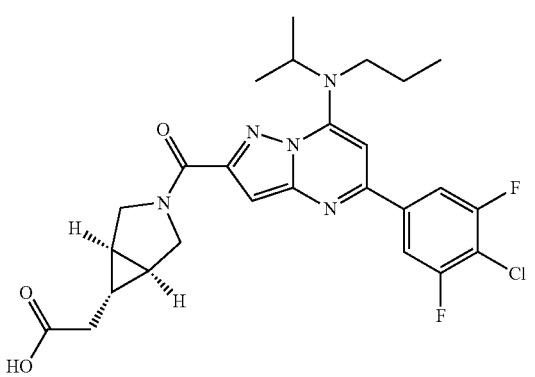

or a pharmaceutically acceptable salt thereof.

[6] A pharmaceutical composition containing a compound according to any one of [1] to [5] or a pharmaceutical acceptable salt thereof.

[7] The pharmaceutical composition according to [6] for treating an inflammatory skin disease or an inflammatory bowel disease.

[8] The pharmaceutical composition according to [6] for treating an inflammatory skin disease.

[9] The pharmaceutical composition according to [6] for treating atopic dermatitis.

[10] The pharmaceutical composition according to [6] for treating contact dermatitis.

[11] The pharmaceutical composition according to [6] for treating skin eczema.

[12] The pharmaceutical composition according to [6] for treating psoriasis.

[13] The pharmaceutical composition according to [6] for treating dry skin dermatitis.

[14] The pharmaceutical composition according to [6] for treating an inflammatory bowel disease.

[15] The pharmaceutical composition according to [6] for treating ulcerative colitis.

[16] The pharmaceutical composition according to [6] for treating Crohn's disease.

[17] The pharmaceutical composition according to [6] for treating infectious enteritis.

[18] An agent for treating an inflammatory skin disease, comprising a compound according to any one of [1] to [5] or a pharmaceutically acceptable salt thereof.

[19] An agent for treating atopic dermatitis, comprising a compound according to any one of [1] to [5] or a pharmaceutically acceptable salt thereof.

[20] An agent for treating contact dermatitis, comprising a compound according to any one of [1] to [5] or a pharmaceutically acceptable salt thereof.

[21] An agent for treating skin eczema, comprising a compound according to any one of [1] to [5] or a pharmaceutically acceptable salt thereof.

[22] An agent for treating psoriasis, comprising a compound according to any one of [1] to [5] or a pharmaceutically acceptable salt thereof.

[23] An agent for treating dry skin dermatitis, comprising a compound according to any one of [1] to [5] or a pharmaceutically acceptable salt thereof.
[24] An agent for treating an inflammatory bowel disease, comprising a compound according to any one of [1] to [5] or a pharmaceutically acceptable salt thereof.
[25] An agent for treating ulcerative colitis, comprising a compound according to any one of [1] to [5] or a pharmaceutically acceptable salt thereof.
[26] An agent for treating Crohn's disease, comprising a compound according to any one of [1] to [5] or a pharmaceutically acceptable salt thereof.
[27] An agent for treating infectious enteritis, comprising a compound according to any one of [1] to [5] or a pharmaceutically acceptable salt thereof.
[28] A method for treating an inflammatory skin disease, comprising administering a compound according to any one of [1] to [5] or a pharmaceutically acceptable salt thereof to a patient.
[29] A method for treating atopic dermatitis, comprising administering a compound according to any one of [1] to [5] or a pharmaceutically acceptable salt thereof to a patient.
[30] A method for treating contact dermatitis, comprising administering a compound according to any one of [1] to [5] or a pharmaceutically acceptable salt thereof to a patient.
[31] A method for treating skin eczema, comprising administering a compound according to any one of [1] to [5] or a pharmaceutically acceptable salt thereof to a patient.
[32] A method for treating psoriasis, comprising administering a compound according to any one of [1] to [5] or a pharmaceutically acceptable salt thereof to a patient.
[33] A method for treating dry skin dermatitis, comprising administering a compound according to any one of [1] to [5] or a pharmaceutically acceptable salt thereof to a patient.
[34] A method for treating an inflammatory bowel disease, comprising administering a compound according to any one of [1] to [5] or a pharmaceutically acceptable salt thereof to a patient.
[35] A method for treating ulcerative colitis, comprising administering a compound according to any one of [1] to [5] or a pharmaceutically acceptable salt thereof to a patient.
[36] A method for treating Crohn's disease, comprising administering a compound according to any one of [1] to [5] or a pharmaceutically acceptable salt thereof to a patient.
[37] A method for treating infectious enteritis, comprising administering a compound according to any one of [1] to [5] or a pharmaceutically acceptable salt thereof to a patient.
[38] The compound according to any one of [1] to [5] or a pharmaceutically acceptable salt thereof, used for treating an inflammatory skin disease.
[39] The compound according to any one of [1] to [5] or a pharmaceutically acceptable salt thereof, used for treating atopic dermatitis.
[40] The compound according to any one of [1] to [5] or a pharmaceutically acceptable salt thereof, used for treating contact dermatitis.
[41] The compound according to any one of [1] to [5] or a pharmaceutically acceptable salt thereof, used for treating skin eczema.
[42] The compound according to any one of [1] to [5] or a pharmaceutically acceptable salt thereof, used for treating psoriasis.
[43] The compound according to any one of [1] to [5] or a pharmaceutically acceptable salt thereof, used for treating dry skin dermatitis.
[44] The compound according to any one of [1] to [5] or a pharmaceutically acceptable salt thereof, used for treating an inflammatory bowel disease.
[45] The compound according to any one of [1] to [5] or a pharmaceutically acceptable salt thereof, used for treating ulcerative colitis.
[46] The compound according to any one of [1] to [5] or a pharmaceutically acceptable salt thereof, used for treating Crohn's disease.
[47] The compound according to any one of [1] to [5] or a pharmaceutically acceptable salt thereof, used for treating infectious enteritis.
[48] Use of a compound according to any one of [1] to [5] or a pharmaceutically acceptable salt thereof for producing an agent for treating an inflammatory skin disease.
[49] Use of a compound according to any one of [1] to [5] or a pharmaceutically acceptable salt thereof for producing an agent for treating atopic dermatitis.
[50] Use of a compound according to any one of [1] to [5] or a pharmaceutically acceptable salt thereof for producing an agent for treating contact dermatitis.
[51] Use of a compound according to any one of [1] to [5] or a pharmaceutically acceptable salt thereof for producing an agent for treating skin eczema.
[52] Use of a compound according to any one of [1] to [5] or a pharmaceutically acceptable salt thereof for producing an agent for treating psoriasis.
[53] Use of a compound according to any one of [1] to [5] or a pharmaceutically acceptable salt thereof for producing an agent for treating dry skin dermatitis.
[54] Use of a compound according to any one of [1] to [5] or a pharmaceutically acceptable salt thereof for producing an agent for treating an inflammatory bowel disease.
[55] Use of a compound according to any one of [1] to [5] or a pharmaceutically acceptable salt thereof for producing an agent for treating ulcerative colitis.
[56] Use of a compound according to any one of [1] to [5] or a pharmaceutically acceptable salt thereof for producing an agent for treating Crohn's disease.
[57] Use of a compound according to any one of [1] to [5] or a pharmaceutically acceptable salt thereof for producing an agent for treating infectious enteritis.

The compounds represented by formulas (I) to (XVIII) according to the present invention (hereinafter also referred to as Compounds (I) to (XVIII)) or pharmaceutically acceptable salts thereof have PAR2 inhibitory action. Thus, Compounds (I) to (XVIII) according to the present invention or pharmaceutically acceptable salts thereof have the potential to be used as the treatment agent for the diseases for which PAR2 inhibitory action is effective such as inflammatory skin diseases.

DETAILED DESCRIPTION

Hereinafter, the meanings of signs, terms and the like used herein will be explained, and the present invention will be described in detail.

The PAR2 inhibitor in the present specification is not particularly limited as long as a compound acts in a direction to inhibit PAR2 activity and refers to a concept including compounds reducing an expression level of PAR2, PAR2 antagonists and compounds suppressing PAR2 signals. The "compound reducing an expression level of PAR2" herein refers to compounds reducing an expression level of mRNA encoding PAR2 or compounds reducing a protein level of PAR2.

Compounds (I) to (XVIII) of the present invention and pharmaceutically acceptable salts thereof may include crystal polymorphs but are not limited to any specific crystal polymorphs and may be any single crystal form or a mixture thereof, both of which are included in the scope of the present claims. Additionally, Compounds (I) to (XVIII) of the present invention and pharmaceutically acceptable salts thereof may be an anhydride, hydrate or solvate, all of which are included in the scope of the present claims.

The present invention also includes isotopically labelled Compounds (I) to (XVIII). Compounds (I) to (XVIII) labelled with an isotope are identical to Compounds (I) to (XVIII), except that one or more atoms are substituted by atoms having an atomic mass or mass number different from the atomic mass or mass number typically found in nature. Isotopes to be incorporated into the compounds of the present invention are, for example, the isotopes of hydrogen, carbon, nitrogen, oxygen, fluorine, chlorine, phosphorus, sulfur and iodine, including $^2H$, $^3H$, $^{11}C$, $^{14}C$, $^{13}N$, $^{15}O$, $^{18}F$, $^{32}P$, $^{35}S$, $^{123}I$ and $^{125}I$. The compounds of the present invention containing these isotopes and/or other isotopes and pharmaceutically acceptable derivatives thereof (for example, salts) are also included in the scope of the present claims.

The isotopically labelled compounds of the present invention, for examples, the compounds with radioactive isotopes such as $^3H$ and/or $^{14}C$ incorporated therein, may be useful for pharmaceutical drugs and/or a tissue distribution assay of a matrix. $^3H$ and $^{14}C$ are considered to be useful for the preparation and easy detection thereof. Isotopes and $^{18}F$ are considered to be useful for PET (positive emission tomography), isotope $^{125}I$ is considered to be useful for SPECT (single photon emission computed tomography), and these isotopes are all useful for brain imaging. Substitution with a heavier isotope such as $^2H$ offers certain therapeutic benefits such as an increase of half-life in vivo or reduction of a necessary dose due to higher metabolic stability, and is thus considered to be useful under certain circumstances. Compounds labelled with an isotope of Compounds (I) to (XVIII) of the present invention can be prepared all in the same manner by following the procedure disclosed in Examples below using an easily available isotopically labelled reagent in place of a non isotopically labelled reagent.

Compounds (I) to (XVIII) of the present invention may be in the form of a salt. The salt is not particularly limited as long as it is pharmaceutically acceptable, but specific examples include inorganic acid salts (e.g., hydrochloride, hydrobromide, sulfate, nitrate and phosphate), organic acid salts (e.g., acetate, succinate, fumarate, maleate, tartrate, citrate, lactate, stearate, benzoate, mandelate, methanesulfonate, ethanesulfonate, p-toluenesulfonate and benzenesulfonate), acidic amino acid salts (e.g., aspartate and glutamate), inorganic basic salts (e.g., alkali metal salts such as sodium salt and potassium salt, alkaline earth metal salts such as calcium salt and magnesium salt, aluminum salt and ammonium salt), organic basic salts (e.g., diethylamine salt, diethanolamine salt, meglumine salt and N,N'-dibenzylethylenediamine salt) and basic amino acid salts (e.g., arginine salt, lysine salt and ornithine salt).

The embodiments of the present invention are the compounds selected from the group consisting of the following compounds or pharmaceutically acceptable salts thereof.

2-((3R*,4S*)-1-(7-((2,6-dimethylphenyl)(methyl)amino)-5-(3,4,5-trifluorophenyl)pyrazolo[1,5-a]pyrimidine-2-carbonyl)-3-fluoropiperidin-4-yl)acetic acid.

2-((3R*,4S*)-1-(7-((2,6-dimethylphenyl)(methyl)amino)-5-(3,4,5-trifluorophenyl)pyrazolo[1,5-a]pyrimidine-2-carbonyl)-3-methoxypiperidin-4-yl)acetic acid, 2-((3R*,4S*)-1-(5-(4,4-dimethylcyclohexyl)-7-((2,6-dimethylphenyl)(methyl)amino)pyrazolo[1,5-a]pyrimidine-2-carbonyl)-3-fluoropiperidin-4-yl) acetic acid, 2-((3R*,4S*)-1-(5-(3-chloro-4-fluorophenyl)-7-((2,6-dimethylphenyl)(methyl)amino)pyrazolo[1,5-a]pyrimidine-2-carbonyl)-3-methoxypiperidin-4-yl)acetic acid, 2-((3R*,4S*)-3-fluoro-1-(7-((2-methoxy-6-methylphenyl)(methyl)amino)-5-(3,4,5-trifluorophenyl)pyrazolo[1,5-a]pyrimidine-2-carbonyl)piperidin-4-yl)acetic acid, 2-((3R*,4S*)-3-methoxy-1-(7-((2-methoxy-6-methylphenyl)(methyl)amino)-5-(3,4,5-trifluorophenyl)pyrazolo[1,5-a]pyrimidine-2-carbonyl)piperidin-4-yl)acetic acid, (R)-3-(7-((2-fluoro-6-methoxyphenyl)(methyl)amino)-N-methyl-5-(3,4,5-trifluorophenyl)pyrazolo[1,5-a]pyrimidine-2-carboxamide)butanoic acid, 2-((1α,5α,6α)-3-(5-(4-chloro-3,5-difluorophenyl)-7-(isobutyl((R)-3-methylbutan-2-yl)amino)pyrazolo[1,5-a]pyrimidine-2-carbonyl)-3-azabicyclo[3.1.0]hexan-6-yl)acetic acid, (R)-3-(7-(isobutyl((R)-3-methylbutan-2-yl)amino)-N-methyl-5-(3,4,5-trifluorophenyl)pyrazolo[1,5-a]pyrimidine-2-carboxamide)butanoic acid, 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl) acetic acid, 2-((3R*,4S*)-1-(5-(4-chloro-3-fluorophenyl)-7-((2-chloro-6-methylphenyl)(methyl)amino)pyrazolo[1,5-a]pyrimidine-2-carbonyl)-3-methoxypiperidin-4-yl)acetic acid, 2-((3R*,4S*)-1-(5-(4-chloro-3,5-difluorophenyl)-7-((2-chloro-6-methylphenyl)(methyl)amino)pyrazolo[1,5-a]pyrimidine-2-carbonyl)-3-methoxypiperidin-4-yl)acetic acid, 2-((3R*,4S*)-1-(7-((2-chloro-6-fluorophenyl)(methyl)amino)-5-(3,4,5-trifluorophenyl)pyrazolo[1,5-a]pyrimidine-2-carbonyl)-3-fluoropiperidin-4-yl)acetic acid, 2-((3R*,4S*)-1-(5-(4-chloro-3,5-difluorophenyl)-7-((2-chlorophenyl)(methyl)amino)pyrazolo[1,5-a]pyrimidine-2-carbonyl)-3-fluoropiperidin-4-yl)acetic acid, 2-((1α,5α,6α)-3-(5-(4-chloro-3,5-difluorophenyl)-7-(isopropyl(propyl)amino)pyrazolo[1,5-a]pyrimidine-2-carbonyl)-3-azabicyclo[3.1.0]hexan-6-yl)acetic acid, 2-((1α,5α,6=)-3-(7-(isobutyl((S)-1-phenylethyl)amino)-5-(3,4,5-trifluorophenyl)pyrazolo[1,5-a]pyrimidine-2-carbonyl)-3-azabicyclo[3.1.0]hexan-6-yl)acetic acid, 2-(1-(7-((2-chloro-6-fluorophenyl)methyl)amino)-5-(3,4,5-trifluorophenyl)pyrazolo[1,5-a]pyrimidine-2-carbonyl)piperidin-4-yl)acetic acid, and 2-((3R*,4S*)-1-(5-(4-chloro-3,5-difluorophenyl)-7-(isopropyl(propyl)amino)pyrazolo[1,5-a]pyrimidine-2-carbonyl)-3-methylpiperidin-4-yl)acetic acid.

Examples of the preferable embodiment of the present invention include 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid represented by chemical formula (X)

(X)

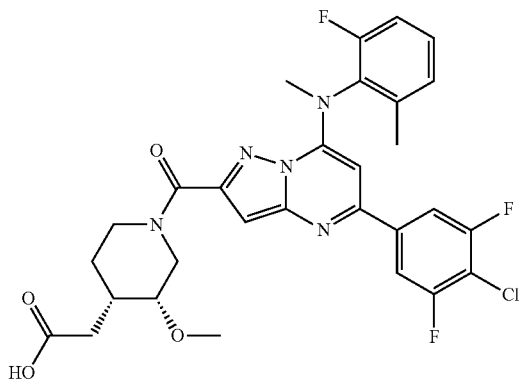

or a pharmaceutically acceptable salt thereof;
2-((3R*,4S*)-3-methoxy-1-(7-((2-methoxy-6-methylphenyl)(methyl)amino)-5-(3,4,5-trifluorophenyl)pyrazolo[1,5-a]pyrimidine-2-carbonyl)piperidin-4-yl)acetic acid represented by chemical formula (VI)

(VI)

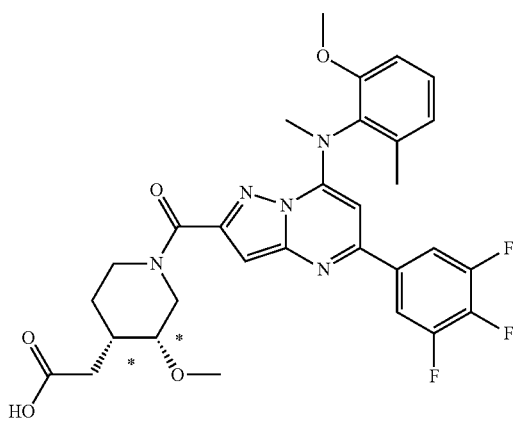

or a pharmaceutically acceptable salt thereof;
(R)-3-(7-((2-fluoro-6-methoxyphenyl)(methyl)amino)-N-methyl-5-(3,4,5-trifluorophenyl)pyrazolo[1,5-a]pyrimidine-2-carboxamide)butanoic acid represented by chemical formula (VII)

(VII)

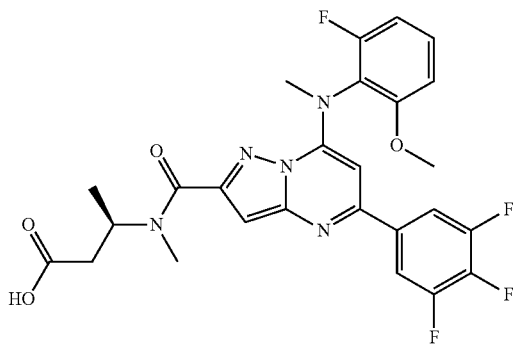

or a pharmaceutically acceptable salt thereof;

2-((1α,5α,6α)-3-(5-(4-chloro-3,5-difluorophenyl)-7-(isopropyl(propyl)amino)pyrazolo[1,5-a]pyrimidine-2-carbonyl)-3-azabicyclo[3.1.0]hexan-6-yl)acetic acid represented by chemical formula (XV)

(XV)

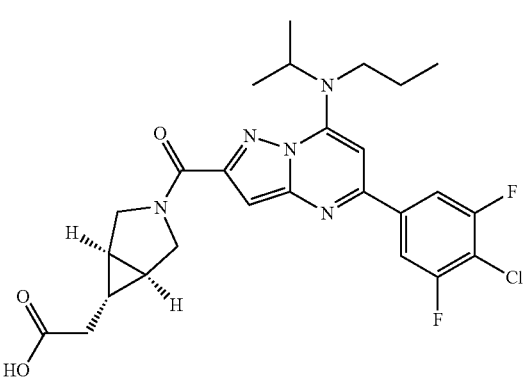

or a pharmaceutically acceptable salt thereof.

Compounds (I) to (XVIII) of the present invention can be prepared as pharmaceutically acceptable salts as necessary by a conventional method. The pharmaceutically acceptable salts of Compounds (I) to (XVIII) can be produced by suitably combining methods typically used in the field of synthetic organic chemistry. Similarly, Compounds (I) to (XVIII) obtained in the form of salts of Compounds (I) to (XVIII) can be converted to a free base of Compounds (I) to (XVIII) in accordance with a conventional method. Additionally, Compounds (I) to (XVIII) of the present invention can be converted as necessary to a solvate by carrying out a known solvate formation reaction.

Various isomers (e.g., geometrical isomer, optical isomer having an asymmetric carbon, rotamer and stereoisomer) obtained from Compounds (I) to (XVIII) can be purified and isolated using typical separation means such as recrystallization, diastereomeric salt formation, enzymatic resolution method, various chromatographies, (e.g., thin layer chromatography, column chromatography and gas chromatography).

The pharmaceutical composition according to the present invention can be produced by mixing pharmaceutically acceptable additives with Compounds (I) to (XVIII) or pharmaceutically acceptable salts thereof. The pharmaceutical composition according to the present invention can be produced in accordance with a known method described in, for example, General Rules for Preparations in The Japanese Pharmacopoeia Sixteenth Edition.

The pharmaceutical composition according to the present invention can be suitably administered to a patient in accordance with the dosage form thereof.

In the present specification, examples of the measurement method for the PAR2 inhibitory activity include measurement method for a concentration elevation of intracellular calcium; measurement method for a production increase of intracellular inositol trisphosphate; measurement method for an increase in intracellular protein phosphorylation by protein kinase C and MAP kinase; and measurement method for a production amount or a release amount of inflammation-related physiologically active substances such as cytokine, chemokine, prostaglandin and nitric oxide. Examples of the measurement method for an elevation of intracellular calcium concentration include a method wherein a calcium-binding fluorescent probe is allowed to be incorporated in advance into a cultured cell line or an animal-derived isolated cell having PAR2, or a cell in which PAR2 is artificially expressed, a protease having the PAR2 activity function such as trypsin or a PAR2 agonist (synthetic peptides such as SLIGKV-NH2 (SEQ ID NO: 1) and SLI-GRL-NH2 (SEQ ID NO: 2) is added to activate PAR2 whereby fluctuating intracellular calcium concentrations are detected as changes in the fluorescent signal. Alternatively, it is also possible to measure an intracellular calcium concentration by determining the quantity of a fluorescence intensity produced in proportion to the calcium concentration using a calcium-binding luminescent protein overexpressing cell line such as Aequorin. Specifically, examples include the methods described in Test Examples of the present specification.

Compounds (I) to (XVIII) according to the present invention or pharmaceutically acceptable salts thereof are those indicating preferably an IC50 value of 30 nM or less, further preferably an IC50 value of 10 nM or less, in terms of the intracellular calcium elevation-suppressive activity.

Compounds (I) to (XVIII) according to the present invention or pharmaceutically acceptable salts thereof have the PAR2 inhibitory action and thus have the potential to be used as the treatment agent for the diseases to which the PAR2 inhibitory action is effective. Examples of the diseases known with which the PAR2 inhibitory action is associated include inflammatory skin diseases (e.g.: atopic dermatitis, contact dermatitis, dry skin dermatitis, psoriasis, skin eczema, scleroderma), inflammatory bowel diseases (e.g.: ulcerative colitis, Crohn's disease, infectious enteritis, regional enteritis), Alzheimer's disease, allergic contact hypersensitivity, neurodegenerative diseases (acute and chronic), autoimmune diseases, conjunctivitis, abnormal wound healing, pain and nerve tissue-derived neurogenic inflammation accompanied by pain.

The dose of Compounds (I) to (XVIII) according to the present invention or pharmaceutically acceptable salts thereof varies depending on the level of symptoms, age, sex, body weight, administration form/kind of salt and the specific type of a disease, but is typically administered to an adult by oral administration in about 30 μg to 10 g, preferably 100 μg to 5 g, further preferably 100 μg to 1 g, a day, or by injection administration in about 30 μg to 1 g, preferably 100 μg to 500 mg, further preferably 100 μg to 300 mg, respectively once or in several divided doses.

EXAMPLES

Compounds (I) to (XVIII) of the present invention can be produced by, for example, the methods described in the following Examples and the effect of such compounds can be verified by the methods described in the following Test Examples. However, these are illustrative, and the present invention is not limited to the following specific examples under any circumstances and changes may be made within the range in which the scope of the present invention is not affected.

Compounds with a literature name, or the like, indicate that they were produced in accordance with the literature, or the like.

Hereinafter, the present invention is described in detail with Examples, Production Examples and Test Examples. However, the present invention is not limited thereto. Additionally, the abbreviations used in Examples are common abbreviations well known by those skilled in the art, some of which are shown below.

DMF: N,N-Dimethylformamide
DMSO: Dimethyl sulfoxide
DMSO-$d_6$: Deuterated dimethyl sulfoxide
HATU: O-(7-Azabenzotriazol-1-yl)-N,N,N',N'-tetramethyluronium hexafluorophosphate
HOBT: 1-Hydroxybenzotriazole
NMP: 1-Methyl-2-pyrrolidone
$Pd_2DBA_3$: Tris(dibenzylideneacetone)dipalladium
t-: Tertiary
THF: Tetrahydrofuran
WSC: 1-Ethyl-3-(3-dimethylaminopropyl)-carbodiimide hydrochloride
$^1$H-NMR: Proton nuclear magnetic resonance spectrometry The chemical shift of the proton nuclear magnetic resonance spectrum is recorded in δ unit (ppm) relative to tetramethylsilane and the coupling constant is recorded in hertz (Hz). Splitting patterns are as follows.

s; singlet, d; doublet, t; triplet, q; quartet, br; broad, m; multiplet, dd; double doublet, td; triple doublet.

$^1$H-NMR was measured using a Varian MERCURY plus model nuclear magnetic resonance apparatus (400 MHz), a Varian INOVA UNITY model nuclear magnetic resonance apparatus (400 MHz), a Varian INOVA UNITY model nuclear magnetic resonance apparatus (500 MHz) or a Bruker Avance model nuclear magnetic resonance apparatus (600 MHz).

For a microwave apparatus, Biotage Initiator or Initiator+ model was used.

The optical rotation was measured using a JASCO DIP-1000 model polarimeter.

For the chromatography, the silica gel used was either Merck Silica Gel 60 (70-230 mesh ASTM), Fuji Silysia Chemical Ltd. PSQ60B, Kanto Kagaku Silica Gel 60 (spherical, 40-50 μM) or YMC YMC*GEL ODS-A (12 nM S-50 μM), or a pre-packed column {column: YAMAZEN Hi-Flash™ Column (Silicagel), size; either S (16×60 mm), M (20×75 mm), L (26×100 mm), 2 L (26×150 mm) or 3 L (46×130 mm)} was used.

NH silica gel used was either Fuji Silysia Chemical Ltd. CHROMATOREX NH-DM2035 or a pre-packed column {column: YAMAZEN Hi-Flash™ Column (Amino), size; either S (16×60 mm), M (20×75 mm), L (26×100 mm), 2 L (26×150 mm) or 3 L (46×130 mm) or a Wako Pure Chemical Industries, Ltd. Presep™ (Luer Lock) NH2 (HC), size; type M (14 g/25 mL), type L (34 g/70 mL), type 2 L (50 g/100 mL), type 3 L (110 g/200 mL)}.

The "room temperature" in the following Examples and Production Examples typically indicates about 10° C. to about 35° C. The "%" indicates a weight percent unless otherwise specified.

The chemical names for the compounds in the following Examples and Production Examples were created based on the chemical structures using "E-Notebook" version 12 (PerkinElmer Co., Ltd.). However, the "*" in the configuration represents a relative position and indicates either one of the enantiomers unless otherwise specified. Further, in the case where "(3R*,4S*)" is written, the relative relationship of each stereocenter is indicated. More specifically, the "(3R*,4S*)" indicates either one of the specific enantiomers (3R,4S) or (3S,4R).

The mixture of rotamers in the present specification means a mixture of isomers having different conformations caused by intramolecular rotations around single bonds such as C—C, C—N and C—O.

Production Example 1

Synthesis of 2-((3R*,4S*)-3-fluoropiperidin-4-yl)acetic acid ethyl ester hydrobromide

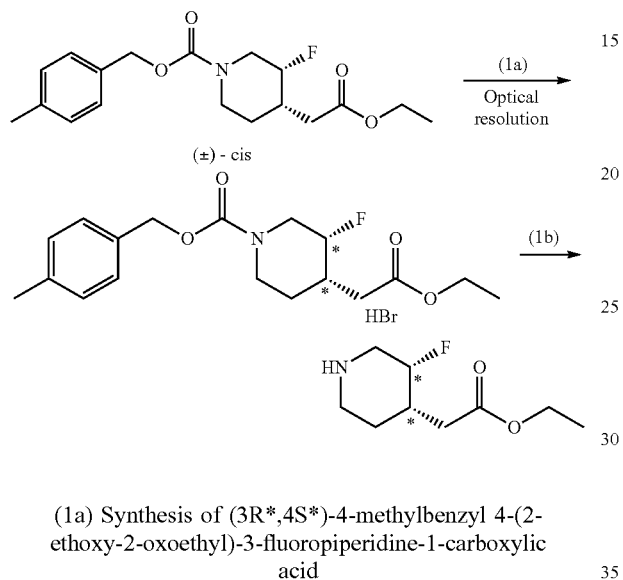

(1a) Synthesis of (3R*,4S*)-4-methylbenzyl 4-(2-ethoxy-2-oxoethyl)-3-fluoropiperidine-1-carboxylic acid Using a CHIRAL PAK IA column, the enantiomers of (±)-cis-4-methylbenzyl 4-(2-ethoxy-2-oxoethyl)-3-fluoropiperidine-1-carboxylic acid (1.0 g) (CAS No. 808733-17-7) (WO 2004/108705) were separated (optical resolution) under the following conditions, to obtain the title compound (0.336 g) as the second eluting fraction.
HPLC conditions
Column: CHIRAL PAK IA (Lot: IA-00CJ-NH005) 20 mm×250 mm, 5 μm;
Mobile phase:Hexane:ethanol=89:11;
Elution rate: 20 mL/min;
Concentration: 62.5 mg/mL;
Injection amount: 0.80 mL;
HPLC retention time: 14.5 min (later-eluting fraction)
$^1$H-NMR (400 MHz, CDCl$_3$) δ: 1.26 (t, J=8 Hz, 3H), 1.50-1.72 (m, 2H), 2.05-2.18 (m, 1H), 2.30 (dd, J=17, 7 Hz, 1H), 2.35 (s, 3H), 2.53 (dd, J=17, 7 Hz, 1H), 2.73-3.10 (m, 2H), 4.15 (q, J=8 Hz, 2H), 4.20-4.80 (m, 3H), 5.09 (m, 2H), 7.15 (d, J=8 Hz, 2H), 7.25 (d, J=8 Hz, 2H).

(1b) Synthesis of 2-((3R*,4S*)-3-fluoropiperidin-4-yl)acetic acid ethyl ester hydrobromide A 30% hydrogen bromide/acetic acid solution (3 mL) was added to a mixture of (3R*,4S*)-4-methylbenzyl 4-(2-ethoxy-2-oxoethyl)-3-fluoropiperidine-1-carboxylic acid (0.336 g) and dichloromethane (3 mL) and stirred at room temperature for 30 minutes. Diethyl ether (10 mL) was added to the reaction mixture, which was concentrated under reduced pressure, t-Butyl methyl ether (10 mL) was added to the residue and sonicated for 10 minutes. The deposited solid was collected by filtration, washed with t-butyl methyl ether, to obtain the title compound (0.236 g) as a light brown solid.
$^1$H-NMR (400 MHz, CDCl$_3$) δ: 1.25 (t, J=8 Hz, 3H), 1.72-1.94 (m, 2H), 2.24-2.32 (m, 2H), 2.55-2.61 (m, 1H), 3.08-3.15 (m, 1H), 3.24-3.30 (m, 1H), 3.34-3.40 (m, 1H), 3.57-3.68 (m, 1H), 4.15 (q, J=8 Hz, 2H), 4.99 (d, J=48 Hz, 1H).

Production Example 2

Synthesis of 2-((3R*,4S*)-3-methoxypiperidin-4-yl)acetic acid ethyl ester hydrochloride

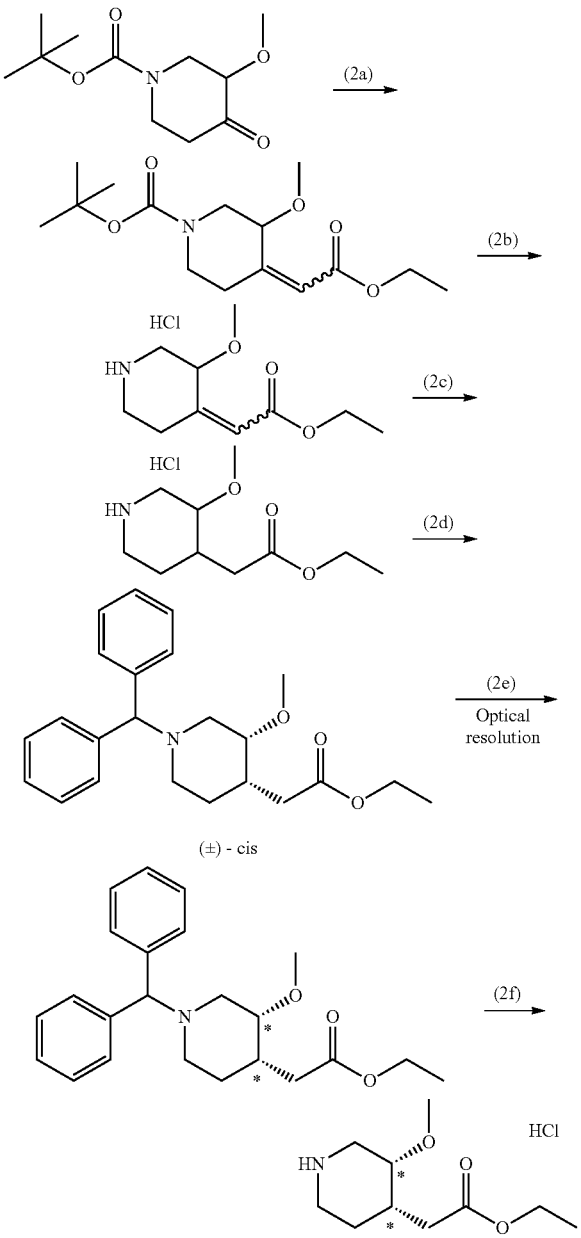

(2a) Synthesis of 4-(2-ethoxy-2-oxoethylidene)-3-methoxypiperidine-1-carboxylic acid t-butyl ester Under a nitrogen atmosphere at room temperature, sodium hydride (about 60%, 2.95 g) was added to a solution of ethyl diethylphosphonoacetate (16.56 g) in THF (340 mL), stirred for 15 minutes, subsequently a solution of 3-methoxy-4-oxopiperidine-1-carboxylic acid t-butyl ester (14.11 g) (WO 2012/080735) in tetrahydrofuran (50 mL) was added dropwise and stirred at room temperature for 16 hours. Ethyl acetate (1000 mL) and a saturated sodium hydrogen carbonate aqueous solution (400 mL) were added to the reaction mixture. The organic layer was dried over anhydrous magnesium sulfate. The drying agent was filtered off and the filtrate was concentrated under reduced pressure. The residue was purified by silica gel column chromatography (heptane-ethyl acetate system), to obtain the title compound (14.65 g).

$^1$H-NMR (400 MHz, CDCl$_3$, E/Z mixture) δ: 1.29 (t, J=7.3 Hz, 3H), 1.47 (s, 4.5H), 1.48 (s, 4.5H), 1.98 (m, 0.5H), 2.52-2.83 (m, 2H), 3.2-3.97 (m, 3H), 3.30 (s, 1.5H), 3.37 (s, 1.5H), 3.80-4.58 (m, 1H), 4.18 (m, 2H), 5.21 (br.s, 0.5H), 5.83 (s, 0.5H), 5.94 (s, 0.5H).

(2b) Synthesis of 2-(3-methoxypiperidin-4-ylidene)acetic acid ethyl ester hydrochloride Trifluoroacetic acid (4 mL) was added to a solution of 4-(2-ethoxy-2-oxoethylidene)-3-methoxypiperidine-1-carboxylic acid t-butyl ester (1.20 g) in dichloromethane (20 mL) and the mixture was stirred at room temperature for 5 hours. The reaction mixture was concentrated under reduced pressure, toluene (100 mL) was added thereto and concentrated under reduced pressure. Toluene (10 mL) was added again, the reaction mixture was concentrated under reduced pressure, subsequently ethyl acetate (10 mL), toluene (10 mL) and a 4N hydrogen chloride ethyl acetate solution (5 mL) were added to the residue and concentrated under reduced pressure, to obtain the title compound (0.95 g).

$^1$H-NMR (400 MHz, CDCl$_3$) δ: 1.29 (t, J=7 Hz, 1.5H), 1.29 (t, J=7 Hz, 1.5H), 2.92-3.20 (m, 3H), 3.33 (s, 1.5H), 3.34 (s, 1.5H), 3.25-3.91 (m, 4H), 4.16-4.24 (m, 2H), 5.98 (s, 0.5H), 6.00 (s, 0.5H), 7.95 (br.s, 0.5H), 8.43 (br.s, 0.5H), 10.11 (br.s, 1H).

(2c) Synthesis of 2-(3-methoxypiperidin-4-yl)acetic acid ethyl ester hydrochloride Palladium-activated carbon (Pd10%) (0.21 g) was added to a mixture of 2-(3-methoxypiperidin-4-ylidene)acetic acid ethyl ester hydrochloride (0.95 g), ethanol (10 mL) and ethyl acetate (10 mL) and stirred at room temperature for 17 hours under a hydrogen atmosphere. The atmosphere was returned to nitrogen, the mixture was filtered through Celite and the Celite was washed with ethanol. The filtrate and the washing solution were combined and concentrated under reduced pressure, to obtain the title compound (1.02 g, mostly cis isomer).

$^1$H-NMR (400 MHz, CDCl$_3$, cis isomer) δ: 1.27 (t, J=7 Hz, 3H), 1.71 (br.d, J=14 Hz, 1H), 1.94 (br.q, J=14 Hz, 1H), 2.15 (m, 1H), 2.32 (dd, J=16, 6 Hz, 1H), 2.54 (dd, J=16, 8 Hz, 1H), 2.94 (m, 2H), 3.41 (s, 3H), 3.44-3.65 (m, 3H), 4.15 (q, J=7 Hz, 2H), 7.84 (br.s, 1H), 9.92 (br.s, 1H).

(2d) Synthesis of (±)-2-(cis-1-benzhydryl-3-methoxypiperidin-4-yl)acetic acid ethyl ester Under a nitrogen atmosphere, at −20° C., a solution of bromodiphenylmethane (2.62 g) in DMF (5 mL) was added to a mixture of 2-(3-methoxypiperidin-4-yl)acetic acid ethyl ester hydrochloride (2.098 g), DMF (80 mL), triethylamine (1.35 mL) and potassium carbonate (2.44 g) and stirred at room temperature overnight. t-Butyl methyl ether (400 mL) and water (200 mL) were added thereto. The organic layer was washed sequentially with water (200 mL×2) and a saturated sodium chloride aqueous solution (200 mL) and dried over anhydrous magnesium sulfate. The drying agent was filtered off and the filtrate was concentrated under reduced pressure. The residue was purified by silica gel column chromatography (heptane-ethyl acetate system), to obtain the title compound (1.127 g) as a colorless liquid.

$^1$H-NMR (400 MHz, CDCl$_3$) δ: 1.24 (t, J=7 Hz, 3H), 1.51 (m, 1H), 1.69 (m, 1H), 1.94-2.12 (m, 3H), 2.27 (dd, J=16, 7 Hz, 1H), 2.52 (dd, J=16, 7 Hz, 1H), 2.72 (br.s, 1H), 2.98 (br.s, 1H), 3.28 (S, 3H), 3.29 (br.s, 1H), 4.11 (q, J=7 Hz, 2H), 4.26 (s, 1H), 7.19 (m, 2H), 7.27 (m, 4H), 7.44 (m, 4H).

(2e) Synthesis of 2-((3R*,4S*)-1-benzhydryl-3-methoxypiperidin-4-yl) acetic acid ethyl ester Using a CHIRALPAK OJ-H column, the enantiomers of (±)-2-(cis-1-benzhydryl-3-methoxypiperidin-4-yl)acetic acid ethyl ester (1.127 g) were separated (optical resolution) under the following conditions, to obtain the title compound (0.411 g) as the first eluting fraction.
HPLC conditions
Column: CHIRAL PAK OJ-H (Lot; OJH-0CJ-FA001), 20 mm×250 mm, 5 μm;
Mobile phase:Hexane:ethanol=98:2;
Elution rate: 20 mL/min;
Concentration: 67 mg/mL;
Injection amount: 0.3 mL;
HPLC retention time: 10.5 min (first-eluting fraction)

$^1$H-NMR (400 MHz, CDCl$_3$) δ: 1.24 (t, J=7 Hz, 3H), 1.49 (m, 1H), 1.69 (m, 1H), 1.94-2.12 (m, 3H), 2.27 (dd, J=16, 7 Hz, 1H), 2.52 (dd, J=16, 7 Hz, 1H), 2.72 (br.s, 1H), 2.98 (br.s, 1H), 3.27 (s, 3H), 3.29 (br.s, 1H), 4.11 (q, J=7 Hz, 2H), 4.26 (s, 1H), 7.19 (m, 2H), 7.27 (m, 4H), 7.44 (m, 4H).

(2f) Synthesis of 2-((3R*,4S*)-3-methoxypiperidin-4-yl)acetic acid ethyl ester hydrochloride A mixture of 2-((3R*,4S*)-1-benzhydryl-3-methoxypiperidin-4-yl)acetic acid ethyl ester (411 mg), 1N hydrochloric acid (1.118 mL), palladium-activated carbon (Pd 5%) (0.238 g), cyclohexene (20 mL) and ethanol (80 mL) was stirred at 90° C. for 18 hours. The reaction mixture was filtered through Celite and the Celite was washed with ethanol (50 mL×2). The filtrate and the washing solution were combined and concentrated under reduced pressure. A mixed solvent of heptane and toluene (10 mL, 1:1) and 2N hydrochloric acid (20 mL) were added to the residue and the layers were separated. The organic layer was extracted with 2N hydrochloric acid (20 mL). A 5N sodium hydroxide aqueous solution was added to the combined aqueous layers to alkalize and the layers were extracted with dichloromethane (50 mL×2). The combined organic layers were dried over anhydrous magnesium sulfate. The drying agent was filtered off, a 4N hydrogen chloride ethyl acetate solution (2 mL) was added to the filtrate and concentrated under reduced pressure, to obtain the title compound (119 mg).

$^1$H-NMR (400 MHz, CD$_3$OD) δ: 1.25 (t, J=7 Hz, 3H), 1.72 (m, 1H), 1.76 (m, 1H), 2.20 (m, 1H), 2.34 (dd, J=17, 7 Hz, 1H), 2.52 (dd, J=17, 8 Hz, 1H), 3.02 (m, 2H), 3.27 (m, 1H), 3.41 (s, 3H), 3.60 (m, 2H), 4.14 (q, J=7 Hz, 2H).

Production Example 3

Synthesis of (R)-3-(methylamino)butanoic acid methyl ester hydrochloride

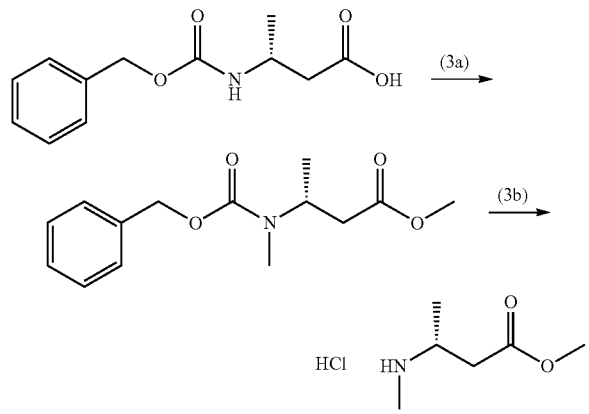

(3a) Synthesis of (R)-3-(((benzyloxy)carbonyl) methyl)amino)butanoic acid methyl ester (R)-3-(((Benzyloxy)carbonyl)amino)butanoic acid (CAS No. 67843-72-5)(1.5 g) was dissolved in THF (40 mL) and sodium hydride (456 mg) was added thereto. THF (30 mL) and methyl iodide (6 g) were added and stirred at room temperature overnight. The reaction mixture was concentrated, water was added and extracted with t-butyl methyl ether. 1N Hydrochloric acid was added to the aqueous layer to acidify the aqueous layer, which was then extracted with t-butyl methyl ether and the organic layer was dried over magnesium sulfate. The drying agent was filtered off and the filtrate was concentrated under reduced pressure. The residue was dissolved in a mixed solvent of dichloromethane and methanol (20 mL, 4:1) and trim ethyl silyldiazo methane (2M solution, 7 mL) was added under ice cooling until the reaction mixture turned yellow. The reaction mixture was stirred at room temperature and concentrated. The residue was purified by silica gel column chromatography (heptane-ethyl acetate system), to obtain the title compound (1.5 g).

$^1$H-NMR (500 MHz, CDCl$_3$) δ: 1.21 (br.s, 3H), 2.30-2.69 (m, 2H), 2.83 (s, 3H), 3.62 (m, 3H), 4.64 (d, J=6 Hz, 1H), 5.14 (br.s, 2H), 7.30-7.43 (m, 5H).
Mass spectrum (ESI) m/z: 266 (M+H)$^+$ (3b) Synthesis of (R)-3-(methylamino)butanoic acid methyl ester hydrochloride (R)-3-(((benzyloxy)carbonyl)(methyl)amino)butanoic acid methyl ester (108 mg) was dissolved in methanol (5 mL), palladium carbon (50 mg) was added and stirred at room temperature for 20 minutes under a hydrogen atmosphere. The reaction mixture was filtered, a 0.5N hydrogen chloride methanol solution (2 mL) was added to the filtrate and concentrated, to obtain the title compound (70 mg).

$^1$H-NMR (400 MHz, DMSO-d$_6$) δ: 1.19 (d, J=7 Hz, 3H), 2.57 (dd, J=17, 9 Hz, 1H), 2.85 (dd, J=17, 5 Hz, 1H), 3.42 (m, 1H), 3.59 (s, 3H), 3.72 (br.s, 3H), 8.88 (br.s, 2H).

Production Example 4

Synthesis of 2-((1α,5α,6α)-3-azabicyclo[3.1.0] hexan-6-yl)acetic acid methyl ester hydrochloride

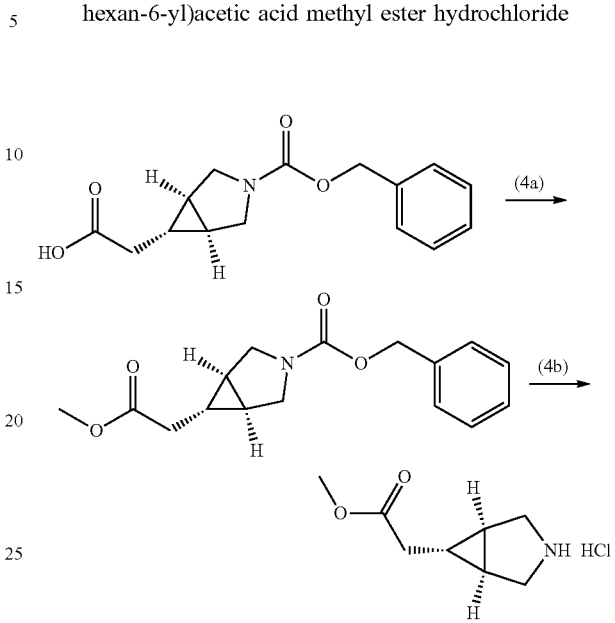

(4a) Synthesis of (1α,5α,6α)6-(2-methoxy-2-oxo-ethyl)-3-azabicyclo[3.1.0]hexane-3-carboxylic acid benzyl ester A solution of trimethylsilyldiazomethane in 2M hexane (0.15 mL) was added at 0° C. to a mixture of 2-((1α,5α,6α)-3-((benzyloxy)carbonyl)-3-azabicyclo[3.1.0]hexan-6-yl)acetic acid (CAS No. 1251668-95-7) (62 mg), methanol (1 mL) and ethyl acetate (4 mL) and subsequently stirred at room temperature for 1 hour. Acetic acid was added until the color of solution disappeared and the reaction mixture was concentrated under reduced pressure. The residue was purified by silica gel column chromatography (heptane-ethyl acetate system), to obtain the title compound (32 mg).

$^1$H-NMR (400 MHz, CDCl$_3$) δ: 0.91 (m, 1H), 1.41 (br.s, 2H), 2.23 (dd, J=16, 7 Hz, 1H), 2.32 (dd, J=16, 7 Hz, 1H), 3.42 (t, J=9 Hz, 2H), 3.65-3.72 (m, 5H), 5.10 (m, 2H), 7.28-7.37 (m, 5H).

(4b) Synthesis of 2-((1α,5α,6α)-3-azabicyclo[3.1.0] hexan-6-yl)acetic acid methyl ester hydrochloride (1α,5α,6α)-6-(2-methoxy-2-oxoethyl)-3-azabicyclo [3.1.0]hexane-3-carboxylic acid benzyl ester (32 mg) was dissolved in methanol (2 mL), palladium carbon (10 mg) was added and stirred at room temperature for 1.5 hours under a hydrogen atmosphere. The reaction mixture was filtered, a 4N hydrogen chloride ethyl acetate solution (0.05 mL) was added to the filtrate and concentrated, to obtain the title compound (26 mg).

$^1$H-NMR (400 MHz, CD$_3$OD) δ: 0.95 (m, 1H), 1.74 (m, 2H), 2.37 (m, 2H), 3.38-3.45 (m, 4H), 3.68 (s, 3H).

Production Example 5

Synthesis of 2-((3R*,4S*)-3-methylpiperidin-4-yl)acetic acid isopropyl ester hydrochloride

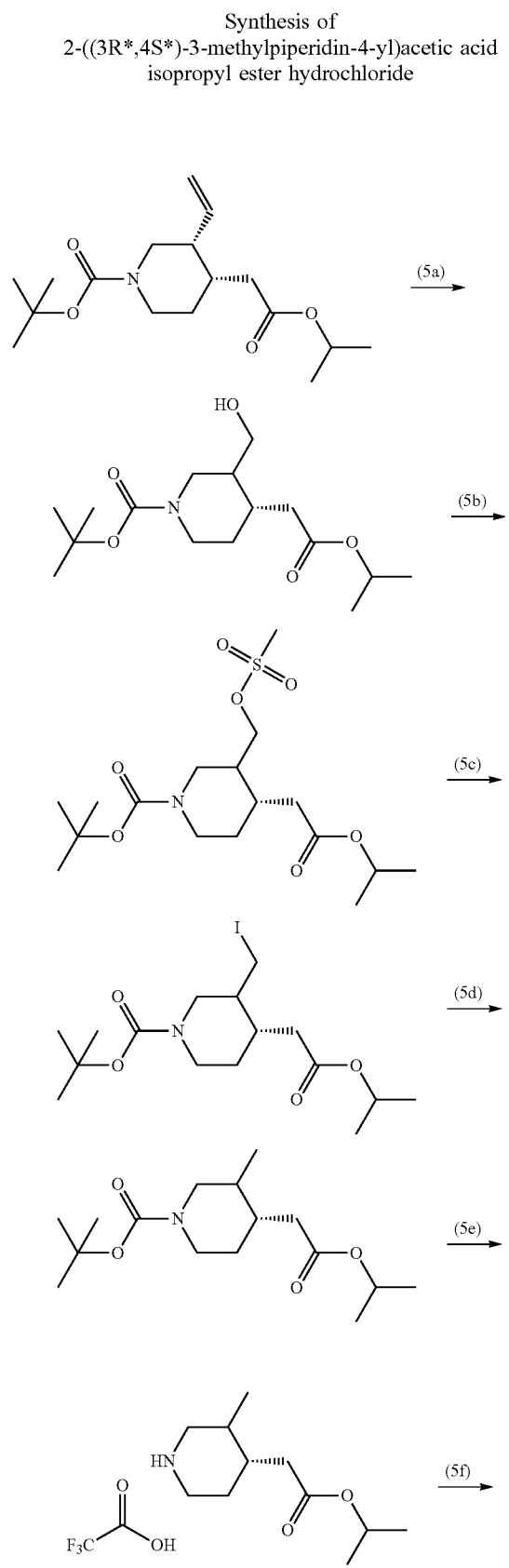

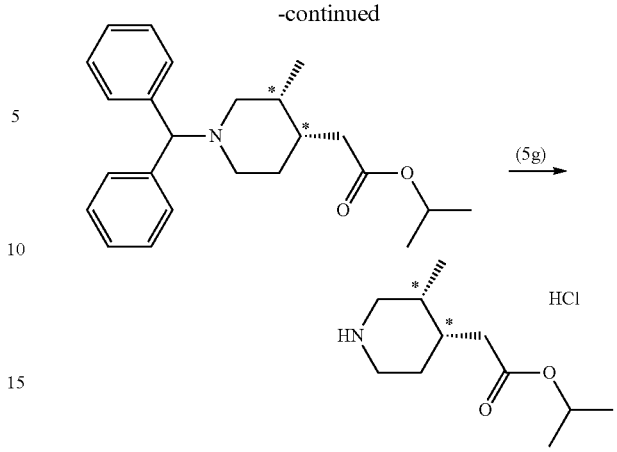

(5a) Synthesis of (4S)-3-(hydroxymethyl)-4-(2-isopropoxy-2-oxoethyl)piperidine-1-carboxylic acid t-butyl ester Under a nitrogen atmosphere, a mixture of (3R,4S)-4-(2-isopropoxy-2-oxoethyl)-3-vinylpiperidine-1-carboxylic acid t-butyl ester (CAS No. 345223-81-6) (16.69 g), dichloromethane (200 mL) and methanol (400 mL) was cooled using dry ice-ethanol as a refrigerant and ozone was blown in for 1 hour while stirring (Nihon Ozone Generator Co., Ltd. HYD-G5000, O2 flow rate: 1.5 L/min). After blowing in nitrogen for 15 minutes to remove excess ozone, sodium tetrahydroborate (6.08 g) was added to the subdivided reaction solutions (540 mL) to be used for the next reaction and subsequently the reaction mixture was allowed to come to room temperature. The reaction mixture was cooled to 0° C., sodium tetrahydroborate (2.03 g) was further added and stirred for 1 hour. Excess reducing agent was quenched with acetone, ethyl acetate (600 mL) and water (100 mL) were added and pH was adjusted to 5-6 using citric acid. The organic layer was dried over anhydrous magnesium sulfate, the drying agent was filtered off and the filtrate was concentrated under reduced pressure. The residue was purified by silica gel column chromatography (heptane-ethyl acetate system), to obtain the title compound (9.09 g).

$^1$H-NMR (400 MHz, CDCl$_3$) δ: 1.23-1.25 (m, 6H), 1.30-1.42 (m, 1H), 1.45-1.47 (m, 10H), 1.91-2.47 (m, 4H), 2.75-2.97 (m, 2H), 3.28-3.58 (m, 2H), 3.90-4.25 (m, 2H), 4.96-5.06 (m, 1H).

(5b) Synthesis of (4S)-4-(2-isopropoxy-2-oxoethyl)-3-(((methylsulfonyl)oxy)methyl)piperidine-1-carboxylic acid t-butyl ester Under a nitrogen atmosphere, a mixture of (4S)-3-(hydroxymethyl)-4-(2-isopropoxy-2-oxoethyl)piperidine-1-carboxylic acid t-butyl ester (9.09 g) and dichloromethane (300 mL) was cooled using dry ice-acetone as a refrigerant and methanesulfonyl chloride (3.59 mL) and triethylamine (6.02 mL) were added while stirring. The reaction mixture was stirred overnight until returned to room temperature and dichloromethane (500 mL) and a 5% sulfuric acid aqueous solution (100 mL) were added. The organic layer was washed sequentially with a saturated sodium hydrogen carbonate aqueous solution (100 mL), water (100 mL) and a saturated sodium chloride aqueous solution (100 mL). Anhydrous magnesium sulfate was added to dry the organic layer, subsequently the drying agent was filtered off and concentrated, to obtain a crude product of the title compound (11.34 g).

$^1$H-NMR (400 MHz, CDCl$_3$) δ: 1.23-1.25 (m, 6H), 1.30-1.42 (m, 1H), 1.45-1.80 (m, 10H), 2.11-2.52 (m, 4H), 2.74-2.97 (m, 2H), 3.04 (m, 3H), 3.75-4.28 (m, 4H), 4.97-5.05 (m, 1H).

(5c) Synthesis of (4S)-3-(iodomethyl)-4-(2-isopropoxy-2-oxoethyl)piperidine-1-carboxylic acid t-butyl ester A mixture of (4S) 4-(2-isopropoxy-2-oxoethyl)-3-(((methylsulfonyl)oxy)methyl)piperidine-1-carboxylic acid t-butyl ester (13.37 g), acetone (200 mL) and sodium iodide (30.6 g) was stirred with heating at 55° C. for 6 hours. After the reaction mixture was cooled to room temperature, ethyl acetate (600 mL) and a saturated sodium thiosulfate aqueous solution were added. The organic Layer was washed sequentially with water (200 mL) and a saturated sodium chloride aqueous solution (200 mL) and subsequently dried over anhydrous magnesium sulfate. The drying agent was filtered off, the filtrate was concentrated under reduced pressure and subsequently the residue was purified by silica gel column chromatography (heptane-ethyl acetate system), to obtain the title compound (9.80 g).

$^1$H-NMR (400 MHz, CDCl$_3$) δ: 1.24-1.28 (m, 6H), 1.30-1.42 (m, 1H), 1.45-1.80 (m, 10H), 2.00-2.48 (m, 4H), 2.73-3.35 (m, 4H), 3.94-4.28 (m, 2H), 4.99-5.07 (m, 1H).

(5d) Synthesis of (4S)-4-(2-isopropoxy-2-oxoethyl)-3-methylpiperidine-1-carboxylic acid t-butyl ester Under a nitrogen atmosphere, zinc (37.7 g) was added to a mixture of (4S)-3-(iodomethyl)-4-(2-isopropoxy-2-oxoethyl)piperidine-1-carboxylic acid t-butyl ester (9.80 g) and acetic acid (151 mL). The reaction mixture was stirred at room temperature for 24 hours and filtered. The removed solid was washed with ethyl acetate. The washing solution and the filtrate were combined and concentrated under reduced pressure. The residue was dissolved in ethyl acetate (800 mL) and a 10% aqueous solution of citric acid (200 mL), the organic layer was dried over anhydrous magnesium sulfate, subsequently filtered and concentrated under reduced pressure. The obtained residue was combined with a residue obtained by the same procedure from (4S)-3-(iodomethyl)-4-(2-isopropoxy-2-oxoethyl)piperidine-1-carboxylic acid t-butyl ester (2.59 g), acetic acid (40 mL) and zinc (9.95 g) in a separate experiment, and purified by silica gel column chromatography (heptane-ethyl acetate system), to obtain the title compound (7.85 g).

$^1$H-NMR (400 MHz, CDCl$_3$) δ: 0.86 (d, J=7 Hz, 2.4H), 0.88 (d, J=7 Hz, 0.6H), 1.23 (m, 6H), 1.45 (m, 11H), 1.83 (br.s, 1H), 2.09-2.25 (m, 3H), 2.74 (br.s, 1H), 2.99 (dd, J=13, 4 Hz, 1H), 3.72-3.78 (m, 1H), 4.04 (br.s, 1H), 4.97-5.06 (m, 1H).

(5e) Synthesis of 2-((4S)-3-methylpiperidin-4-yl)acetic acid isopropyl ester 2,2,2-trifluoroacetate Trifluoroacetic acid (30 mL) was added to a mixture of (4S)-4-(2-isopropoxy-2-oxoethyl)-3-methylpiperidine-1-carboxylic acid t-butyl ester (7.22 g) and dichloromethane (120 mL) and stirred at room temperature for 3 hours. Toluene (100 mL) was added and the reaction mixture was concentrated under reduced pressure. Toluene (100 mL) was added again and the reaction mixture was concentrated under reduced pressure, to obtain the title compound (10.80 g) as a crude product.

$^1$H-NMR (400 MHz, CDCl$_3$) δ: 1.00 (d, J=7 Hz, 0.6H), 1.04 (d, J=7 Hz, 2.4H), 1.24 (d, J=6 Hz, 6H), 1.54-1.89 (m, 2H), 1.95-2.36 (m, 4H), 2.87-3.51 (m, 4H), 5.03 (m, 1H), 8.07 (br.s, 1H), 8.55 (br.s, 1H).

(5f) Synthesis of 2-((3R*,4S*)-1-benzhydryl-3-methylpiperidin-4-yl)acetic acid isopropyl ester Under a nitrogen atmosphere, a mixture of 2-((4S)-3-methylpiperidin-4-yl)acetic acid isopropyl ester 2,2,2-trifluoroacetate (7.55 g) and DMF (200 mL) was cooled to −40° C. and a solution of triethylamine (3.36 mL), potassium carbonate (13.33 g) and bromodiphenylmethane (6.85 g) in DMF (10 mL) was added. The mixture was stirred overnight at room temperature and ethyl acetate (600 mL) and water (300 mL) were added. The organic layer was washed sequentially with water (2×200 mL) and a saturated sodium chloride aqueous solution (200 mL) and subsequently dried over anhydrous magnesium sulfate and filtered. The filtrate was concentrated under reduced pressure and subsequently the residue was purified by silica gel column chromatography (heptane-ethyl acetate system), to obtain the title compound (5.40 g).

$^1$H-NMR (400 MHz, CDCl$_3$) δ: 1.03 (d, J=7 Hz, 3H), 1.20 (d, J=6 Hz, 6H), 1.40-1.48 (m, 1H), 1.51-1.61 (m, 1H), 1.75-1.86 (m, 1H), 1.88-2.10 (m, 3H), 2.16 (dd, J=15, 8 Hz, 1H), 2.22 (dd, J=15, 7 Hz, 1H), 2.58 (br.s, 1H), 2.71 (br.s, 1H), 4.17 (s, 1H), 4.98 (m, 1H), 7.16 (m, 2H), 7.26 (m, 4H), 7.40 (m, 4H).

(5g) Synthesis of 2-((3R*,4S*)-3-methylpiperidin-4-yl)acetic acid isopropyl ester hydrochloride Under a nitrogen atmosphere, palladium-activated carbon (Pd 5%) (3.14 g), 5N hydrochloric acid (2.95 mL) and cyclohexene (150 mL) were added to a mixture of 2-((3R*,4S*)-1-benzhydryl-3-methylpiperidin-4-yl)acetic acid isopropyl ester (5.40 g) and ethanol (500 mL) and heated to reflux for 20 hours. The reaction mixture was cooled and subsequently filtered through Celite and the Celite was washed with ethanol (4×100 mL). The filtrate and the washing solution were combined and concentrated under reduced pressure. The residue was dissolved in toluene (20 mL), heptane (20 mL) and 5N hydrochloric acid (50 mL) and the organic layer was extracted with 5N hydrochloric acid (50 mL). The aqueous layers were combined, adjusted to pH 14 with a 5N sodium hydroxide aqueous solution and extracted with dichloromethane (200 mL, 2×100 mL). The organic layers were combined, dried over anhydrous magnesium sulfate and filtered. A 4N hydrogen chloride ethyl acetate solution (4 mL) was added and concentrated to a volume of 10 mL and t-butyl methyl ether (10 mL) was added. The solvent was concentrated under reduced pressure, to obtain the title compound (2.65 g).

$^1$H-NMR (400 MHz, CD$_3$OD) δ: 1.01 (d, J=7 Hz, 3H), 1.23 (d, J=6 Hz, 6H), 1.67-1.84 (m, 2H), 2.10-2.21 (m, 1H), 2.26-2.40 (m, 3H), 3.03-3.16 (m, 3H), 3.20-3.25 (ddd, J=13, 6, 4 Hz, 1H), 4.99 (m, 1H).

Example 1

Synthesis of 2-(3R*,4S*)-1-(7-((2,6-dimethylphenyl)(methyl)amino)-5-(3,4,5-trifluorophenyl)pyrazolo[1,5-a]pyrimidine-2-carbonyl)-3-fluoropiperidin-4-yl)acetic acid

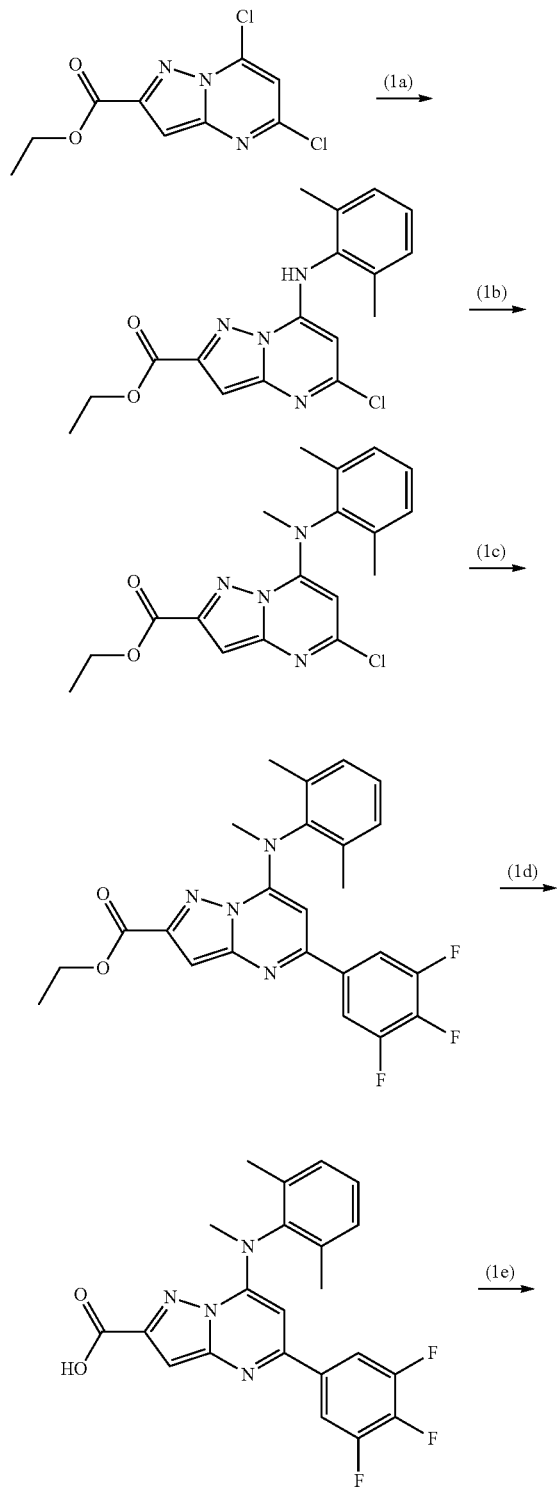

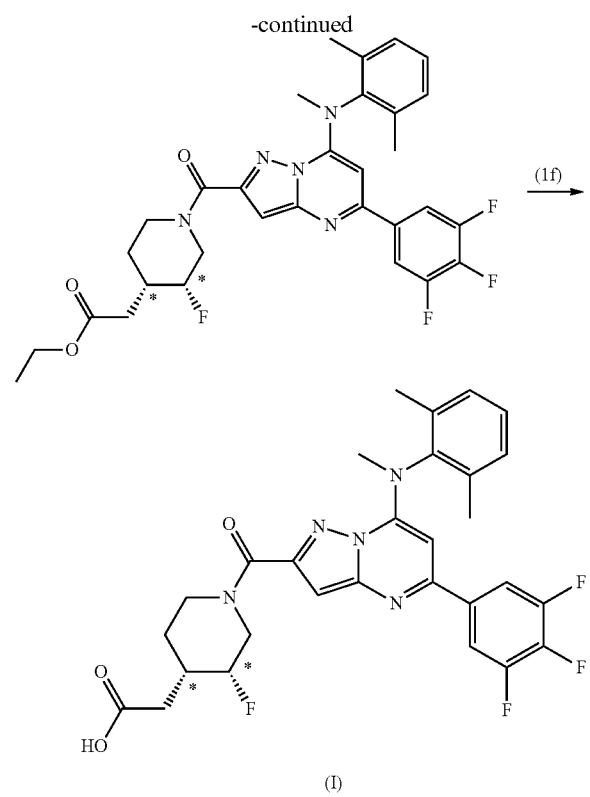

(1a) Synthesis of 5-chloro-7-((2,6-dimethylphenylamino)pyrazolo[1,5-a]pyrimidine-2-carboxylic acid ethyl ester A solution of 5,7-dichloropyrazolo[1,5-a]pyrimidine-2-carboxylic acid ethyl ester (CAS No. 1232224-62-2) (WO 2011/105628) (1.36 g), 2,6-dimethylaniline (CAS No. 87-62-7) (0.76 g), Pd$_2$DBA$_3$ (0.239 g), 2-(dichlorohexylphosphino)biphenyl (0.092 g) and potassium phosphate (1.67 g) in 1,2-dimethoxyethane (15 mL) was stirred at 120° C. for 12 hours in a microwave apparatus. The reaction mixture was diluted with ethyl acetate, subsequently washed with saturated saline and the organic layer was dried over anhydrous magnesium sulfate. The drying agent was filtered off, the filtrate was concentrated and subsequently the residue was purified by silica gel column chromatography (heptane-ethyl acetate system), to obtain the title compound (1.7 g) as a red oily product.

$^1$H-NMR (400 MHz, CDCl$_3$) δ: 1.46 (t, J=7 Hz, 3H), 2.25 (s, 6H), 4.51 (q, J=7 Hz, 2H), 5.60 (s, 1H), 7.00 (s, 1H), 7.27 (m, 3H), 7.86 (s, 1H).

Mass spectrum (ESI) m/z: 345 (M+H)$^+$

(1b) Synthesis of 5-chloro-7-((2,6-dimethylphenyl)(methyl)amino)pyrazolo[1,5-a]pyrimidine-2-carboxylic acid ethyl ester Potassium carbonate (0.75 g) and methyl iodide (0.5 mL) were added to a solution of 5-chloro-7-((2,6-dimethylphenyl)amino)pyrazolo[1,5-a]pyrimidine-2-carboxylic acid ethyl ester (0.93 g) in DMF (20 mL) and stirred at 50° C. for 2 hours. The reaction mixture was diluted with ethyl acetate, subsequently washed twice with saturated saline and the organic layer was dried over anhydrous magnesium sulfate. The drying agent was filtered off, the filtrate was concentrated under reduced pressure and subsequently the residue was purified by silica gel column chromatography (heptane-ethyl acetate system), to obtain the title compound (0.4 g) as a light yellow oily product.

$^1$H-NMR (400 MHz, CDCl$_3$) δ: 1.45 (t, J=7 Hz, 3H), 2.23 (s, 6H), 4.16 (s, 3H), 4.47 (q, J=7 Hz, 2H), 5.25 (s, 1H), 6.68 (s, 1H), 7.24 (m, 3H).
Mass spectrum (ESI) m/z: 359 (M+H)$^+$ (1c) Synthesis of 7-((2,6-dimethylphenyl)(methyl)amino-5-(3,4,5-trifluorophenyl)pyrazolo[1,5-a]pyrimidine-2-carboxylic acid ethyl ester A mixture of 5-chloro-7-((2,6-dimethylphenyl)(methyl)amino)pyrazolo[1,5-a]pyrimidine-2-carboxylic acid ethyl ester (1.8 g), 3,4,5-trifluorophenyl boronic acid (CAS No. 143418-49-9) (971 mg), tetrakis(triphenylphosphine)palladium (0) (290 mg), potassium carbonate (1.59 g), water (0.09 mL) and 1,4-dioxane (10 mL) was stirred at 120° C. for 1.5 hours in a microwave apparatus. The reaction mixture was diluted with ethyl acetate, subsequently washed with saturated saline and the organic layer was dried over anhydrous magnesium sulfate. The drying agent was filtered off and the filtrate was concentrated under reduced pressure. The residue was purified by silica gel column chromatography (heptane-ethyl acetate system), to obtain the title compound (1.9 g) as a light yellow oily product.

$^1$H-NMR (400 MHz, CDCl$_3$, mixture of rotamers) δ: 1.46 (br.s, 3H), 2.25 (s, 6H), 4.21 (s, 3H), 4.49 (br.s, 2H), 5.55 (s, 1H), 7.01 (s, 1H), 7.37 (br.s, 5H).
Mass spectrum (ESI) m/z: 455 (M+H)$^+$ (1d) Synthesis of 7-((2,6-dimethylphenyl)(methyl)amino)-5-(3,4,5-trifluorophenyl)pyrazolo[1,5-a]pyrimidine-2-carboxylic acid A 5N sodium hydroxide aqueous solution (1.25 mL) was added to a solution of 7-((2,6-dimethylphenyl)(methyl)amino)-5-(3,4,5-trifluorophenyl)pyrazolo[1,5-a]pyrimidine-2-carboxylic acid ethyl ester (0.95 g) in 1,4-dioxane (20 mL) and stirred at 90° C. for 2 hours. After bringing back the reaction mixture to room temperature, 5N hydrochloric acid was added to acidify, the produced solid was collected by filtration and washed with ethanol, to obtain 0.88 g of the title compound as a light yellow solid.

$^1$H-NMR (500 MHz, DMSO-d$_6$, mixture of rotamers) δ: 2.04 (s, 4H), 2.20 (s, 2H), 3.48 (s, 2H), 4.07 (s, 1H), 5.62 (s, 0.4H), 6.82-7.32 (m, 4.6H), 7.57 (br.s, 0.7H), 8.26 (s, 1.3H).
Mass spectrum (ESI) m/z: 427 (M+H)$^+$ (1e) Synthesis of 2-((3R*,4S*)-1-(7-((2,6-dimethylphenyl)(methyl)amino)-5-(3,4,5)-trifluorophenyl)pyrazolo[1,5-a]pyrimidine-2-carbonyl)-3-fluoropiperidin-4-yl)acetic acid ethyl, ester 2-((3R*,4S*)-3-fluoropiperidin-4-yl)acetic acid ethyl ester hydrobromide (16.5 mg) (Production Example 1) was added to a solution of 7-((2,6-dimethylphenyl)(methyl)amino)-5-(3,4,5-trifluorophenyl)pyrazolo[1,5-a]pyrimidine-2-carboxylic acid (20 mg), WSC (18.0 mg), HOBT (12.7 mg) and triethylamine (0.013 mL) in DMF (1 mL) and stirred at room temperature for 1 hour. Ethyl acetate and water were added to the reaction mixture to separate the solution. The aqueous layer was extracted twice with ethyl acetate. The combined organic layers were washed with saturated saline and dried over anhydrous magnesium sulfate. The drying agent was filtered off and the filtrate was concentrated under reduced pressure. The residue was purified by silica gel column chromatography (heptane-ethyl acetate system), to obtain the title compound (21 mg).

$^1$H-NMR (400 MHz, CDCl$_3$, mixture of rotamers) δ: 1.26-1.30 (m, 3H), 1.54-1.72 (m, 2H), 2.06-2.18 (m, 7H), 2.25-2.63 (m, 4H), 3.44 (s, 3H), 4.13-4.21 (m, 2H), 4.41-5.14 (m, 2H), 5.52 (s, 1H), 6.46 (br.s, 1H), 6.82-7.39 (m, 4H), 7.73-7.80 (m, 2H).

(1f) Synthesis of 2-((3R*,4S*)-1-(7-((2,6-dimethylphenyl)(methyl)amino)-5-(3,4,5-trifluorophenyl)pyrazolo[1,5-a]pyrimidine-2-carbonyl-3-fluoropiperidin-4-yl)acetic acid 5N Sodium hydroxide aqueous solution (0.2 mL) was added to a solution of 2-((3R*,4S*)-1-(7-((2,6-dimethylphenyl)(methyl)amino)-5-(3,4,5-trifluorophenyl)pyrazolo[1,5-a]pyrimidine-2-carbonyl)-3-fluoropiperidin-4-yl)acetic acid ethyl ester (20 mg) in 1,4-dioxane (1 mL) and stirred at 55° C. for 3 hours. The reaction mixture was purified by reverse phase silica gel column chromatography (acetonitrile-water, 0.1% acetic acid system), to obtain the title compound (9.64 mg).

$^1$H-NMR (600 MHz, DMSO-d$_6$, 42° C., mixture of rotamers) δ: 1.05-1.56 (m, 2H), 2.00-2.08 (m, 7H), 2.17-2.21 (m, 1H), 2.33-2.37 (m, 1H), 2.53-2.92 (m, 2H), 3.48 (s, 3H), 3.97-4.78 (m, 3H), 6.74-6.77 (m, 1H), 7.08-7.12 (m, 4H), 8.25 (m, 2H), 12.11 (br.s, 1H).

Example 2

Synthesis of 2-(3R*,4S*)-1-(7-((2,6-dimethylphenyl)(methyl)amino-5-(3,4,5-trifluorophenyl)pyrazolo[1,5-a]pyrimidine-2-carbonyl)-3-methoxypiperidin-4-yl)acetic acid

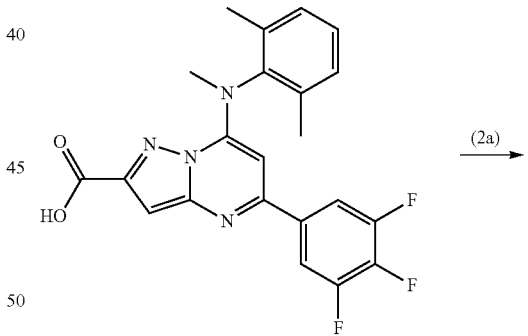

(2a)

Example 1-(1d)

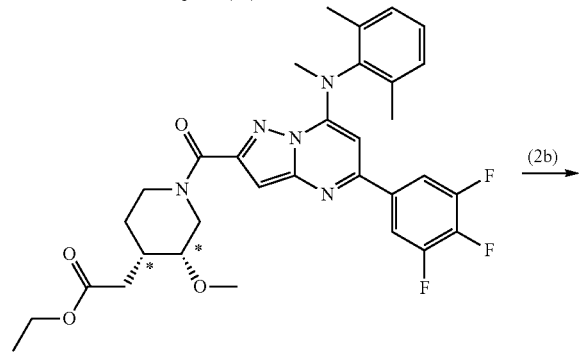

(2b)

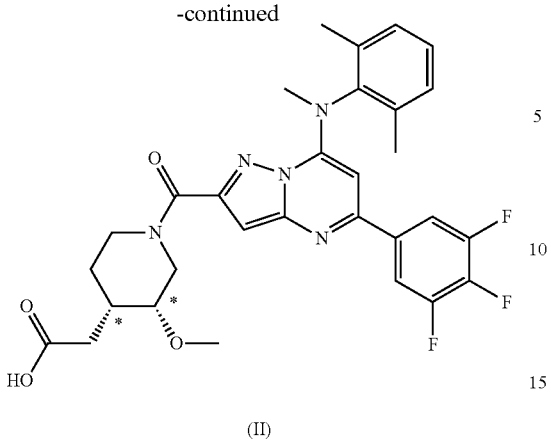

(II)

(2a) Synthesis of 2-(((3R*,4S*)-1-(7-(2,6-dimethylphenyl)(methyl)amino)-5-(3,4,5-trifluorophenyl)pyrazolo[1,5-a]pyrimidine-2-carbonyl)-3-methoxypiperidin-4-yl)acetic acid ethyl ester HOBT (46 mg), WSC (58 mg), 2-((3R,4S*)-3-methoxypiperidin-4-yl)acetic acid ethyl ester hydrochloride (62 mg) (Production Example 2) and triethylamine (81 mg) were sequentially added to a solution of 7-((2,6-dimethylphenyl)(methyl)amino)-5-(3,4,5-trifluorophenyl)pyrazolo[1,5-a]pyrimidine-2-carboxylic acid (85 mg) (Example 1—(1d)) in DMF (5 mL) and stirred at room temperature for 6 hours. Ethyl acetate (50 mL) and water (20 mL) were added to the reaction mixture, and the organic layer was washed with water (20 mL×2) and dried over anhydrous magnesium sulfate. The drying agent was filtered off and the filtrate was concentrated under reduced pressure. The residue was purified by silica gel column chromatography (heptane-ethyl acetate system), to obtain the title compound (108 mg) as a white solid.

$^1$H-NMR (400 MHz, CDCl$_3$, mixture of rotamers) δ: 1.26-1.35 (m, 3H), 1.52-1.91 (m, 2H), 2.22-2.52 (m, 8H), 2.57-2.66 (m, 1H), 3.49-3.56 (m, 7H), 4.10-4.26 (m, 3H), 4.53-4.65 (m, 1H), 4.78-4.87 (m, 1H), 4.98-5.08 (m, 1H), 5.49-6.49 (m, 1H), 6.94-7.02 (m, 1H), 7.20-7.33 (m, 3H), 7.74-7.81 (m, 2H).
Mass spectrum (ESI) m/z: 610 (M+H)$^+$

(2b) Synthesis of 2-(((3R*,4S*)-1-(7-((2,6-dimethylphenyl)methyl)amino)-5-(3,4,5-trifluorophenyl)pyrazolo[1,5-a]pyrimidine-2-carbonyl)-3-methoxypiperidin-4-yl)acetic acid A 4N lithium hydroxide aqueous solution (0.089 mL) was added to a mixture of 2-((3R*,4S*)-1-(7-((2,6-dimethylphenyl)(methyl)amino)-5-(3,4,5-trifluorophenyl)pyrazolo[1,5-a]pyrimidine-2-carbonyl)-3-methoxypiperidin-4-yl)acetic acid ethyl ester (108 mg), 1,4-dioxane (5 mL) and water (1 mL) and stirred at room temperature for 19 hours. Dimethylsulfoxide (1 mL) and acetic acid (0.2 mL) were added, the reaction mixture was concentrated under reduced pressure. The residue was purified by reverse phase silica gel column chromatography (acetonitrile-water, 0.1% acetic acid system), thereby collecting a fraction containing the title compound. The fraction was concentrated under reduced pressure to a volume of about 3 mL, the precipitate was collected by filtration, washed with water (2 mL) and dried under reduced pressure, to obtain the title compound (69 mg).

$^1$H-NMR (600 MHz, CDCl$_3$, 30° C., mixture of rotamers) δ: 1.52-1.91 (m, 2H), 2.22-2.52 (m, 8H), 2.57-2.66 (m, 1H), 3.49-3.56 (m, 7H), 4.15-4.26 (m, 1H), 4.53-4.65 (m, 1H), 4.78-4.87 (m, 1H), 4.98-5.08 (m, 1H), 5.48-6.49 (m, 1H), 6.94-7.02 (m, 1H), 7.20-7.33 (m, 3H), 7.70-7.81 (m, 2H).
Mass spectrum (ESI) m/z: 582 (M+H)$^+$

Example 3

Synthesis of 2-(((3R*,4S*)-1-(5-(4,4-dimethylcyclohexyl)-7-((2,6-dimethylphenyl)(methyl)amino)pyrazolo[1,5-a]pyrimidine-2-carbonyl)-3-fluoropiperidin-4-yl)acetic acid

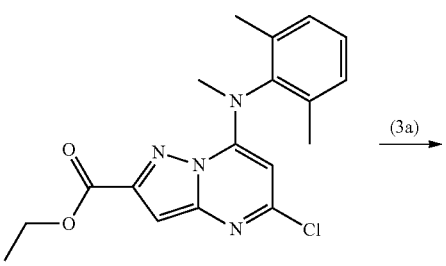

Example 1-(1b)

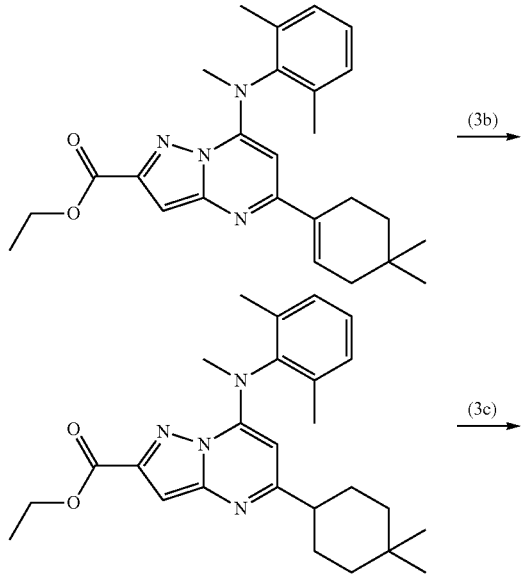

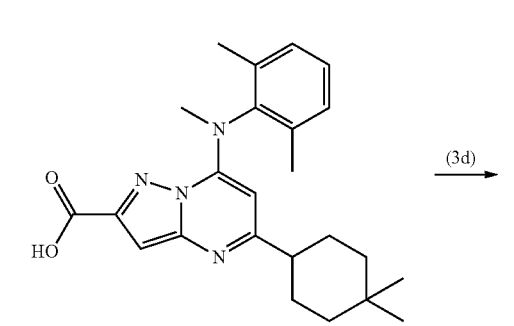

-continued

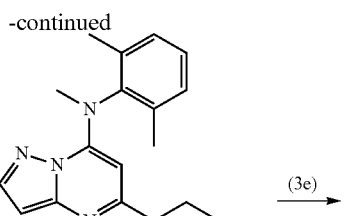

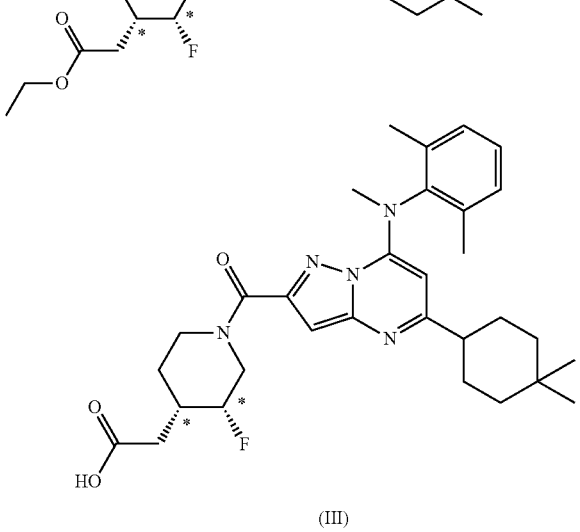

(III)

(3a) Synthesis of 5-(4,4-dimethylcyclohex-1-en-1-yl)-7-((2,6-dimethylphenyl)(methyl)amino)pyrazolo[1,5-a]pyrimidine-2-carboxylic acid ethyl ester Water (3 mL), sodium carbonate (0.27 g), 4,4-(dimethylcyclohexen-1-yl)boronic acid pinacol ester (CAS No. 859217-67-7) (0.35 g) and tetrakis(triphenylphosphine)palladium (0) (0.058 g) were added to a mixture of 5-chloro-7-((2,6-dimethylphenyl)(methyl)amino)pyrazolo[1,5-a]pyrimidine-2-carboxylic acid ethyl ester (0.36 g) (Example 1-(1b)) and 1,4-dioxane (15 mL) and the mixture was stirred with heating at 95° C. for 2 hours under a nitrogen atmosphere. The reaction mixture was diluted with ethyl acetate (150 mL) and water (50 mL) and the organic layer was dried over anhydrous magnesium sulfate. The drying agent was filtered off and the filtrate was concentrated under reduced pressure. The residue was purified by silica gel column chromatography (heptane-ethyl acetate system), to obtain the title compound (0.31 g) as a light yellow solid.

$^1$H-NMR (400 MHz, CDCl$_3$, mixture of rotamers) δ: 0.91 (br.s, 6H), 1.24-1.45 (m, 5H), 1.96 (br.s, 2H), 2.21 (br.s, 6H), 2.32 (br.s, 2H), 4.13 (br.s, 3H), 4.43 (br.s, 2H), 5.44 (br.s, 1H), 6.35 (br.s, 1H), 6.91 (s, 1H), 7.22 (br.s, 3H),

(3b) Synthesis of 5-(4,4-dimethylcyclohexyl)-7-((2,6-dimethylphenyl)methyl)amino)pyrazolo[1,5-a]pyrimidine-2-carboxylic acid ethyl ester 10% Palladium carbon (10 mg) was added to a mixture of 5-(4,4-dimethylcyclohex-1-en-1-yl)-7-((2,6-dimethylphenyl)(methyl)amino)pyrazolo[1,5-a]pyrimidine-2-carboxylic acid ethyl ester (43 mg) and methanol (4 mL) and stirred at room temperature for 2 hours under a hydrogen atmosphere. The reaction mixture was filtered through Celite and the catalyst was filtered off. The Celite and catalyst were washed with ethyl acetate, the filtrate and washing solution were combined and concentrated under reduced pressure, to obtain the title compound (46 mg).

$^1$H-NMR (400 MHz, CDCl$_3$, mixture of rotamers) δ: 0.90 (br.s, 6H), 1.26 (br.s, 3H), 1.35-1.65 (m, 8H), 2.19 (br.s, 6H), 2.30 (br.s, 1H), 4.13 (br.s, 3H), 4.43 (br.s, 2H), 5.17 (br.s, 1H), 6.88 (s, 1H), 7.22 (br.s, 3H).

(3c) Synthesis of 5-(4,4-dimethylcyclohexyl)-7-((2,6-dimethylphenyl)(methyl)amino)pyrazolo[1,5-a]pyrimidine-2-carboxylic acid Water (4 mL) and lithium hydroxide (30 mg) were added to a mixture of 5-(4,4-dimethylcyclohexyl)-7-((2,6-dimethylphenyl)(methyl)amino)pyrazolo[1,5-a]pyrimidine-2-carboxylic acid ethyl ester (271 mg) and 1,4-dioxane (20 mL) and stirred at room temperature for 17 hours. Acetic acid (0.2 mL) and DMSO (4 mL) were added to the reaction mixture, which was concentrated under reduced pressure. The residue was purified by reverse phase silica gel column chromatography (acetonitrile-water, 0.1% acetic acid system), to obtain the title compound (200 mg).

$^1$H-NMR (400 MHz, CDCl$_3$, mixture of rotamers) δ: 0.80-1.08 (m, 6H), 1.15-1.88 (m, 8H), 2.00-2.63 (m, 7H), 3.43 (s, 2.3H), 4.08 (br.s, 0.7H), 5.24 (br.s, 0.3H), 6.13 (br.s, 0.7H), 6.83-7.26 (m, 4H).

(3d) Synthesis of 2-(((3R*,4S*)-1-(5-(4,4-dimethylcyclohexyl)-7-((2,6-dimethylphenyl(methyl)(amino)pyrazolo[1,5-a]pyrimidine-2-carbonyl)-3-fluoropiperidin-4-yl)acetic acid ethyl ester HOBT (63 mg) and WSC (79 mg) were added to a mixture of 5-(4,4-dimethylcyclohexyl)-7-((2,6-dimethylphenyl)(methyl)amino)pyrazolo[1,5-a]pyrimidine-2-carboxylic acid (112 mg) and DMF (5 mL) and stirred at room temperature for 30 minutes. 2-((3R*,4S*)-3-fluoropiperidin-4-yl)acetic acid ethyl ester hydrobromide (82 mg) (Production Example 1) and triethylamine (111 mg) were sequentially added thereto and stirred at room temperature for 15 hours. Ethyl acetate (60 mL) and water (30 mL) were added to the reaction mixture, and the organic layer was washed with water (30 mL×2) and dried over anhydrous magnesium sulfate. The drying agent was filtered off and the filtrate was concentrated under reduced pressure. The residue was purified by silica gel column chromatography (heptane-ethyl acetate system), to obtain the title compound (139 mg).

$^1$H-NMR (500 MHz, CDCl$_3$, mixture of rotamers) δ: 0.81-1.05 (m, 6H), 1.15-1.84 (m, 12H), 1.25 (m, 3H), 2.01-2.36 (m, 8H), 2.47 (m, 1H), 2.60 (br.s, 1H), 3.34 (br.s, 2H), 4.02 (br.s, 1H), 4.17 (m, 2H), 4.26-5.21 (m, 3H), 6.15-6.85 (m, 2H), 6.98-7.34 (m, 3H).

(3e) Synthesis of 2-(((3R*,4S*)-1-(5-((4,4-dimethylcyclohexyl)-7-((2,6-dimethylphenyl)(methyl)amino)pyrazolo[1,5-a]pyrimidine-2-carbonyl)-3-fluoropiperidin-4-yl)acetic acid An aqueous solution (2 mL) of lithium hydroxide (11.5 mg) was added to a solution of 2-((3R*,4S*)-1-(5-(4,4-dimethylcyclohexyl)-7-((2,6-dimethylphenyl)(methyl)amino)pyrazolo[1,5-a]pyrimidine-2-carbonyl)-3-fluoropiperidin-4-yl) acetic acid ethyl ester (139 mg) in 1,4-dioxane (6 mL) and stirred at room temperature for 15 hours. DMSO (2 mL) and acetic acid (0.1 mL) were added to the reaction mixture, which was concentrated under reduced pressure.

The residue was purified by reverse phase silica gel column chromatography (acetonitrile-water, 0.1% acetic acid system), the fractions containing the title compound were combined and concentrated under reduced pressure to a volume of 5 mL. The precipitate was collected by filtration, washed with water (5 mL) and dried under reduced pressure. The title compound (97 mg) was obtained as a light brown solid.

$^1$H-NMR (500 MHz, CD$_3$OD, mixture of rotamers) δ: 0.90-1.08 (m, 6H), 1.15-1.34 (m, 1H), 1.41-1.48 (m, 3H), 1.55-1.65 (m, 2H), 1.72-1.95 (m, 3H), 2.04-2.16 (m, 6H), 2.20-2.40 (m, 3H), 2.41-2.95 (m, 4H), 3.42 (s, 0.7H), 4.08 (s, 2.3H), 4.14-5.25 (m, 3H), 6.40-6.73 (m, 2H), 7.06-7.35 (m, 3H).

Mass spectrum (ESI) m/z: 550 (M+H)$^+$

Example 4

Synthesis of 2-(((3R*,4S*)-1-(5-(3-chloro-4-fluorophenyl)-7-((2,6-dimethylphenyl)(methyl)(amino)pyrazolo[1,5-a]pyrimidine-2-carbonyl)-3-methoxypiperidin-4-yl)acetic acid

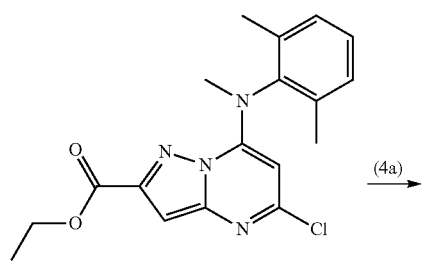

Example 1-(1b)

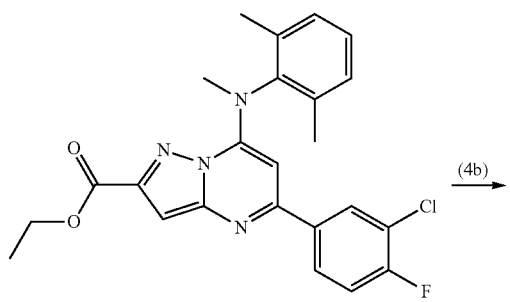

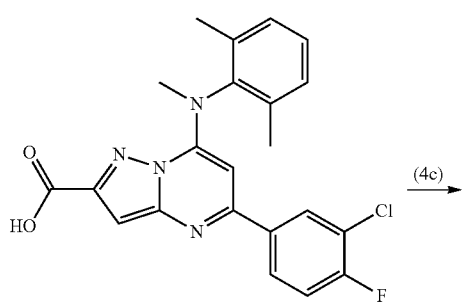

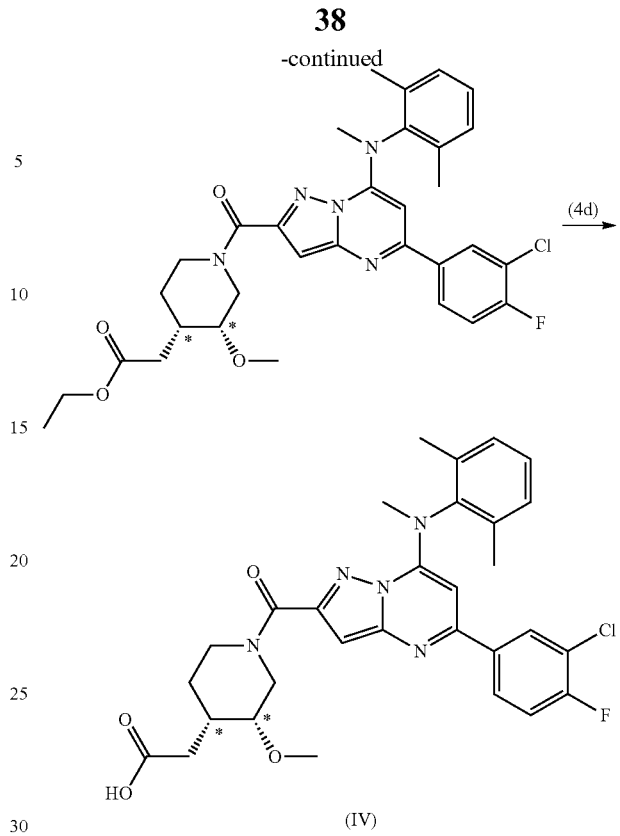

(4a) Synthesis of 5-(3-chloro-4-fluorophenyl)-7-((2,6-dimethylphenyl)(methyl)amino)pyrazolo[1,5-a]pyrimidine-2-carboxylic acid ethyl ester Water (1 mL), sodium carbonate (0.18 g), 3-chloro-4-fluorophenylboronic acid (CAS No. 144432-85-9) (0.14 g) and tetrakis(triphenylphosphine)palladium (0) (0.065 g) were added to a mixture of 5-chloro-7-((2,6-dimethylphenyl)(methyl)amino)pyrazolo[1,5-a]pyrimidine-2-carboxylic acid ethyl ester (269 mg) (Example 1-(1b)) and 1,4-dioxane (10 mL) and the mixture was stirred with heating at 90° C. for 24 hours under a nitrogen atmosphere. The reaction mixture was diluted with ethyl acetate (100 mL) and water (50 mL) and the organic layer was dried over anhydrous magnesium sulfate. The drying agent was filtered off and the filtrate was concentrated under reduced pressure. The residue was purified by silica gel column chromatography (heptane-ethyl acetate system), to obtain the title compound (0.35 g) as a white solid.

$^1$H-NMR (400 MHz, CDCl$_3$, mixture of rotamers) δ: 1.46 (br.s, 3H), 2.25 (s, 6H), 4.20 (s, 3H), 4.49 (br.s, 2H), 5.60 (br.s, 1H), 6.98 (br.s, 1H), 7.12 (br.s, 1H), 7.25 (br.s, 3H), 7.52 (br.s, 1H), 7.86 (br.s, 1H).

Mass spectrum (ESI) m/z: 453 (M+H)$^+$ (4b) Synthesis of 5-(3-chloro-4-fluorophenyl)-7-((2,6-dimethylphenyl)(methyl)(amino)pyrazolo[1,5-a]pyrimidine-2-carboxylic acid Water (1 mL) and a 4N lithium hydroxide aqueous solution (0.39 mL) were added to a mixture of 5-(3-chloro-4-fluorophenyl)-7-((2,6-dimethylphenyl)(methyl)amino)pyrazolo[1,5-a]pyrimidine-2-carboxylic acid ethyl ester (353 mg) and 1,4-dioxane (9 mL) and stirred at room temperature for 20 hours. The reaction mixture was concentrated under reduced pressure, water (3 mL) and acetic acid (0.2 mL) were added to the residue and sonicated. The precipitate was collected by filtration, washed with water (1 mL) and dried under reduced pressure, to obtain the title compound (233 mg) as a light yellow solid.

$^1$H-NMR (500 MHz, CD$_3$OD, mixture of rotamers) δ: 2.12 (s, 1.5H), 2.28 (br.s, 4.5H), 3.54 (s, 0.8H), 4.19 (s, 2.2H), 5.60 (s, 0.7H), 6.80-7.45 (m, 5.3H), 7.54 (br.s, 0.7H), 7.87 (br.s, 0.7H), 8.16 (br.s, 0.3H), 8.33 (br.s, 0.3H).

Mass spectrum (ESI) m/z: 425 (M+H)$^+$ (4c) Synthesis of 2-(((3R*,4S*)-1-(5-(3-chloro-4-fluorophenyl)-7-((2,6-dimethylphenyl)(methyl)amino)pyrazolo[1,5-a]pyrimidine-2-carbonyl)-3-methoxypiperidin-4-yl)acetic acid ethyl ester HOBT (54 mg) and WSC (68 mg) were added to a mixture of 5-(3-chloro-4-fluorophenyl)-7-((2,6-dimethylphenyl)(methyl)amino)pyrazolo[1,5-a]pyrimidine-2-carboxylic acid (100 mg) and DMF (3 mL) and stirred at room temperature for 30 minutes. 2-((3R*,4S*)-3-methoxypiperidin-4-yl)acetic acid ethyl ester hydrochloride (60 mg) (Production Example 2) and triethylamine (95 mg) were added sequentially thereto and stirred at room temperature for 15 hours. Ethyl acetate and water were added to the reaction mixture, and the organic layer was washed with water and dried over anhydrous magnesium sulfate. The drying agent was filtered off and the filtrate was concentrated under reduced pressure. The residue was purified by silica gel column chromatography (heptane-ethyl acetate system), to obtain the title compound (110 mg).

$^1$H-NMR (500 MHz, CDCl$_3$, mixture of rotamers) δ: 1.21-1.83 (m, 2H), 1.27 (m, 3H), 1.95-2.26 (m, 7H), 2.35-2.73 (m, 4H), 2.77-3.13 (m, 1H), 3.22-4.10 (m, 6H), 4.02-5.08 (m, 4H), 5.58 (m, 0.45H), 6.51 (m, 0.55H), 6.78-7.30 (m, 5H), 7.52 (br.s, 0.45H), 7.85 (br.s, 0.45H), 8.00 (br.s, 0.55H), 8.17 (d, J=6 Hz, 0.55H).

Mass spectrum (ESI) m/z: 608 (M+H)$^+$ (4d) Synthesis of 2-(((3R*,4S*)-1-(5-(3-chloro-4-fluorophenyl)-7-((2,6-dimethylphenyl)(methyl)amino)pyrazolo[1,5-a]pyrimidine-2-carbonyl)-3-methoxypiperidin-4-yl)acetic acid Water (1.5 mL) and a 4N lithium hydroxide aqueous solution (0.086 mL) were added to a mixture of 2-((3R*,4S*)-1-(5-(3-chloro-4-fluorophenyl)-7-((2,6-dimethylphenyl)(methyl)amino)pyrazolo[1,5-a]pyrimidine-2-carbonyl)-3-methoxypiperidin-4-yl)acetic acid ethyl ester (105 mg) and 1,4-dioxane (6 mL) and stirred at room temperature for 20 hours. 1N Hydrochloric acid (0.34 mL) was added to the reaction mixture, which was concentrated under reduced pressure. The residue was purified by reverse phase silica gel column chromatography (acetonitrile-water, 0.1% acetic acid system), to obtain the title compound (81 mg).

$^1$H-NMR (400 MHz, CDCl$_3$, mixture of rotamers) δ: 1.21-1.79 (m, 2H), 1.95-2.26 (m, 7H), 2.35-2.74 (m, 4H), 2.75-3.11 (m, 1H), 3.22-3.55 (m, 4.8H), 4.03 (m, 0.2H), 4.09 (s, 1.2H), 4.23 (m, 0.2H), 4.62 (m, 0.8H), 4.84-5.07 (m, 0.4H), 5.57 (m, 0.4H), 6.52 (m, 0.6H), 6.80 (m, 0.4H), 6.98-7.16 (m, 3H), 7.22-7.33 (m, 2H), 7.52 (br.s, 0.4H), 7.85 (br.s, 0.6H), 8.00 (br.s, 0.4H), 8.17 (d, J=7 Hz, 0.6H).

Mass spectrum (ESI) m/z: 580 (M+H)$^+$

Example 5

Synthesis of 2-(((3R*,4S*)-3-fluoro-1-(7-((2-methoxy-6-methyl)phenyl)(methyl)amino)-5-(3,4,5-trifluorophenyl)pyrazolo[1,5-a]pyrimidine-2-carbonyl)piperidin-4-yl)acetic acid

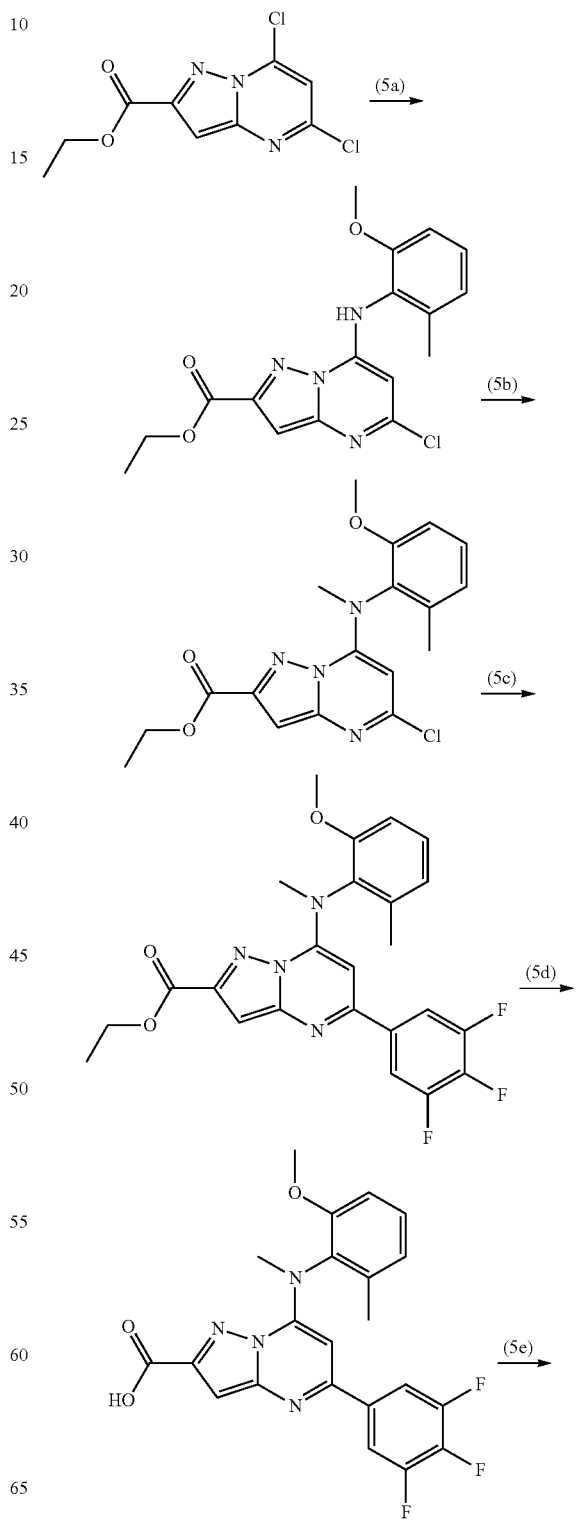

-continued

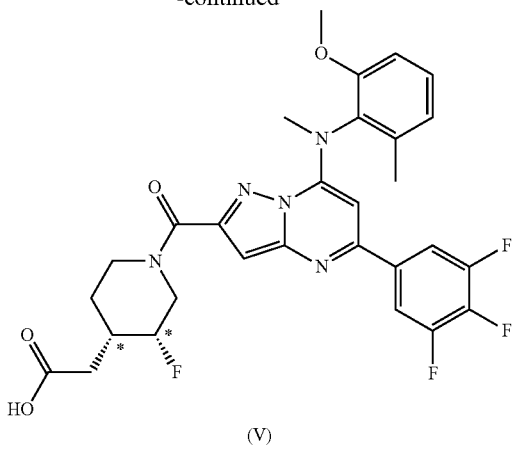

(V)

(5a) Synthesis of 5-chloro-7-((2-methoxy-6-methylphenyl)amino)pyrazolo[1,5-a]pyrimidine-2-carboxylic acid ethyl ester A solution of 5,7-dichloropyrazolo[1,5-a]pyrimidine-2-carboxylic acid ethyl ester (CAS No. 1232224-62-2) (8 g) and 2-methoxy-6-methylaniline (CAS No. 50868-73-0) (4.64 g) in NMP (6 mL) was stirred at 150° C. for 4 hours. Ethyl acetate, DMSO and a saturated sodium hydrogen carbonate aqueous solution were added to the reaction mixture, and the organic layer was washed with saturated saline and dried over anhydrous magnesium sulfate. The drying agent was filtered off and the filtrate was concentrated under reduced pressure, to obtain a crude product of the title compound (10.98 g).
$^1$H-NMR (500 MHz, CDCl$_3$, mixture of rotamers) δ: 1.46 (t, J=7 Hz, 3H), 2.27 (s, 3H), 3.78 (s, 3H), 4.50 (q, J=7 Hz, 2H), 5.66 (s, 1H), 6.88 (d, J=8 Hz, 1H), 6.95 (d, J=8 Hz, 1H), 6.99 (s, 1H), 7.31 (t, J=8 Hz, 1H), 7.80 (s, 1H).
Mass spectrum (ESI) m/z: 361 (M+H)$^+$ (5b) Synthesis of 5-chloro-7-((2-methoxy-6-methylphenyl)(methyl)amino)pyrazolo[1,5-a]pyrimidine-2-carboxylic acid ethyl ester Potassium carbonate (12.62 g) and methyl iodide (5.71 mL) were added to a solution of a crude product (10.98 g) of 5-chloro-7-((2-methoxy-6-methylphenyl)amino)pyrazolo[1,5-a]pyrimidine-2-carboxylic acid ethyl ester in DMF (100 mL) and stirred at 50° C. for 4 hours. Ethyl acetate and water were added to the reaction mixture to separate the solution. The aqueous layer was extracted with ethyl acetate. The combined organic layers were washed sequentially with water and saturated saline and dried over anhydrous magnesium sulfate. The drying agent was filtered off and the filtrate was concentrated under reduced pressure. The residue was purified by silica gel column chromatography (heptane-ethyl acetate system), to obtain the title compound (7.14 g).
$^1$H-NMR (500 MHz, CDCl$_3$, 45° C., mixture of rotamers) δ: 1.39 (t, J=7 Hz, 3H), 2.21 (s, 3H), 3.75 (s, 3H), 3.88 (br.s, 3H), 4.39 (q, J=7 Hz, 2H), 5.56 (br.s, 1H), 6.83 (s, 1H), 6.84 (d, J=7 Hz, 1H), 6.92 (d, J=7 Hz, 1H), 7.27 (t, J=7 Hz, 1H).

(5c) Synthesis of 7-((2-methoxy-6-methylphenyl)(methyl)amino)-5-(3,4,5-trifluorophenyl)pyrazolo[1,5-a]pyrimidine-2-carboxylic acid ethyl ester A mixture of 5-chloro-7-((2-methoxy-6-methylphenyl)(methyl)amino)pyrazolo[1,5-a]pyrimidine-2-carboxylic acid ethyl ester (500 mg), 3,4,5-trifluorophenylboronic acid (282 mg), tetrakis(triphenylphosphine)palladium (0) (77 mg), sodium carbonate (353 mg), water (1.6 mL) and 1,4-dioxane (16 mL) was stirred at 100° C. for 3 hours under a nitrogen atmosphere. Ethyl acetate and saturated saline were added to the reaction mixture, and the organic layer was dried over anhydrous magnesium sulfate. The drying agent was filtered off and the filtrate was concentrated under reduced pressure. The residue was purified by silica gel column chromatography (heptane-ethyl acetate system), to obtain the title compound (668 mg).
$^1$H-NMR (500 MHz, CDCl$_3$, 45° C., mixture of rotamers) δ: 1.40 (t, J=7 Hz, 3H), 2.23 (s, 3H), 3.75 (s, 3H), 3.94 (s, 3H), 4.41 (q, J=7 Hz, 2H), 5.88 (br.s, 1H), 6.88 (d, J=8 Hz, 1H), 6.95 (d, J=7 Hz, 1H), 6.97 (s, 1H), 7.30 (t, J=8 Hz, 1H), 7.49 (m, 2H).
Mass spectrum (ESI) m/z: 471 (M+H)$^+$ (5d) Synthesis of 7-((2-methoxy-6-methylphenyl)(methyl)amino)-5-(3,4,5-trifluorophenyl)pyrazolo[1,5-a]pyrimidine-2-carboxylic acid A 4N lithium hydroxide aqueous solution (1 mL) was added to a solution of 7-((2-methoxy-6-methylphenyl)(methyl)amino)-5-(3,4,5-trifluorophenyl)pyrazolo[1,5-a]pyrimidine-2-carboxylic acid ethyl ester (668 mg) in 1,4-dioxane (5 mL) and stirred at room temperature overnight. 2N Hydrochloric acid (2 mL) was added to the reaction mixture and the deposited solid was collected by filtration, to obtain the title compound (574 mg).
$^1$H-NMR (500 MHz, CDCl$_3$, 45° C., mixture of rotamers) δ: 2.24 (s, 3H), 3.68 (s, 6H), 6.31 (br.s, 1H), 6.80 (d, J=8 Hz, 1H), 6.94 (d, J=8 Hz, 1H), 6.99 (s, 1H), 7.31 (t, J=7 Hz, 1H), 7.67 (m, 2H).
Mass spectrum (ESI) m/z: 443 (M+H)$^+$ (5e) Synthesis of 2-(((3R*,4S*)-3-fluoro-1-(7-((2-methoxy-6-methylphenyl)(methyl)amino)-5-(3,4,5-trifluorophenyl)pyrazolo[1,5-a]pyrimidine-2-carbonyl)piperidin-4-yl)acetic acid N,N-Diisopropylethylamine (0.05 mL) was added to a solution of 7-((2-methoxy-6-methylphenyl)(methyl)amino)-5-(3,4,5-trifluorophenyl)pyrazolo[1,5-a]pyrimidine-2-carboxylic acid (30 mg), 2-((3R*,4S*)-3-fluoropiperidin-4-yl)acetic acid ethyl ester hydrobromide (27 mg) (Production Example 1) and HATU (60 mg) in dichloromethane (1 mL) and stirred at room temperature overnight. Ethyl acetate and water were added to the reaction mixture, and the organic layer was washed sequentially with water and saturated saline and dried over anhydrous magnesium sulfate. The drying agent was filtered off and the filtrate was concentrated under reduced pressure, to obtain a crude product of 2-((3R*,4S*)-3-fluoro-1-(7-((2-methoxy-6-methylphenyl)(methyl)amino)-5-(3,4,5-trifluorophenyl)pyrazolo[1,5-a]pyrimidine-2-carbonyl)piperidin-4-yl)acetic acid ethyl ester. 1,4-Dioxane (1 mL) and a 4N lithium hydroxide aqueous solution (0.2 mL) were added thereto and stirred at room temperature overnight. The reaction mixture, to which 2N hydrochloric acid (0.4 mL) was added, was purified by reverse phase high performance liquid chromatography (acetonitrile-water, 0.1% acetic acid system), to obtain the title compound (2.81 mg).
$^1$H-NMR (600 MHz, Pyridine-d$_5$, 15° C., mixture of rotamers) δ: 1.50-1.81 (m, 2H), 2.23-2.37 (m, 3H), 2.39-2.59 (m, 2H), 2.63-2.69 (m, 1H), 2.74-3.03 (m, 2H), 3.37

(br.s, 3H), 3.48 (br.s, 3H), 4.54-4.70 (m, 1H), 4.90-5.12 (m, 1H), 5.17-5.38 (m, 1H), 6.72-6.99 (m, 4H), 7.43-7.57 (m, 1H), 8.12 (br.s, 2H).

Mass spectrum (ESI) m/z: 586 (M+H)$^+$

Example 6

Synthesis of 2-((3R,4S*)-3-methoxy-1-(7-((2-methoxy-6-methylphenyl)methyl)amino)-5-(3,4,5-trifluorophenyl)pyrazolo[1,5-a]pyrimidine-2-carbonyl)piperidin-4-yl)acetic acid

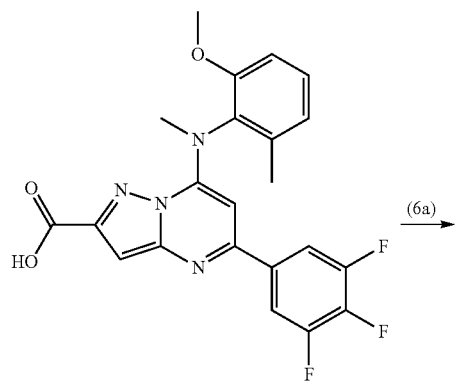

Example 5-(5d)

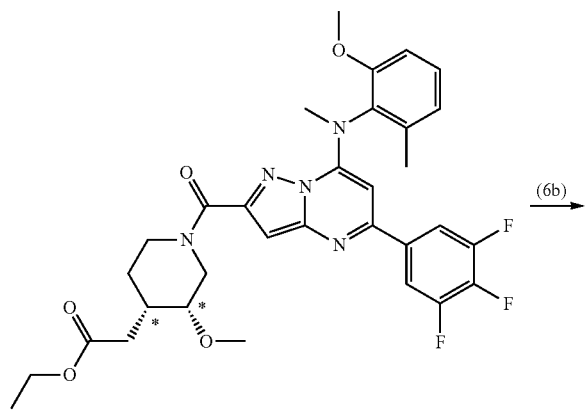

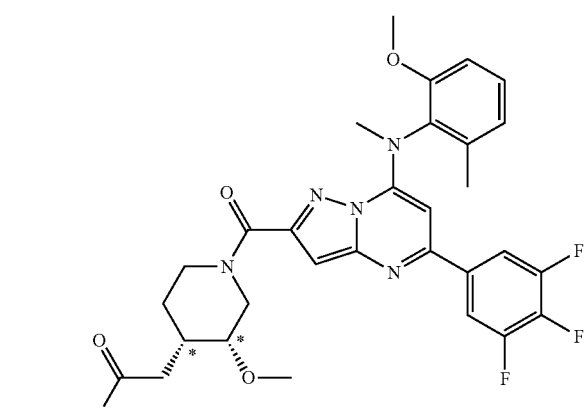

(VI)

(6a) Synthesis of 2-((3R*,4S*)-3-methoxy-1-(7-((2-methoxy-6-methylphenyl(methyl)amino)-5-(3,4,5-trifluorophenyl)pyrazolo[1,5-a]pyrimidine-2-carbonyl)piperidin-4-yl)acetic acid ethyl ester HOBT (46 mg), WSC (58 mg), 2-((3R*,4S*)-3-methoxypiperidin-4-yl)acetic acid ethyl ester hydrochloride (62 mg) (Production Example 2) and triethylamine (81 mg) were added sequentially to a solution of 7-((2-methoxy-6-methylphenyl)(methyl)amino)-5-(3,4,5-trifluorophenyl) pyrazolo[1,5-a]pyrimidine-2-carboxylic acid (88 mg) (Example 5-(5d)) in DMF (5 mL) and stirred at room temperature for 3 hours. Ethyl acetate (50 mL) and water (20 mL) were added to the reaction mixture, and the organic layer was washed with water (20 mL×2) and dried over anhydrous magnesium sulfate. The drying agent was filtered off and the filtrate was concentrated under reduced pressure. The residue was purified by silica gel column chromatography (heptane-ethyl acetate system), to obtain the title compound (111 mg) as a white solid.

$^1$H-NMR (500 MHz, CDCl$_3$, mixture of rotamers) δ: 1.27 (m, 3H), 1.28-1.75 (m, 2H), 2.15-2.30 (m, 1H), 2.15-2.34 (m, 3H), 2.40-2.55 (m, 1H), 2.60-3.15 (m, 4H), 3.35-3.44 (m, 3H), 3.52-3.80 (m, 6H), 4.11-4.20 (m, 2H), 4.20-4.96 (m, 2H), 6.22 (br.s, 1H), 6.68-6.97 (m, 3H), 7.16-7.34 (m, 1H), 7.55-7.77 (m, 2H).

Mass spectrum (ESI) m/z: 626 (M+H)$^+$ (6b) Synthesis of 2-(((3R*,4S*)-3-methoxy-1-(7-((2-methoxy-6-methylphenyl)(methyl)amino)-5-(3,4,5-trifluorophenyl)pyrazolo[1,5-a]pyrimidine-2-carbonyl)piperidin-4-yl)acetic acid A 4N lithium hydroxide aqueous solution (0.089 mL) was added to a mixture of 2-((3R*,4S*)-3-methoxy-1-(7-((2-methoxy-6-methylphenyl)(methyl)amino)-5-(3,4,5-trifluorophenyl)pyrazolo[1,5-a]pyrimidine-2-carbonyl)piperidin-4-yl)acetic acid ethyl ester (111 mg), 1,4-dioxane (5 mL) and water (1 mL) and stirred at room temperature for 22 hours, DMSO (1 mL) and acetic acid (0.2 mL) were added and the reaction mixture was concentrated under reduced pressure. The residue was purified by reverse phase silica gel column chromatography (acetonitrile-water, 0.1% acetic acid system) and fractions containing the title compound were combined. The fraction was concentrated under reduced pressure to a volume of about 3 mL, the precipitate was collected by filtration, washed with water (2 mL) and dried under reduced pressure, to obtain the title compound (76 mg) as a white solid.

$^1$H-NMR (600 MHz, CDCl$_3$, 42° C., mixture of rotamers) δ: 1.33-1.77 (m, 2H), 2.10-2.16 (m, 1H), 2.23-2.25 (m, 3H), 2.32-2.39 (m, 1H), 2.49-3.15 (m, 4H), 3.41-3.45 (m, 3H), 3.53-3.78 (m, 6H), 4.22-4.93 (m, 2H), 6.02-6.38 (m, 1H), 6.73-6.96 (m, 3H), 7.21-7.24 (m, 1H), 7.56-7.73 (m, 2H).

Mass spectrum (ESI) m/z: 598 (M+H)$^+$.

$[α]_D^{20}$: −109.0° (100 mg, DMSO, 5 mL, 100 mm).

Example 7

Synthesis of (R)-3-(7-((2-fluoro-6-methoxyphenyl)(methyl)amino)-N-methyl-5-(3,4,5-trifluorophenyl)pyrazolo[1,5-a]pyrimidine-2-carboxamide)butanoic acid

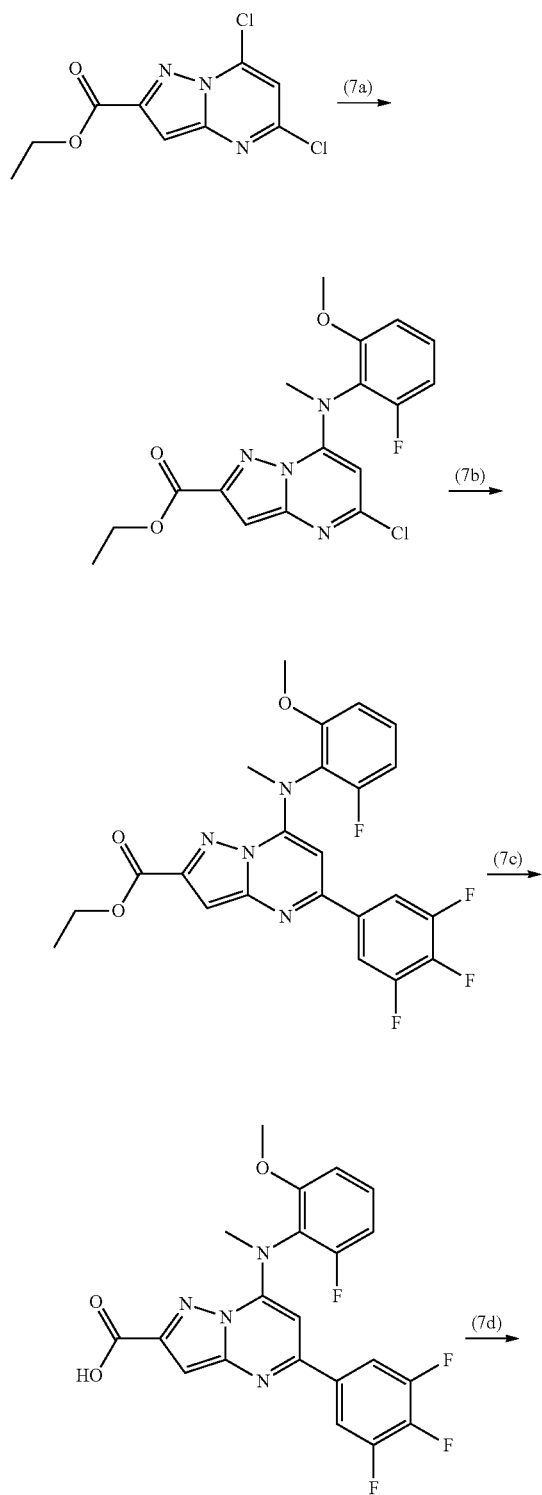

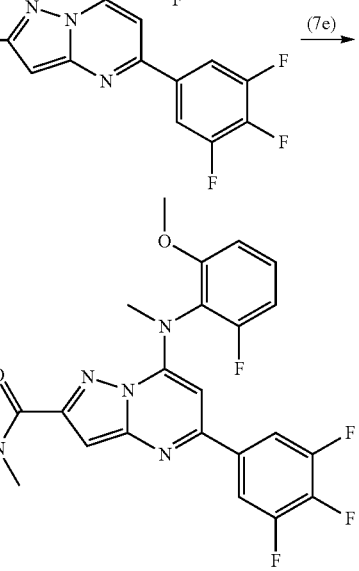

(7a) Synthesis of 5-chloro-7-((2-fluoro-6-methoxylphenyl)(methyl)amino)pyrazolo[1,5-a]pyrimidine-2-carboxylic acid ethyl ester Under a nitrogen atmosphere, a solution of 5,7-dichloropyrazolo[1,5-a]pyrimidine-2-carboxylic acid ethyl ester (CAS No. 1232224-62-2) (3.63 g) and 2-fluoro-6-methoxylaniline (CAS No. 446-61-7) (1.97 g) in NMP (2.69 mL) was stirred at 140° C. for 4 hours. After bringing back the reaction mixture to room temperature, DMF (15 mL), potassium carbonate (7.72 g) and methyl iodide (2.62 mL) were added and stirred at room temperature for 3 days. Ethyl acetate (200 mL) and water (100 mL) were added to the reaction mixture, and the organic layer was washed with water (50 mL×2) and dried over anhydrous magnesium sulfate. The drying agent was filtered off and the filtrate was concentrated under reduced pressure. The residue was purified by silica gel column chromatography (heptane-ethyl acetate system), to obtain the title compound (3.33 g).

$^1$H-NMR (400 MHz, CDCl$_3$) δ: 1.33 (t, J=7 Hz, 3H), 3.70 (br.s, 3H), 3.75 (s, 3H), 4.32 (q, J=7 Hz, 2H), 5.98 (br.s, 1H), 6.75-6.86 (m, 3H), 7.29-7.35 (m, 1H).

(7b) Synthesis of 7-(2-fluoro-6-methoxylphenyl)(methyl)amino)-5-(3,4,5-trifluorophenyl)pyrazolo[1,5-a]pyrimidine-2-carboxylic acid ethyl ester A mixture of 5-chloro-7-((2-fluoro-6-methoxylphenyl)(methyl)amino)pyrazolo[1,5-a]pyrimidine-2-carboxylic acid ethyl ester (3.33 g), 3,4,5-trifluorophenylboronic acid (1.857 g), tetrakis(triphenylphosphine)palladium (0) (0.508 g), potassium carbonate (2.431 g), water (5 mL) and 1,4-dioxane (50 mL) was stirred at 90° C. for 14 hours under a nitrogen atmosphere. The reaction mixture was concentrated under reduced pressure, ethyl acetate (400 mL) and water (200 mL) were added to the residue. The aqueous layer was extracted with ethyl acetate (200 mL), the organic layers were combined and dried over anhydrous magnesium sulfate. The drying agent was filtered off and the filtrate was concentrated under reduced pressure. The residue was purified by silica gel column chromatography (heptane-ethyl acetate system), to obtain the title compound (3.836 g).

$^1$H-NMR (500 MHz, CDCl$_3$) δ: 1.35 (t, J=7 Hz, 3H), 3.75 (s, 3H), 3.76 (s, 3H), 4.33 (q, J=7 Hz, 2H), 6.31 (br.s, 1H), 6.77-6.83 (m, 2H), 6.98 (s, 1H), 7.30-7.33 (m, 1H), 7.66 (m, 2H).
Mass spectrum (ESI) m/z: 475 (M+H)$^+$ (7c) Synthesis of 7-((2-fluoro-6-methoxylphenyl)methyl)amino)-5-(3,4,5-trifluorophenyl)pyrazolo[1,5-a]pyrimidine-2-carboxylic acid A 4N lithium hydroxide aqueous solution (1 mL) was added to a solution of 7-((2-fluoro-6-methoxylphenyl)(methyl)amino)-5-(3,4,5-trifluorophenyl)pyrazolo[1,5-a]pyrimidine-2-carboxylic acid ethyl ester (399 mg) in 1,4-dioxane (5 mL) and stirred at room temperature overnight. 2N Hydrochloric acid (2 mL) was added to the reaction mixture, which was concentrated under reduced pressure. Water was added to the residue and the deposited solid was collected by filtration, to obtain the title compound (338 mg).

$^1$H-NMR (500 MHz, CDCl$_3$) δ: 3.64 (s, 3H), 3.72 (s, 3H), 6.56 (s, 1H), 6.77 (d, J=8 Hz, 1H), 6.83 (t, J=8 Hz, 1H), 7.04 (s, 1H), 7.34-7.39 (m, 1H), 7.74 (m, 2H).
Mass spectrum (ESI) m/z: 447 (M+H)$^+$ (7d) Synthesis of (R)-3-(7-((2-fluoro-6-methoxyphenyl)methyl)amino)-N-methyl-5-(3,4,5-trifluorophenyl)pyrazolo[1,5-a]pyrimidine-2-carboxamide)butanoic acid methyl ester Triethylamine (0.66 mL) was added to a solution of 7-((2-fluoro-6-methoxyphenyl)(methyl)amino)-5-(3,4,5-trifluorophenyl)pyrazolo[1,5-a]pyrimidine-2-carboxylic acid (700 mg), (R)-3-(methylamino)butanoic acid methyl ester hydrochloride (263 mg) (Production Example 3), WSC (451 mg) and HOBT (360 mg) in DMF (10 mL) and stirred at room temperature for 4 hours. Ethyl acetate and water were added to the reaction mixture, and the organic layer was washed sequentially with water and saturated saline and dried over anhydrous magnesium sulfate. The drying agent was filtered off and the filtrate was concentrated under reduced pressure. The residue was purified by silica gel column chromatography (heptane-ethyl acetate system), to obtain the title compound (554 mg). The obtained compound was further purified using a CHIRALPAK. OD-H column under the following conditions, to obtain the title compound (0.465 g).
HPLC Conditions
Column: CHIRALPAK OD-H (Lot: ODH-0CJ-EL007), 25 mm×300 mm;
Mobile phase; hexane:ethanol=65:35;
Elution rate: 20 mL/min;
Concentration: 100 mg/mL;
Injection amount: 0.30 mL;
HPLC retention time: 11.5 min.

$^1$H-NMR (500 MHz, CDCl$_3$, mixture of rotamers) δ: 1.10 (d, J=7 Hz, 1.5H), 1.22 (d, J=7 Hz, 1.5H), 2.30 (dd, J=15, 7 Hz, 0.5H), 2.48 (dd, J=15, 7 Hz, 0.5H), 2.50 (dd, J=15, 7 Hz, 0.5H), 2.60 (dd, J=15, 7 Hz, 0.5H), 2.68 (s, 1.5H), 2.89 (s, 1.5H), 3.56-3.70 (m, 9H), 4.83 (m, 0.5H), 5.04 (m, 0.5H), 6.37 (s, 0.5H), 6.48 (s, 0.5H), 6.70 (dd, J=9, 4 Hz, 1H), 6.77 (q, J=9 Hz, 1H), 6.86 (s, 0.5H), 6.95 (s, 0.5H), 7.22-7.28 (m, 1H), 7.67-7.75 (m, 2H).

(7e) Synthesis of (R)-3-(7-((2-fluoro-6-methoxyphenyl)methyl)amino)-N-methyl-5-(3,4,5-trifluorophenyl)pyrazolo[1,5-a]pyrimidine-2-carboxamide)butanoic acid (R)-3-(7-((2-fluoro-6-methoxylphenyl)(methyl)amino)-N-methyl-5-(3,4,5-trifluorophenyl)pyrazolo[1,5-a]pyrimidine-2-carboxamide)butanoic acid methyl ester (465 mg) was dissolved in 1,4-dioxane (7 mL), a 4N lithium hydroxide aqueous solution (0.3 ml) and water (0.75 mL) were added and stirred at room temperature overnight. Further, a 1N lithium hydroxide aqueous solution (0.05 mL) was added, stirred at room temperature overnight, subsequently 1N hydrochloric acid (2 mL) was added to the reaction mixture, which was extracted with ethyl acetate. The organic layer was dried, concentrated under reduced pressure and the residue was purified by reverse phase high performance liquid chromatography (acetonitrile-water, 0.1% acetic acid system), to obtain the title compound (402 mg).

$^1$H-NMR (500 MHz, CD$_3$OD) δ: 1.06 (d, J=7 Hz, 1.5H), 1.20 (d, J=7 Hz, 1.5H), 2.29 (dd, J=16, 6 Hz, 0.5H), 2.47 (dd, J=16, 6 Hz, 0.5H), 2.50 (dd, J=16, 6 Hz, 0.5H), 2.57 (dd, J=16, 6 Hz, 0.5H), 2.64 (s, 1.5H), 2.87 (s, 1.5H), 3.58 (s, 1.5H), 3.60 (s, 1.5H), 3.62 (s, 1.5H), 3.68 (s, 1.5H), 4.62 (m, 0.5H), 4.98 (m, 0.5H), 6.75-6.94 (m, 4H), 7.31 (m, 1H), 8.00 (m, 2H).
Mass spectrum (ESI) m/z: 546 (M+H)$^+$ Example 8

Synthesis of 2-((1α,5α,6α)-3-(5-(4-chloro-3,5-difluorophenyl)-7-(isobutyl)((R)-3-methylbutan-2-yl)amino)pyrazolo[1,5-a]pyrimidine-2-carbonyl)-3-azabicyclo[3.1.0]hexan-6-yl)acetic acid

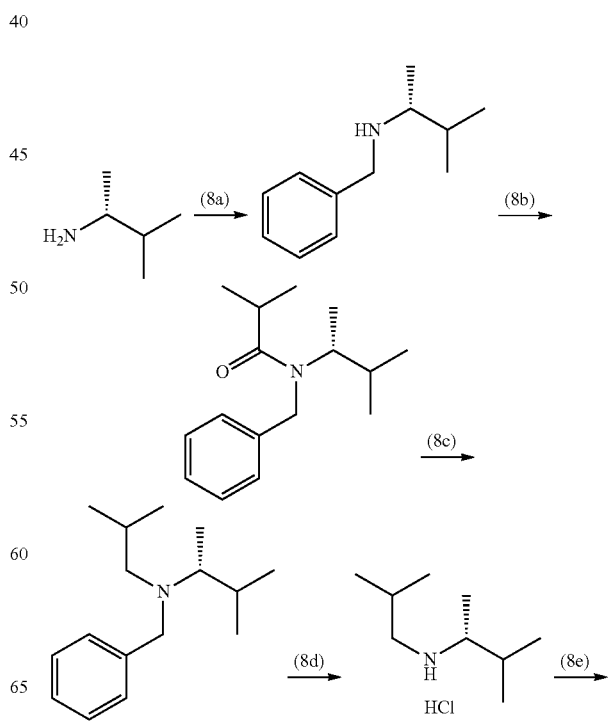

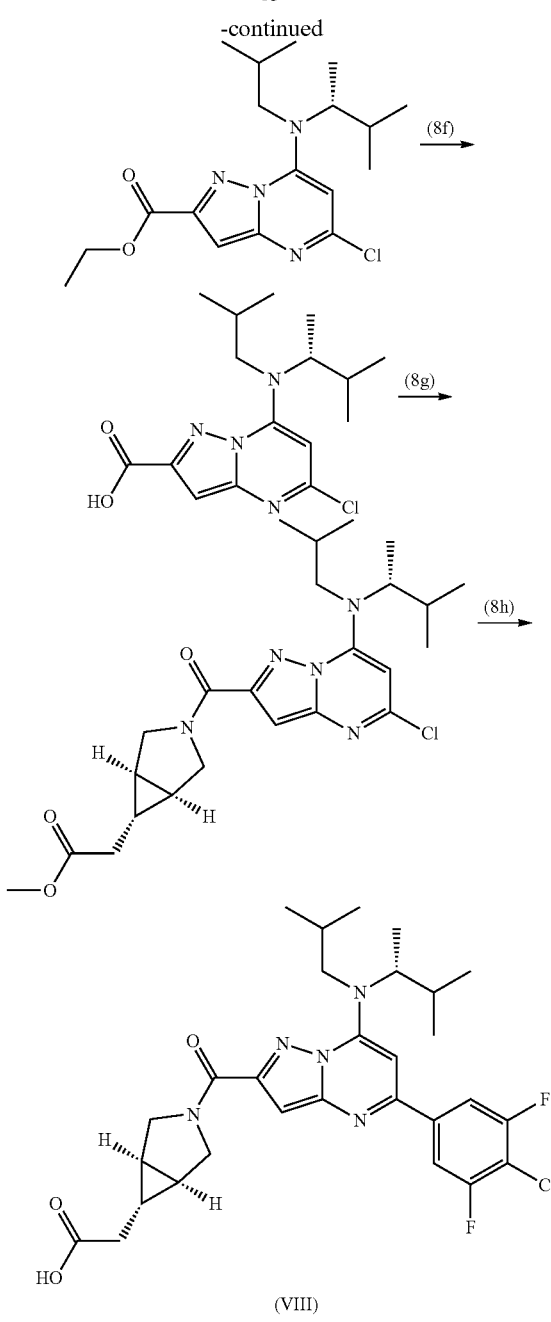

concentrated under reduced pressure. The residue was purified by NH silica gel column chromatography (heptane-ethyl acetate system), to obtain the title compound (8.76 g).

$^1$H-NMR (400 MHz, DMSO-d$_6$) δ: 0.82 (d, J=7 Hz, 3H), 0.83 (d, J=7 Hz, 3H), 0.89 (d, J=6 Hz, 3H), 1.60-1.75 (m, 2H), 2.30-2.42 (m, 1H), 3.64 (br.d, J=14 Hz, 1H), 3.73 (br.d, J=14 Hz, 1H), 7.15-7.36 (m, 5H).

(8b) Synthesis of (R)—N-benzyl-N-(3-methylbutan-2-yl)isobutylamide

Isobutyryl chloride (6 mL) was added at 0° C. to a mixture of (R)—N-benzyl-3-methylbutan-2-amine (8.64 g), dichloromethane (200 mL) and triethylamine (13 mL) and stirred for 35 minutes. Ethyl acetate and a saturated sodium hydrogen carbonate aqueous solution were added to the reaction mixture, and the organic layer was washed with water, saturated saline and dried over anhydrous sodium sulfate. The drying agent was filtered off and the filtrate was concentrated under reduced pressure. The residue was purified by silica gel column chromatography (heptane-ethyl acetate system), to obtain the title compound (11.202 g).

$^1$H-NMR (400 MHz, DMSO-d$_6$, mixture of rotamers) δ: 0.70-1.10 (m, 15H), 1.73-1.85 (m, 1H), 2.96-3.08 (m, 0.5H), 3.60-3.72 (m, 0.5H), 4.10-4.22 (m, 1H), 4.45 (d, J=16 Hz, 1H), 4.58 (d, J=16 Hz, 1H), 7.11-7.39 (m, 5H).

(8c) Synthesis of (R)—N-benzyl-N-isobutyl-3-methylbutan-2-amine (R)—N-benzyl-N-(3-methylbutan-2-yl)isobutyl amide (11.2 g) was added at 0° C. to a mixture of THF (200 mL) and lithium aluminium hydride (3.5 g) and stirred at 90° C. for 1 hour and 15 minutes. After bringing back the reaction mixture to room temperature, water (3.5 mL), a 2N sodium hydroxide aqueous solution (3.5 mL), water (10.5 mL) and anhydrous sodium sulfate were added sequentially to the reaction mixture and stirred for 1 hour and 55 minutes. The insoluble matter was filtered off, washed with ethyl acetate and the filtrate was concentrated under reduced pressure. The residue was purified by silica gel column chromatography (heptane-ethyl acetate system), to obtain the title compound (10.872 g).

$^1$H-NMR (400 MHz, DMSO-d$_6$) δ: 0.72-0.98 (m, 15H), 1.53-1.72 (m, 2H), 1.95-2.02 (m, 1H), 2.11-2.23 (m, 2H), 3.21 (d, J=14 Hz, 1H), 3.70 (d, J=14 Hz, 1H), 7.15-7.38 (m, 5H).

(8d) Synthesis of (R)—N-isobutyl-3-methylbutan-2-amine hydrochloride

10% Palladium-carbon powder (51% water content) (50 mg) was added to a mixture of (R)—N-benzyl-N-isobutyl-3-methylbutan-2-amine (2 g) and methanol (35 mL) and stirred at room temperature for 2 hours and 30 minutes under a hydrogen atmosphere. Insoluble matter was filtered off and washed with methanol and ethyl acetate. A 4N hydrogen chloride ethyl acetate solution (10 mL) was added to the filtrate and the mixture was concentrated under reduced pressure. 50% Diethyl ether-heptane (100 mL) was added to the residue, sonicated and subsequently concentrated under reduced pressure. The procedure was repeated 4 times. The obtained solid was dried under reduced pressure, to obtain the title compound (1.323 g).

$^1$H-NMR (400 MHz, DMSO-d$_6$) δ: 0.90 (d, J=7 Hz, 3H), 0.92 (d, J=7 Hz, 3H), 0.96 (d, J=7 Hz, 3H), 0.97 (d, J=7 Hz, (8a) Synthesis of (R)—N-benzyl-3-methylbutan-2-amine A mixture of (R)-(−)-3-methyl-2-butylamine (CAS No. 34701-33-2) (4.79 g), THF (150 mL), benzaldehyde (5 mL) and acetic acid (5 mL) was stirred at room temperature for 30 minutes. Sodium triacetoxyborohydride (15 g) was added thereto and stirred at room temperature for 14 hours and 40 minutes. Ethyl acetate and a saturated sodium hydrogen carbonate aqueous solution were added to the reaction mixture and stirred at room temperature for 30 minutes. The organic layer was washed sequentially with a saturated sodium hydrogen carbonate aqueous solution, water and saturated saline and dried over anhydrous sodium sulfate. The drying agent was filtered off and the filtrate was 3H), 1.14 (d, J=7 Hz, 3H), 1.95-2.20 (m, 2H), 2.65-2.80 (m, 2H), 3.00-3.09 (m, 1H), 8.28 (br.s, 1H), 8.65 (br.s, 1H).

(8e) Synthesis of (R)-5-chloro-7-(isobutyl(3-methylbutan-2-yl)amino)pyrazolo[1,5-a]pyrimidine-2-carboxylic acid ethyl ester Triethylamine (10 mL) was added to a mixture of 5,7-dichloropyrazolo[1,5-a]pyrimidine-2-carboxylic acid ethyl ester (CAS No. 1232224-62-2) (4.5 g), (R)—N-isobutyl-3-methylbutan-2-amine hydrochloride (3.588 g) and THF (70 mL) and stirred for 31 hours and 40 minutes under reflux. Ethyl acetate and water were added to the reaction mixture, and the organic layer was washed with saturated saline and dried over anhydrous sodium sulfate. The drying agent was filtered off and the filtrate was concentrated under reduced pressure. The residue was purified by NH silica gel column chromatography (heptane-ethyl acetate system), to obtain the title compound (5.05 g).

$^1$H-NMR (400 MHz, DMSO-d$_6$) δ: 0.77 (d, J=6 Hz, 3H), 0.78 (d, J=7 Hz, 3H), 0.87 (d, J=6 Hz, 3H), 0.89 (d, J=6 Hz, 3H), 1.34 (td, J=7, 1 Hz, 3H), 1.39 (d, J=7 Hz, 3H), 1.74-2.00 (m, 2H), 2.95-3.08 (m, 1H), 3.67-3.77 (m, 1H), 4.30-4.40 (m, 1H), 4.36 (q, J=7 Hz, 2H), 6.66 (s, 1H), 6.89 (s, 1H).

(8f) Synthesis of (R)-5-chloro-7-(isobutyl(3-methylbutan-2-yl)amino)pyrazolo[1,5-a]pyrimidine-2-carboxylic acid A 5N sodium hydroxide aqueous solution (5 mL) was added to a mixture of (R)-5-chloro-7-(isobutyl(3-methylbutan-2-yl)amino)pyrazolo[1,5-a]pyrimidine-2-carboxylic acid ethyl ester (1.9 g) and ethanol (25 mL) and stirred at room temperature for 20 minutes. 5N Hydrochloric acid (5 mL) and water were added to the reaction mixture and sonicated. The produced solid was collected by filtration, washed with water and dried under reduced pressure, to obtain the title compound (1.624 g).

$^1$H-NMR (400 MHz, DMSO-d$_6$) δ: 0.75 (d, J=7 Hz, 3H), 0.77 (d, J=7 Hz, 3H), 0.86 (d, J=7 Hz, 3H), 0.88 (d, J=7 Hz, 3H), 1.39 (d, J=6 Hz, 3H), 1.75-1.99 (m, 2H), 2.95-3.05 (dd, J=15, 10 Hz, 1H), 3.67-3.78 (m, 1H), 4.30-4.43 (m, 1H), 6.62 (s, 1H), 6.84 (s, 1H), 13.32 (br.s, 1H).

(8g) Synthesis of 2-((1α,5α,6α)-3-(5-chloro-7-(isobutyl(((R)-3-methylbutan-2-yl)amino)pyrazolo[1,5-a]pyrimidine-2-carbonyl)-3-azabicyclo[3.1.0]hexan-6-yl)acetic acid methyl ester Triethylamine (3 mL) was added to a mixture of (R)-5-chloro-7-(isobutyl(3-methylbutan-2-yl)amino)pyrazolo[1,5-a]pyrimidine-2-carboxylic acid (1.620 g), 2-((1α,5α,6α)-3-azabicyclo[3.1.0]hexan-6-yl)acetic acid methyl ester hydrochloride (1 g) (Production Example 4), WSC (1.4 g), HOBT (1 g) and DMF (25 mL) and stirred at room temperature for 24 hours. Ethyl acetate and water were added to the reaction mixture, and the organic layer was washed with saturated saline and dried over anhydrous sodium sulfate. The drying agent was filtered off and the filtrate was concentrated under reduced pressure. The residue was purified by silica gel column chromatography (heptane-ethyl acetate system), to obtain the title compound (1.844 g).

$^1$H-NMR (400 MHz, DMSO-d$_6$, mixture of rotamers) δ: 0.65-0.94 (m, 13H), 1.41 (d, J=7 Hz, 3H), 1.48-1.62 (m, 2H), 1.80-2.00 (m, 2H), 2.22-2.45 (m, 2H), 2.93-3.05 (m, 1H), 3.46-3.56 (m, 1H), 3.58 (s, 3H), 3.65-3.78 (m, 1H), 3.82-3.93 (m, 2H), 4.17-4.25 (m, 1H), 4.40-4.55 (m, 1H), 6.58 (s, 0.5H), 6.59 (s, 0.5H), 6.73 (s, 0.5H), 6.74 (s, 0.5H).

(8h) Synthesis of 2-((1α,5α,6α)-3-(5-(4-chloro-3,5-difluorophenyl)-7-(isobutyl((R)-3-methylbutan-2-yl)amino)pyrazolo[1,5-a]pyrimidine-2-carbonyl)-3-azabicyclo[3.1.0]hexan-6-yl)acetic acid 1,4-Dioxane (2 mL) and pure water (200 μL) were added to a mixture of 2-((1α,5α,6α)-3-(5-chloro-7-(isobutyl((R)-3-methylbutan-2-yl)amino)pyrazolo[1,5-a]pyrimidine-2-carbonyl)-3-azabicyclo[3.1.0]hexan-6-yl)acetic acid methyl ester (40 mg), 4-chloro-3,5-difluorophenylboronic acid (CAS No. 864759-63-7) (25 mg), tetrakis(triphenylphosphine)palladium (0) (10 mg) and potassium carbonate (25 mg) and stirred at 80° C. for 2 hours. The reaction mixture was directly concentrated under reduced pressure and the obtained residue was purified by silica gel column chromatography (heptane-ethyl acetate system), to obtain 2-((1α,5α,6α)-3-(5-(4-chloro-3,5-difluorophenyl)-7-(isobutyl((R)-3-methylbutan-2-yl)amino)pyrazolo[1,5-a]pyrimidine-2-carbonyl)-3-azabicyclo[3.1.0]hexan-6-yl)acetic acid methyl ester. The compound was dissolved in ethanol (1.5 mL), subsequently a 5N sodium hydroxide aqueous solution (100 μL) was added and stirred at room temperature for 2 hours. Subsequently, the reaction mixture was neutralized with 5N hydrochloric acid (100 μL) and concentrated under reduced pressure. The residue was purified by reverse phase silica gel column chromatography (acetonitrile-water, 0.1% acetic acid system), to obtain the title compound (32 mg).

$^1$H-NMR (400 MHz, CD$_3$OD, mixture of rotamers) δ: 0.80 (d, J=7 Hz, 3H), 0.83-0.91 (m, 4H), 0.94 (d, J=7 Hz, 1.5H), 0.95 (d, J=7 Hz, 1.5H), 0.98 (d, J=7 Hz, 1.5H), 1.00 (d, J=7 Hz, 1.5H), 1.53 (d, J=7 Hz, 3H), 1.56-1.61 (m, 1H), 1.62-1.67 (m, 1H), 1.95-2.07 (m, 2H), 2.22-2.41 (m, 2H), 3.05 (dd, J=14, 10 Hz, 1H), 3.65 (dt, J=12, 5 Hz, 1H), 3.90 (dd, J=14, 4 Hz, 1H), 4.01 (ddd, J=11, 4, 1 Hz, 1H), 4.08 (dd, J=12, 5 Hz, 1H), 4.43 (dd, J=12, 7 Hz, 1H), 4.58 (dt, J=10, 7 Hz, 1H), 6.87 (s, 1H), 6.91 (s, 1H), 7.89 (d, J=8 Hz, 2H).

Example 9

Synthesis of (R)-3-(7-(isobutyl((R)-3-methylbutan-2-yl)amino)-N-methyl-5-(3,4,5-trifluorophenyl)pyrazolo[1,5-a]pyrimidine-2-carboxamide)butanoic acid

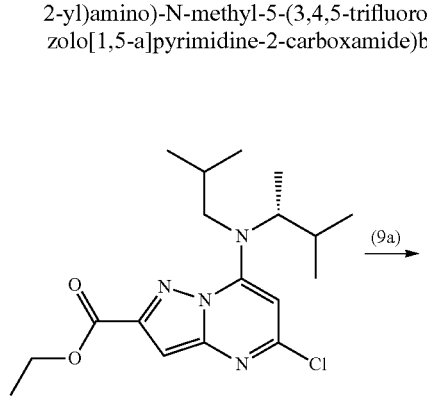

Example 8-(8e)

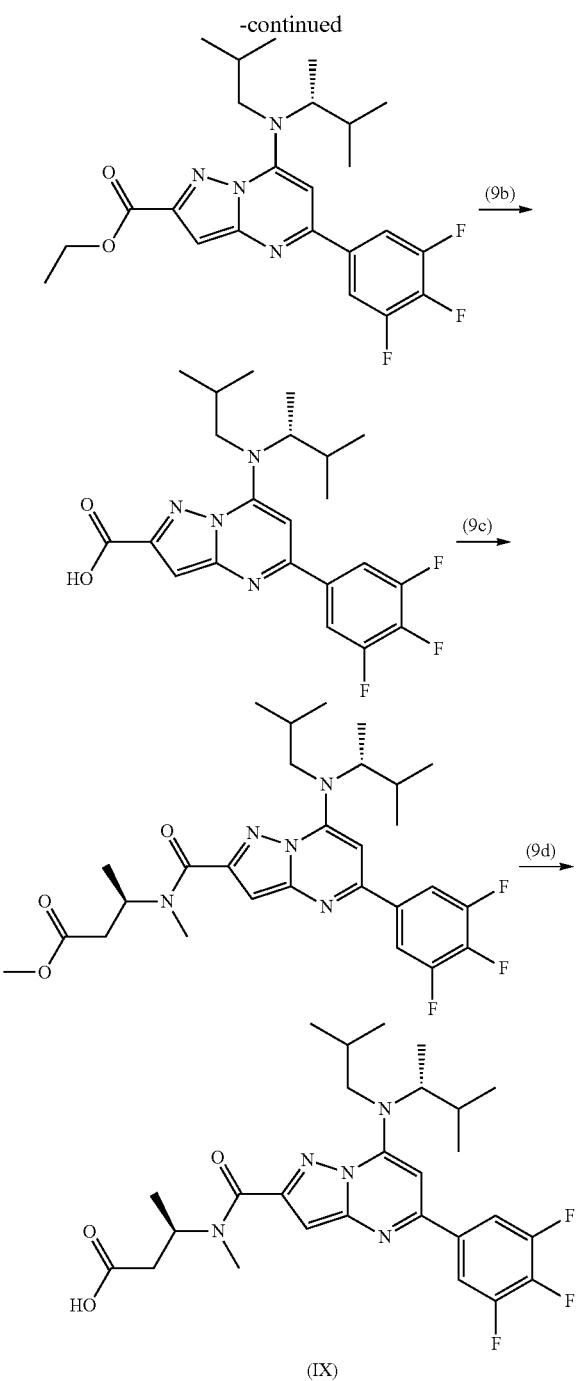

(9a) Synthesis of (R)-7-(Isobutyl(3-methylbutan-2-yl)amino)-5-(3,4,5-trifluorophenyl)pyrazolo[1,5-a]pyrimidine-2-carboxylic acid ethyl ester A mixture of (R)-5-chloro-7-(isobutyl(3-methylbutan-2-yl)amino)pyrazolo[1,5-a]pyrimidine-2-carboxylic acid ethyl ester (890 mg) (Example 8-(8e)), 3,4,5-trifluorophenylboronic acid (520 mg), tetrakis(triphenylphosphine)palladium (0) (250 mg), a 2M sodium carbonate aqueous solution (2.5 mL), ethanol (1 mL) and toluene (9 mL) was stirred at 100° C. for 19 hours 35 minutes under a nitrogen atmosphere. The reaction mixture was directly purified by silica gel column chromatography (heptane-ethyl acetate system), to obtain the title compound (955 mg).

$^1$H-NMR (400 MHz, DMSO-d$_6$) δ: 0.78 (d, J=7 Hz, 3H), 0.81 (d, J=7 Hz, 3H), 0.89 (d, J=6 Hz, 3H), 0.90 (d, J=7 Hz, 3H), 1.35 (t, J=7 Hz, 3H), 1.43 (d, J=6 Hz, 3H), 1.75-1.86 (m, 1H), 1.92-2.05 (m, 1H), 3.05 (dd, J=15, 10 Hz, 1H), 3.96 (dd, J=15, 5 Hz, 1H), 4.33 (dd, J=10, 6 Hz, 1H), 4.37 (q, J=7 Hz, 2H), 6.98 (s, 1H), 7.14 (s, 1H), 8.19 (dd, J=10, 7 Hz, 2H).

(9b) Synthesis of (R)-7-(isobutyl(3-methylbutan-2-yl)amino)-5-(3,4,5-trifluorophenyl)pyrazolo[1,5-a]pyrimidine-2-carboxylic acid A 1N lithium hydroxide aqueous solution (6 mL) was added to a solution of (R)-7-(isobutyl(3-methylbutan-2-yl)amino)-5-(3,4,5-trifluorophenyl)pyrazolo[1,5-a]pyrimidine-2-carboxylic acid ethyl ester (950 mg) in 1,4-dioxane (18 mL) and stirred at 50° C. for 1 hour. 1N Hydrochloric acid (6 mL) was added to the reaction mixture, which was diluted with ethyl acetate and washed with water and saturated saline. The organic layer was dried over anhydrous sodium sulfate, the drying agent was filtered off and the filtrate was concentrated under reduced pressure. A crude product (863 mg) of the title compound was obtained as a yellow solid.

$^1$H-NMR (400 MHz, DMSO-d$_6$) δ: 0.78 (d, J=6 Hz, 3H), 0.79 (d, J=6 Hz, 3H), 0.88 (d, J=6 Hz, 3H), 0.90 (d, J=6 Hz, 3H), 1.43 (d, J=6 Hz, 3H), 1.74-1.87 (m, 1H), 1.92-2.05 (m, 1H), 3.04 (dd, J=14, 10 Hz, 1H), 3.98 (dd, J=14, 4 Hz, 1H), 4.36 (dd, J=10, 6 Hz, 1H), 6.93 (s, 1H), 7.12 (s, 1H), 8.19 (dd, J=10, 7 Hz, 2H), 13.27 (br.s, 1H).

(9c) Synthesis of (R)-3-(7-(isobutyl((R)-3-methylbutan-2-yl)amino-N-methyl-5-(3,4,5-trifluorophenyl)pyrazolo[1,5-a]pyrimidine-2-carboxamide)butanoic acid methyl ester Triethylamine (0.07 mL) was added to a solution of (R)-7-(isobutyl(3-methylbutan-2-yl)amino)-5-(3,4,5-trifluorophenyl)pyrazolo[1,5-a]pyrimidine-2-carboxylic acid (19.6 mg), (R)-3-(methylamino)butanoic acid methyl ester hydrochloride (10 mg) (Production Example 3), WSC (10 mg) and HOBT (10 mg) in DMF (0.5 mL) and stirred at room temperature overnight. Ethyl acetate and water were added to the reaction mixture, and the organic layer was washed sequentially with water and saturated saline and dried over anhydrous magnesium sulfate. The drying agent was filtered off and the filtrate was concentrated under reduced pressure. The residue was purified by silica gel column chromatography (heptane-ethyl acetate system), to obtain a crude product of the title compound (21.1 mg).

$^1$H-NMR (500 MHz, CDCl$_3$, mixture of rotamers) δ: 0.75 (m, 3H), 0.88 (m, 6H), 0.98 (m, 3H), 1.36 (m, 3H), 1.44 (d, J=7 Hz, 3H), 1.92 (m, 1H), 1.98 (m, 1H), 2.41-2.77 (m, 2H), 2.92-3.69 (m, 8H), 4.50 (m, 1H), 5.01-5.21 (m, 1H), 6.35 (m, 1H), 6.87-6.92 (m, 1H), 7.66 (m, 2H).

(9d) Synthesis of (R)-3-(7-(isobutyl((R)-3-methylbutan-2-yl)amino)-N-methyl-5-(3,4,5-trifluorophenyl)pyrazolo[1,5-a]pyrimidine-2-carboxamide)butanoic acid (R)-3-(7-(isobutyl((R)-3-methylbutan-2-yl)amino)-N-methyl-5-(3,4,5-trifluorophenyl)pyrazolo[1,5-a]pyrimidine-2-carboxamide)butanoic acid methyl ester (21 mg) was dissolved in ethanol (2 mL), a 1N sodium hydroxide aqueous solution (0.5 mL) was added thereto and stirred at room temperature overnight. The reaction mixture, to which 2N hydrochloric acid was added, was purified by reverse phase high performance liquid chromatography (acetonitrile-water, 0.1% acetic acid system), to obtain the title compound (11 mg).

$^1$H-NMR (500 MHz, CDCl$_3$, mixture of rotamers) δ: 0.73 (m, 3H), 0.82-0.89 (m, 6H), 0.96 (d, J=6 Hz, 3H), 1.34-1.46 (m, 3H), 1.44 (d, J=7 Hz, 3H), 1.92 (m, 1H), 1.98 (m, 1H), 2.41-2.77 (m, 2H), 2.93 (m, 1H), 3.03 (s, 1.7H), 3.28 (s, 1.3H), 3.61 (m, 1H), 4.40-5.25 (m, 2H), 6.30-6.36 (m, 1H), 6.77-6.93 (m, 1H), 7.61 (m, 2H).

Mass spectrum (ESI) m/z: 534 (M+H)$^+$

Example 10

Synthesis of 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid

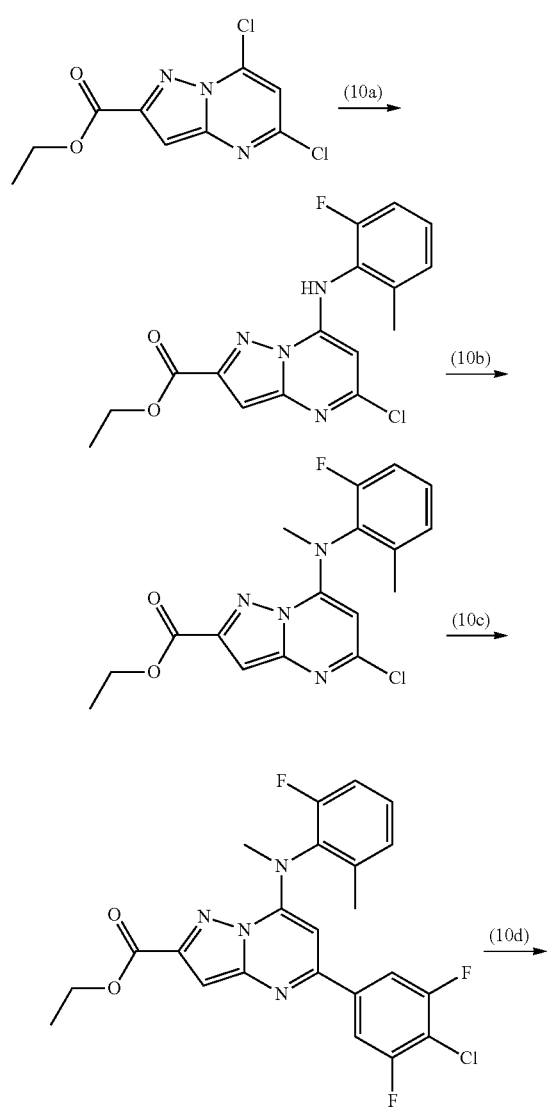

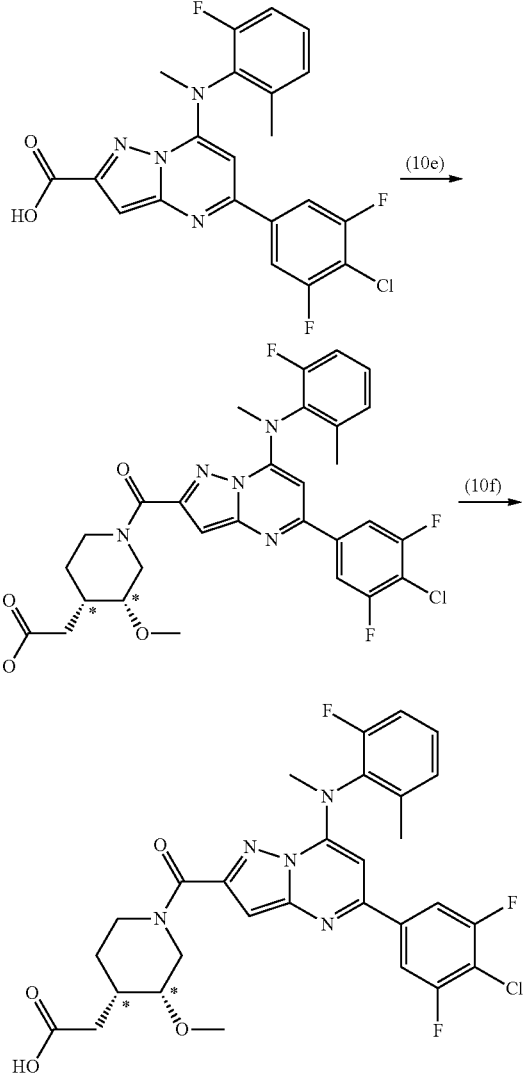

(10a) Synthesis of 5-chloro-7-((2-fluoro-6-methylphenyl)amino)pyrazolo[1,5-a]pyrimidine-2-carboxylic acid ethyl ester A solution of 5,7-dichloropyrazolo[1,5-a]pyrimidine-2-carboxylic acid ethyl ester (CAS No. 1232224-62-2) (5 g) and 2-fluoro-6-methylaniline (CAS No. 443-89-0) (2.41 g) in NMP (3 mL) was stirred at 120° C. for 4 hours. The reaction mixture was combined with a reaction solution separately obtained by stirring 5,7-dichloropyrazolo[1,5-a]pyrimidine-2-carboxylic acid ethyl ester (0.50 g) and 2-fluoro-6-methylaniline (0.27 g) in NMP (0.20 mL) at 120° C. for 4 hours, diluted with ethyl acetate, washed with water and saturated saline and dried over anhydrous sodium sulfate. After filtering off the drying agent, the filtrate was concentrated under reduced pressure, dichloromethane was added to the residue and the insoluble solid was collected by filtration, to obtain the title compound (2.88 g) as a light yellow solid. The filtrate was concentrated under reduced pressure and the residue was purified by silica gel column chromatography (hexane-ethyl acetate system), to obtain the title compound (2.28 g).

¹H-NMR (400 MHz, CDCl₃) δ: 1.46 (t, J=7 Hz, 3H), 2.34 (s, 3H), 4.50 (q, J=7 Hz, 2H), 5.75 (s, 1H), 7.02 (s, 1H), 7.12 (t, J=8 Hz, 1H), 7.18 (br.d, J=8 Hz, 1H), 7.35 (td, J=8, 6 Hz, 1H), 7.82 (br.s, 1H).

(10b) Synthesis of 5-chloro-7-((2-fluoro-6-methylphenyl)(methyl)amino)pyrazolo[1,5-a]pyrimidine-2-carboxylic acid ethyl ester Cesium carbonate (7.23 g) and methyl iodide (4.61 mL) were added to a solution of 5-chloro-7-((2-fluoro-6-methylphenyl)amino)pyrazolo[1,5-a]pyrimidine-2-carboxylic acid ethyl ester (5.16 g) in DMF (80 mL) and stirred at 50° C. for 3 hours. The reaction mixture was diluted with ethyl acetate, washed sequentially with water and saturated saline and dried over anhydrous sodium sulfate. The drying agent was filtered off and the filtrate was concentrated under reduced pressure. The residue was purified by silica gel column chromatography (heptane-ethyl acetate system), to obtain the title compound (4.64 g) as a light yellow solid.

¹H-NMR (400 MHz, CDCl₃) δ: 1.37 (t, J=7 Hz, 3H), 2.26 (s, 3H), 3.83 (br.s, 3H), 4.36 (q, J=7 Hz, 2H), 5.79 (br.s, 1H), 6.88 (s, 1H), 7.04 (t, J=9 Hz, 1H), 7.13 (d, J=8 Hz, 1H), 7.30 (td, J=9, 6 Hz, 1H).

(10c) Synthesis of 5-(4-chloro-3,5-difluorophenyl)-7-((2-fluoro-6-methylphenyl)methyl)amino)pyrazolo[1,5-a]pyrimidine-2-carboxylic acid ethyl ester Under a nitrogen atmosphere, water (2 mL), sodium carbonate (0.53 g), 4-chloro-3,5-difluorophenylboronic acid (0.44 g) and tetrakis(triphenylphosphine)palladium (0) (0.12 g) were added to a mixture of 5-chloro-7-((2-fluoro-6-methylphenyl)(methyl)amino)pyrazolo[1,5-a]pyrimidine-2-carboxylic acid ethyl ester (0.73 g) and 1,4-dioxane (16 mL) and stirred at 100° C. for 3 hours. After bringing back to room temperature, ethyl acetate (200 mL) and water (50 mL) were added to the reaction mixture, and the organic layer was separated and dried over anhydrous magnesium sulfate. The drying agent was filtered off and the filtrate was concentrated under reduced pressure. The residue was purified by silica gel column chromatography (heptane-ethyl acetate system), to obtain the title compound (0.96 g) as a light yellow solid.

¹H-NMR (400 MHz, CDCl₃) δ: 1.39 (t, J=7 Hz, 3H), 2.28 (s, 3H), 3.88 (s, 3H), 4.38 (q, J=7 Hz, 2H), 6.14 (s, 1H), 7.03 (s, 1H), 7.04 (dd, J=9, 8 Hz, 1H), 7.15 (d, J=8 Hz, 1H), 7.32 (td, J=8, 6 Hz, 1H), 7.57 (d, J=8 Hz, 2H).

(10d) Synthesis of 5-(4-chloro-3,5-difluorophenyl)-7-((2-fluoro-6-methylphenyl)(methyl)amino)pyrazolo[1,5-a]pyrimidine-2-carboxylic acid Water (10 mL) and a 4N lithium-hydroxide aqueous solution (2.47 mL) were added to a mixture of 5-(4-chloro-3,5-difluorophenyl)-7-((2-fluoro-6-methylphenyl)(methyl)amino)pyrazolo[1,5-a]pyrimidine-2-carboxylic acid ethyl ester (2.35 g) and 1,4-dioxane (100 mL) and stirred at room temperature for 17 hours, 5N Hydrochloric acid (2 mL) was added and the reaction mixture was concentrated under reduced pressure to a volume of about 15 mL. The mixture was sonicated and stirred at room temperature for 30 minutes, subsequently the solid was collected by filtration, washed with water (5 mL) and dried under reduced pressure, to obtain the title compound (2.24 g) as a light yellow solid.

¹H-NMR (400 MHz, CDCl₃) δ: 2.30 (s, 3H), 3.71 (s, 3H), 6.47 (s, 1H), 7.03 (t, J=9 Hz, 1H), 7.08 (s, 1H), 7.13-7.18 (m, 1H), 7.34 (td, J=8, 5 Hz, 1H), 7.69 (d, J=7 Hz, 2H).

(10e) Synthesis of 2-((3R*,4S*)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid ethyl ester HOBT (57 mg), WSC (72 mg), 2-((3R*,4S*)-3-methoxypiperidin-4-yl)acetic acid ethyl ester hydrochloride (77 mg) (Production Example 2) and triethylamine (101 mg) were added sequentially to a solution of 5-(4-chloro-3,5-difluorophenyl)-7-((2-fluoro-6-methylphenyl(methyl)amino)pyrazolo[1,5-a]pyrimidine-2-carboxylic acid (112 mg) in DMF (6 mL) and stirred at room temperature for 15 hours. Ethyl acetate (50 mL) and water (20 mL) were added to the reaction mixture, and the organic layer was washed with water (20 mL×2) and dried over anhydrous magnesium sulfate. The drying agent was filtered off and the filtrate was concentrated under reduced pressure. The residue was purified by silica gel column chromatography (heptane-ethyl acetate system), to obtain the title compound (137 mg).

¹H-NMR (500 MHz, CDCl₃, mixture of rotamers) δ: 1.26 (m, 3H), 1.40-1.74 (m, 2H), 2.12-2.55 (m, 5H), 2.60-3.11 (m, 4H), 3.38-3.75 (m, 6H), 4.14 (m, 2H), 4.10-4.46 (m, 1H), 4.54-4.95 (m, 1H), 6.29-6.53 (m, 1H), 6.90-7.28 (m, 4H), 7.61-7.70 (m, 2H).

(10f) Synthesis of 2-((3R*,4S*)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid An aqueous solution (1.5 mL) of lithium hydroxide (10.4 mg) was added to a solution of 2-((3R*,4S*)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid ethyl ester (137 mg) in 1,4-dioxane (6 mL) and stirred at room temperature for 20 hours. DMSO (2 mL) and acetic acid (0.1 mL) were added to the reaction mixture, which was concentrated under reduced pressure. The residue was purified by reverse phase silica gel column chromatography (acetonitrile-water, 0.1% acetic acid system), to obtain the title compound (92 mg) as a white solid.

¹H-NMR (600 MHz, CDCl₃, 30° C., mixture of rotamers) δ: 1.25-1.76 (m, 2H), 2.01-2.41 (m, 4H), 2.47-3.14 (m, 4H), 3.38-3.75 (m, 7H), 4.13-4.46 (m, 1H), 4.54-4.98 (m, 1H), 6.29-6.57 (m, 1H), 6.84-7.30 (m, 4H), 7.56-7.79 (m, 2H).

Mass spectrum (ESI) m/z: 602 (M+H)⁺.

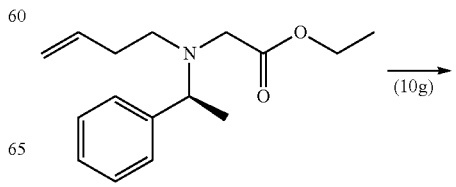

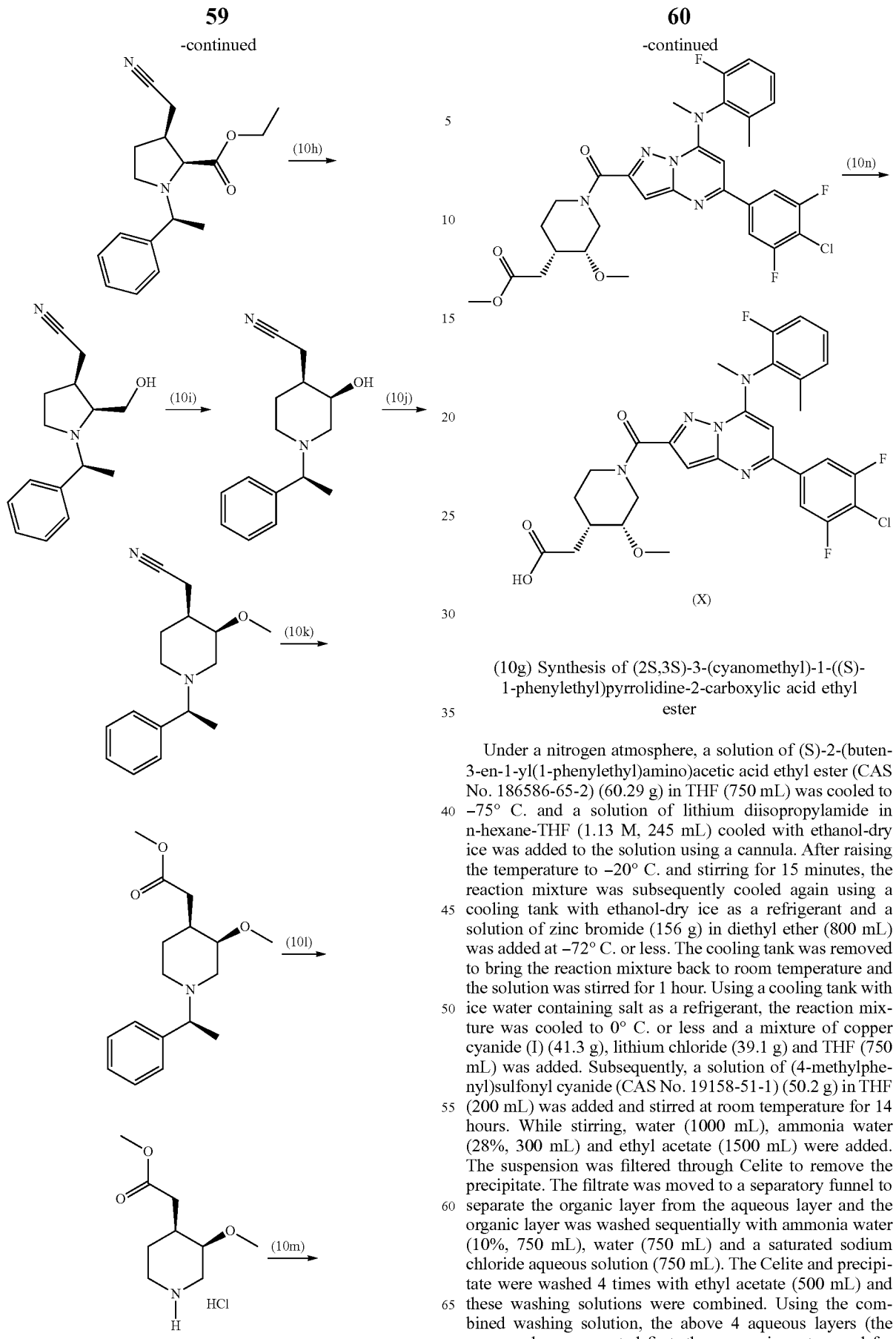

(10g) Synthesis of (2S,3S)-3-(cyanomethyl)-1-((S)-1-phenylethyl)pyrrolidine-2-carboxylic acid ethyl ester Under a nitrogen atmosphere, a solution of (S)-2-(buten-3-en-1-yl(1-phenylethyl)amino)acetic acid ethyl ester (CAS No. 186586-65-2) (60.29 g) in THF (750 mL) was cooled to −75° C. and a solution of lithium diisopropylamide in n-hexane-THF (1.13 M, 245 mL) cooled with ethanol-dry ice was added to the solution using a cannula. After raising the temperature to −20° C. and stirring for 15 minutes, the reaction mixture was subsequently cooled again using a cooling tank with ethanol-dry ice as a refrigerant and a solution of zinc bromide (156 g) in diethyl ether (800 mL) was added at −72° C. or less. The cooling tank was removed to bring the reaction mixture back to room temperature and the solution was stirred for 1 hour. Using a cooling tank with ice water containing salt as a refrigerant, the reaction mixture was cooled to 0° C. or less and a mixture of copper cyanide (I) (41.3 g), lithium chloride (39.1 g) and THF (750 mL) was added. Subsequently, a solution of (4-methylphenyl)sulfonyl cyanide (CAS No. 19158-51-1) (50.2 g) in THF (200 mL) was added and stirred at room temperature for 14 hours. While stirring, water (1000 mL), ammonia water (28%, 300 mL) and ethyl acetate (1500 mL) were added. The suspension was filtered through Celite to remove the precipitate. The filtrate was moved to a separatory funnel to separate the organic layer from the aqueous layer and the organic layer was washed sequentially with ammonia water (10%, 750 mL), water (750 mL) and a saturated sodium chloride aqueous solution (750 mL). The Celite and precipitate were washed 4 times with ethyl acetate (500 mL) and these washing solutions were combined. Using the combined washing solution, the above 4 aqueous layers (the aqueous layer separated first, the ammonia water used for washing, the water used for washing and the saturated sodium chloride aqueous solution used for washing) were sequentially extracted. The organic layers were all combined and dried over anhydrous magnesium sulfate. The drying agent was filtered off and the filtrate was concentrated under reduced pressure. The residue was purified by silica gel column chromatography (heptane-ethyl acetate system), to obtain the title compound (42.98 g).

$^1$H-NMR (400 MHz, CDCl$_3$, major isomer) δ: 1.24 (t, J=7 Hz, 3H), 1.36 (d, J=7 Hz, 3H), 1.77 (m, 1H), 2.18 (m, 1H), 2.27 (dd, J=17, 9 Hz, 1H), 2.35 (dd, J=17, 7 Hz, 1H), 2.66 (m, 1H), 2.95 (q, J=8 Hz, 1H), 3.10 (td, J=9, 3 Hz, 1H), 3.42 (d, J=8 Hz, 1H), 3.75 (q, J=7 Hz, 1H), 4.09-4.18 (m, 2H), 7.22-7.38 (m, 5H).

(10h) Synthesis of 2-((2S,3S)-2-hydroxymethyl-1-((S)-1-phenylethyl)pyrrolidin-3-yl)acetonitrile Under ice cooling and a nitrogen atmosphere, lithium tetrahydroborate (20 g) was added to a solution of (2S,3S)-3-(cyanomethyl)-1-((S)-1-phenylethyl)pyrrolidine-2-carboxylic acid ethyl ester (44.74 g) in THF (700 mL) and heated to reflux for 5 hours. The reaction mixture was cooled to room temperature and was poured into a mixture of 1N hydrochloric acid (1000 mL) and ethyl acetate. The reaction mixture was stirred for 30 minutes, subsequently sodium hydrogen carbonate (about 100 g) was added and extracted with ethyl acetate 3 times and dichloromethane twice. The organic layers were combined and dried, the drying agent was filtered off and subsequently the filtrate was concentrated under reduced pressure. The residue was purified by NH silica gel column chromatography (heptane-ethyl acetate system), to obtain the title compound (28.98 g).

$^1$H-NMR (500 MHz, CDCl$_3$, major isomer) δ: 1.47 (d, J=7 Hz, 3H), 1.59 (qd, J=12, 7 Hz, 1H), 1.93 (dt, J=12, 6 Hz, 1H), 2.32-2.40 (m, 1H), 2.46-2.63 (m, 3H), 3.01 (dd, J=9, 8 Hz, 1H), 3.08-3.10 (m, 1H), 3.27 (d, J=11 Hz, 1H), 3.55 (dd, J=12, 2 Hz, 1H), 3.65 (dd, J=12, 4 Hz, 1H), 3.87 (q, J=7 Hz, 1H), 7.26-7.36 (m, 5H).

(10i) Synthesis of 2-((3R,4S)-3-hydroxy-1-((S)-1-phenylethyl)piperidin-4-yl)acetonitrile Under a nitrogen atmosphere, a solution of 2-((2S,3S)-2-hydroxymethyl-1-((S)-1-phenylethyl)pyrrolidin-3-yl)acetonitrile (52.44 g) in THF (2000 mL) was cooled to −74° C. or less and trifluoroacetic anhydride (36.4 mL) was added dropwise while stirring in such a way that the internal temperature did not exceed −73° C. After further stirring for 3 hours, triethylamine (120 mL) was added dropwise. After stirring for 15 minutes, the internal temperature was brought back to room temperature and the reaction mixture was heated to reflux for 15 hours. The solvent was removed under reduced pressure, ethyl acetate (5000 mL) and a 2N sodium hydroxide aqueous solution (500 mL) were added to the residue to separate the solution. The organic layer was dried over anhydrous magnesium sulfate, the drying agent was filtered off and the filtrate was concentrated under reduced pressure. The residue was purified by NH silica gel column chromatography (heptane-ethyl acetate system), to obtain the title compound (51.25 g).

$^1$H-NMR (400 MHz, CDCl$_3$, major isomer) δ: 1.37 (d, J=7 Hz, 3H), 1.47-1.76 (m, 3H), 1.95 (td, J=12, 3 Hz, 1H), 2.15 (dd, J=12, 1 Hz, 1H), 2.33 (dd, J=17, 8 Hz, 1H), 2.46 (dd, J=17, 7 Hz, 1H), 2.82-2.86 (m, 2H), 3.09-3.14 (m, 1H), 3.56 (q, J=7 Hz, 1H), 3.74 (d, J=10 Hz, 1H), 7.24-7.35 (m, 5H).

(10j) Synthesis of 2-((3R,4S)-3-methoxy-1-((S)-1-phenylethyl)piperidin-4-yl) acetonitrile Under ice cooling and a nitrogen atmosphere, sodium hydride (60%, 9.19 g) was added gradually while stirring over a period of 15 minutes to a mixture of 2-((3R,4S)-3-hydroxy-1-((S)-1-phenylethyl)piperidin-4-yl) acetonitrile (51.01 g) and THF (750 mL). After further stirring for 10 minutes, dimethyl sulfate (22.94 mL) was added dropwise. After stirring for 5 hours, a saturated ammonium chloride aqueous solution (50 mL), ammonia water (28%, 50 mL) and ethyl acetate (1000 mL) were sequentially added and stirred for 30 minutes. A 1N sodium hydroxide aqueous solution (500 mL) was added to separate the solution. The organic layer was washed with a saturated sodium chloride aqueous solution (250 mL) and the combined aqueous layers were extracted with ethyl acetate (500 mL). The organic layers were combined, dried over anhydrous magnesium sulfate, the drying agent was filtered off and the filtrate was concentrated under reduced pressure. The residue was purified by NH silica gel column chromatography (heptane-ethyl acetate system), to obtain the title compound (47.9 g).

$^1$H-NMR (400 MHz, CDCl$_3$, major isomer) δ: 1.38 (d, J=7 Hz, 3H), 1.53-1.59 (m, 1H), 1.63-1.72 (m, 1H), 1.85-1.94 (m, 1H), 2.02-2.15 (m, 2H), 2.30 (dd, J=17, 7 Hz, 1H), 2.49 (dd, J=17, 8 Hz, 1H), 2.74 (br.d, J=11 Hz, 1H), 3.04 (br.d, J=11 Hz, 1H), 3.30 (s, 3H), 3.38 (br.s, 1H), 3.55 (q, J=7 Hz, 1H), 7.23-7.33 (m, 5H).

(10k) Synthesis of 2-(3R,4S)-3-methoxy-1-((S)-1-phenylethyl)piperidin-4-yl)acetic acid methyl ester Under a nitrogen atmosphere, thionyl chloride (352 mL) was added dropwise under ice cooling to methanol (1500 mL), subsequently a solution of 2-((3R,4S)-3-methoxy-1-((S)-1-phenylethyl)piperidin-4-yl)acetonitrile (49.8 g) in methanol (50 mL) was added. The mixture was heated to reflux for 20 hours, subsequently ice cooled, and thionyl chloride (352 mL) was further added dropwise, and heated to reflux for 22 hours. The reaction mixture was ice cooled again, and thionyl chloride (50 mL) was further added dropwise, and heated to reflux for 62 hours. The reaction mixture, after brought back to room temperature, was concentrated under reduced pressure. The residue was dissolved in water (250 mL) and ethyl acetate (250 mL), ammonia water (28%, 50 mL) was added and subsequently a 2N sodium hydroxide aqueous solution was added until pH 11 was achieved. The solution was separated, the aqueous layer was extracted with ethyl acetate (500 mL), the organic layers were combined and dried over anhydrous magnesium sulfate, the drying agent was filtered off and the filtrate was concentrated under reduced pressure, to obtain a residue A.

Next, the aqueous layer was concentrated under reduced pressure and methanol (1000 mL) and concentrated sulfuric acid (50 mL) were added to the residue and heated to reflux for 22 hours. The reaction mixture was brought back to room temperature and adjusted to pH 8 with sodium hydrogen carbonate. The solvent was removed under reduced pressure, the residue was dissolved in ethyl acetate (1000 mL) and water (250 mL), pH was adjusted to 11 using a 2N sodium hydroxide aqueous solution and the solution was separated. The aqueous layer was extracted with ethyl acetate (500 mL), the organic layers were combined and dried over anhydrous magnesium sulfate, the drying agent was filtered off and the filtrate was concentrated under reduced pressure, to obtain a residue B.

Under a nitrogen atmosphere, thionyl chloride (352 mL) was added dropwise under ice cooling to methanol (1500 mL) and subsequently a solution of the residue A in methanol (100 mL) was added. The mixture was heated to reflux for 22 hours. The reaction mixture was brought back to room temperature, the solvent was removed under reduced pressure, the residue was dissolved in ethyl acetate (1000 mL) and water (250 mL), ammonia water (28%, 50 mL) was added, pH was adjusted to 11 using a 2N sodium hydroxide aqueous solution and the solution was separated. The aqueous layer was extracted with ethyl acetate (500 mL), the organic layers were combined and dried over anhydrous magnesium sulfate, the drying agent was filtered off and the filtrate was concentrated under reduced pressure, to obtain a residue C.

The aqueous layer obtained in the second reaction post-treatment was concentrated under reduced pressure, methanol (1000 mL) and concentrated sulfuric acid (50 mL) were added to the residue and heated to reflux for 22 hours. The reaction mixture was brought back to room temperature and adjusted to pH 8 with sodium hydrogen carbonate. The solvent was removed under reduced pressure, the residue was dissolved in ethyl acetate (1000 mL) and water (250 mL), pH was adjusted to 11 using a 2N sodium hydroxide aqueous solution and the solution was separated. The aqueous layer was extracted with ethyl acetate (500 mL), the organic layers were combined and dried over anhydrous magnesium sulfate, the drying agent was filtered off and the filtrate was concentrated under reduced pressure, to obtain a residue D.

The residue B, residue C and residue D were combined, purified by NH silica gel column chromatography (heptane-ethyl acetate system), to obtain crude 2-((3R,4S)-3-methoxy-1-((S)-1-phenylethyl)piperidin-4-yl)acetic acid methyl ester (52.35 g).

A 4N hydrogen chloride ethyl acetate solution (100 mL) was added with stirring to an ethyl acetate (400 mL) solution wherein crude 2-((3R,4S)-3-methoxy-1-((S)-1-phenylethyl) piperidin-4-yl) acetic acid methyl ester (1.45 g) separately obtained by the same method was combined with the crude 2-((3R,4S)-3-methoxy-1-((S)-1-phenylethyl)piperidin-4-yl) acetic acid methyl ester (52.35 g). The reaction mixture was stirred at room temperature overnight, subsequently the precipitate was collected by filtration, washed with ethyl acetate (100 mL) and dried under reduced pressure. Water (250 mL), ethyl acetate (250 mL) and a sodium hydrogen carbonate aqueous solution (250 mL) were added sequentially while stirring to the obtained solid. After further adding ethyl acetate (750 mL), pH was adjusted to 12 using potassium carbonate and the layers were separated. The aqueous layer was washed with ethyl acetate (250 mL), the washing solution and the separated organic layer were combined and dried over anhydrous magnesium sulfate, the drying agent was filtered off and the filtrate was concentrated under reduced pressure. The obtained residue (46.3 g) was dissolved in ethyl acetate (400 mL) and a 4N hydrogen chloride ethyl acetate solution (80 mL) was added while stirring. Water (250 mL) and ethyl acetate (250 mL) and sodium hydrogen carbonate were added sequentially while stirring to the solid obtained by stirring the reaction mixture at room temperature overnight, subsequently collecting the precipitate by filtration, washing with ethyl acetate (40 mL) and drying under reduced pressure. Water (750 mL) and ethyl acetate (750 mL) were added to separate the layers. A 5N sodium hydroxide aqueous solution (50 ml) was added to the aqueous layer, which was extracted with ethyl acetate (1000 mL). The organic layers were combined, dried over anhydrous magnesium sulfate, the drying agent was filtered off and the filtrate was concentrated under reduced pressure, to obtain 45.2 g of the residue. The residue was combined with 16.2 g of the residue obtained separately by the same operations, dissolved in ethyl acetate. (500 mL) and a 4N hydrogen chloride ethyl acetate solution (100 mL) was added while stirring. The reaction mixture was stirred at room temperature overnight, subsequently the precipitate was collected by filtration, washed twice with ethyl acetate (60 mL) and dried under reduced pressure. Water (800 mL) and ethyl acetate (800 mL) were added sequentially while stirring to the solid obtained, sodium hydrogen carbonate was added while stirring and the solution was separated. A 5N sodium hydroxide aqueous solution (50 mL) was added to the aqueous layer, which was extracted with ethyl acetate (800 mL). The organic layers were combined, dried over anhydrous magnesium sulfate, the drying agent was filtered off and the filtrate was concentrated under reduced pressure, to obtain the title compound (60.7 g).

$^1$H-NMR (400 MHz, CDCl$_3$) δ: 1.38 (d, J=7 Hz, 3H), 1.45-1.54 (m, 1H), 1.57-1.67 (m, 1H), 2.03-2.21 (m, 3H), 2.24 (dd, J=16, 7 Hz, 1H), 2.50 (dd, J=16, 7 Hz, 1H), 2.64 (br.s, 1H), 2.85 (br.s, 1H), 3.27 (s, 3H), 3.29-3.32 (m, 1H), 3.52 (q, J=7 Hz, 1H), 3.65 (s, 3H), 7.23-7.33 (m, 5H).

(10l) Synthesis of 2-((3R,4S)-3-methoxypiperidin-4-yl)acetic acid methyl ester hydrochloride Palladium-activated carbon (Pd10%) (0.639 g) was added to a mixture of a solution of 2-((3R,4S)-3-methoxy-1-((S)-1-phenylethyl)piperidin-4-yl) acetic acid methyl ester (4.37 g) in methanol (50 mL) and a solution of hydrogen chloride in methanol (5-10%, 30 mL) and stirred at room temperature for 16 hours under a hydrogen atmosphere. Further, palladium-activated carbon (Pd10%) (0.639 g) was added and stirred at room temperature for 24 hours under a hydrogen atmosphere. Palladium-activated carbon (Pd10%) (0.639 g) was added and further stirred at room temperature for 24 hours under a hydrogen atmosphere. The mixture was filtered through Celite and the Celite was washed with methanol. The filtrate and the washing solution were combined and concentrated under reduced pressure, to obtain the title compound (3.81 g).

$^1$H-NMR (400 MHz, CD$_3$OD) δ: 1.71-1.85 (m, 2H), 2.16-2.25 (m, 1H), 2.25 (dd, J=16, 7 Hz, 1H), 2.53 (dd, J=16, 7 Hz, 1H), 3.00-3.06 (ms 2H), 3.27 (m, 1H), 3.40 (s, 3H), 3.59-3.63 (m, 2H), 3.67 (s, 3H).

(10m) Synthesis of 2-((3R,4S)-1-(5-(4-chloro-3,5-difluorophenyl)-7-((2-fluoro-6-methylphenyl) (methyl)amino)pyrazolo[1,5-a]pyrimidine-2-carbonyl)-3-methoxypiperidin-4-yl)acetic acid methyl ester HOBT (2.280 g) and WSC (3.23 g) were added to a solution of 5-(4-chloro-3,5-difluorophenyl)-7-((2-fluoro-6-methylphenyl(methyl)amino)pyrazolo[1,5-a]pyrimidine-2-carboxylic acid (6.03 g) (Example 10-(10d)) in DMF (100 mL), stirred for 15 minutes, subsequently a solution of 2-((3R,4S)-3-methoxypiperidin-4-yl)acetic acid methyl ester hydrochloride (3.36 g) in DMF (50 mL) and triethylamine (5.64 mL) were added sequentially and stirred at room temperature for 3 hours. Ethyl acetate (700 mL) and water (500 mL) were added to the reaction mixture, and the organic layer was washed twice with water (750 mL) containing a small amount of sodium chloride. The aqueous layer and washing solutions were sequentially extracted with ethyl acetate (750 mL), the organic layers were combined and dried over anhydrous magnesium sulfate. The drying agent was filtered off and the filtrate was concentrated under reduced pressure. The residue was purified by silica gel column chromatography (heptane-ethyl acetate system), to obtain the title compound (5.83 g).

¹H-NMR (400 MHz, CDCl₃, mixture of rotamers) δ: 1.25-1.75 (m, 2H), 2.05-2.95 (m, 9H), 3.38-3.75 (m, 9H), 4.10-4.46 (m, 1H), 4.54-4.95 (m, 1H), 6.37-6.50 (m, 1H), 6.90-7.28 (m, 4H), 7.64-7.76 (m, 2H).

(10n) Synthesis of 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl) acetic acid Water (30 mL) and a 4N lithium hydroxide aqueous solution (3.49 mL) were added to a solution of 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid methyl ester (5.73 g) in 1,4-dioxane (150 mL) and stirred at room temperature for 14 hours. DMSO (10 mL) and formic acid (3 mL) were added to the reaction mixture, which was concentrated under reduced pressure. The residue was purified by reverse phase silica gel column chromatography (acetonitrile-water, 0.1% acetic acid system), to obtain the title compound (5.124 g) as a solid.

¹H-NMR (500 MHz, CD₃OD, mixture of rotamers) δ: 1.24-1.60 (m, 2H), 2.00-2.47 (m, 4H), 2.48-3.12 (m, 4H), 3.31-3.64 (m, 7H), 4.00-4.34 (m, 1H), 4.34-4.65 (m, 1H), 6.84-6.87 (m, 1H), 6.90-7.35 (m, 4H), 7.98-8.01 (m, 2H).

$[\alpha]_D^{20}$: −109.9° (100 mg, DMSO, 5 mL, 100 mm).

Example 11

Synthesis of 2-(((3R*,4S*)-1-(5-(4-chloro-3-fluorophenyl)-7-((2-chloro-6-methylphenyl)(methyl)amino)pyrazolo[1,5-a]pyrimidine-2-carbonyl)-3-methoxypiperidin-4-yl)acetic acid

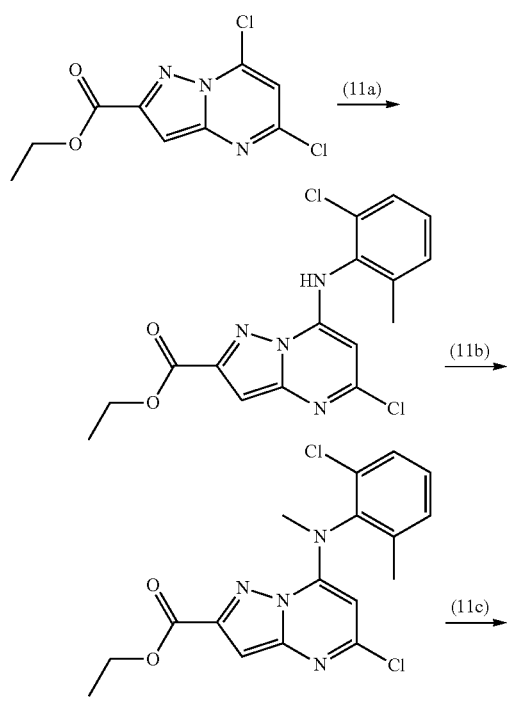

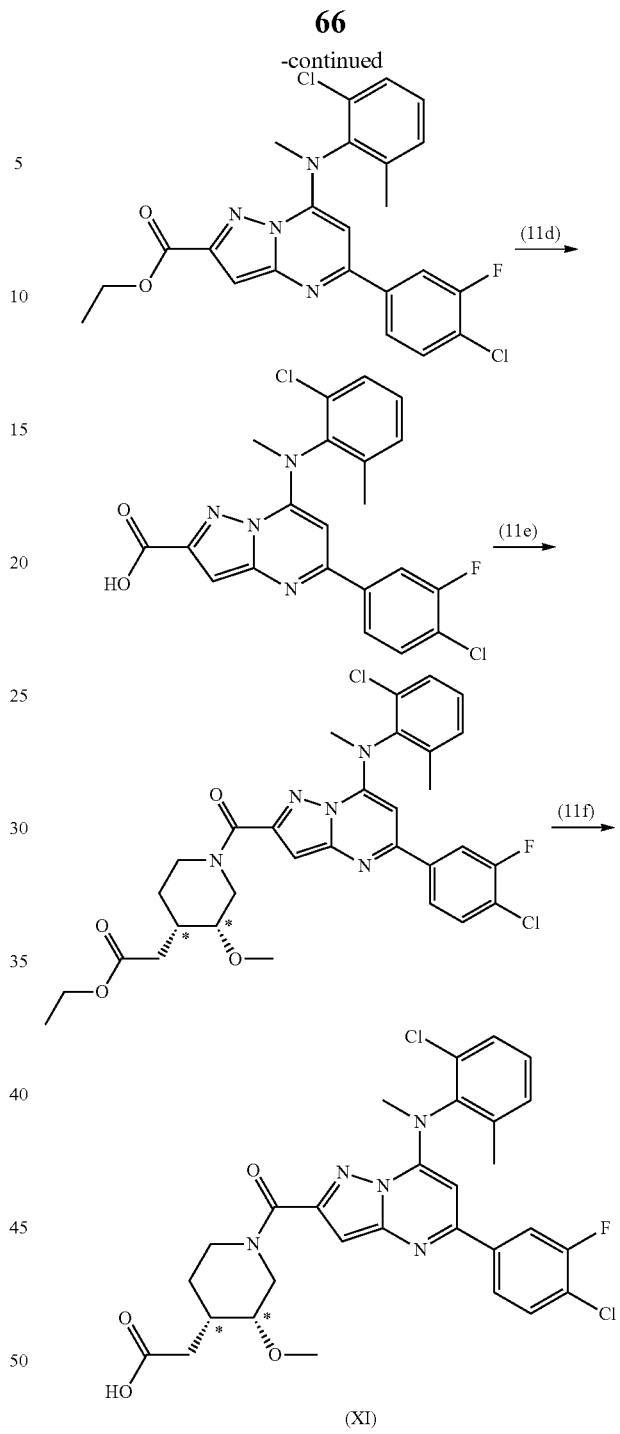

(11a) Synthesis of 5-chloro-7-((2-chloro-6-methylphenyl)amino)pyrazolo[1,5-a]pyrimidine-2-carboxylic acid ethyl ester A solution of 5,7-dichloropyrazolo[1,5-a]pyrimidine-2-carboxylic acid ethyl ester (CAS No. 1232224-62-2) (2.9 g) and 2-chloro-6-methylaniline (CAS No. 87-63-8) (1.6 g) in NMP (1.1 mL) was stirred at 140° C. for 4 hours. The reaction mixture was cooled, subsequently diluted with ethyl acetate, the precipitate was collected by filtration and washed with diethyl ether. A saturated aqueous solution of sodium hydrogen carbonate was added to the filtrate and the aqueous layer was extracted with ethyl acetate. The organic layers were combined and dried over anhydrous sodium sulfate. After filtering off the drying agent, the filtrate was concentrated under reduced pressure and the residue was purified by silica gel column chromatography (hexane-ethyl acetate system), to obtain the title compound (3.44 g).

$^1$H-NMR (400 MHz, CDCl$_3$) δ: 1.47 (t, J=7 Hz, 3H), 2.33 (s, 3H), 4.51 (q, J=7 Hz, 2H), 5.65 (s, 1H), 7.02 (s, 1H), 7.30 (dd, J=8, 2 Hz, 1H), 7.34 (t, J=8 Hz, 1H), 7.44 (dd, J=8, 2 Hz, 1H), 7.98 (br.s, 1H).

(11b) Synthesis of 5-chloro-7-((2-chloro-6-methylphenyl)(methyl)amino)pyrazolo[1,5-a]pyrimidine-2-carboxylic acid ethyl ester Potassium carbonate (1.14 g) and methyl iodide (0.86 mL) were added to a solution of 5-chloro-7-((2-chloro-6-methylphenyl)amino)pyrazolo[1,5-a]pyrimidine-2-carboxylic acid ethyl ester (2.00 g) in DMF (50 mL) and stirred for 3 days. Ethyl acetate (300 mL) and water (100 mL) were added to the reaction mixture, and the organic layer was washed with water (2×100 mL) and dried over anhydrous magnesium sulfate. The drying agent was filtered off and the filtrate was concentrated under reduced pressure. The residue was purified by silica gel column chromatography (heptane-ethyl acetate system), to obtain the title compound (1.89 g) as a light yellow solid.

$^1$H-NMR (500 MHz, CDCl$_3$, 55° C., mixture of rotamers) δ: 1.35 (br.s, 3H), 2.27 (s, 3H), 3.83 (br.s, 3H), 4.34 (br.s, 2H), 5.68 (br.s, 1H), 6.85 (s, 1H), 7.20-7.41 (m, 3H).

(11c) Synthesis of 5-(4-chloro-3-fluorophenyl)-7-((2-chloro-6-methylphenyl)(methyl)amino)pyrazolo[1,5-a]pyrimidine-2-carboxylic acid ethyl ester Under a nitrogen atmosphere, water (5 mL), sodium carbonate (0.63 g), 4-chloro-3-fluorophenylboronic acid (CAS No. 137504-86-0) (0.52 g) and tetrakis(triphenylphosphine)palladium (0) (0.14 g) were added to a mixture of 5-chloro-7-((2-chloro-6-methylphenyl)(methyl)amino)pyrazolo[1,5-a]pyrimidine-2-carboxylic acid ethyl ester (0.94 g) and 1,4-dioxane (40 mL) and stirred at 90° C. for 18 hours. After bringing the reaction mixture back to room temperature, ethyl acetate (200 mL) and water (100 mL) were added to it, and the organic layer was separated and dried over anhydrous magnesium sulfate. The drying agent was filtered off and the filtrate was concentrated under reduced pressure. The residue was purified by silica gel column chromatography (heptane-ethyl acetate system), to obtain the title compound (0.99 g) as a light yellow solid.

$^1$H-NMR (500 MHz, CDCl$_3$, 55° C., mixture of rotamers) δ: 1.37 (t, J=7 Hz, 3H), 2.29 (s, 3H), 3.88 (s, 3H), 4.36 (q, J=7 Hz, 2H), 6.07 (br.s, 1H), 6.98 (s, 1H), 7.20-7.27 (m, 2H), 7.34 (m, 1H), 7.43 (t, J=8 Hz, 1H), 7.62 (br.d, J=6 Hz, 1H), 7.73 (br.d, J=10 Hz, 1H).

(11d) Synthesis of 5-(4-chloro-3-fluorophenyl)-7-((2-chloro-6-methylphenyl)(methyl)amino)pyrazolo[1,5-a]pyrimidine-2-carboxylic acid Water (5 mL) and a 4N lithium hydroxide aqueous solution (1.01 mL) were added to 5-(4-chloro-3-fluorophenyl)-7-((2-chloro-6-methylphenyl)(methyl)amino)pyrazolo[1,5-a]pyrimidine-2-carboxylic acid ethyl ester (0.96 g) and 1,4-dioxane (40 mL) and stirred at room temperature for 15 hours. Acetic acid (0.2 mL) and 5N hydrochloric acid (0.5 mL) were added and the reaction mixture was concentrated under reduced pressure to a volume of about 5 mL. The solid was collected by filtration, washed with water (5 mL) and dried under reduced pressure. The title compound (0.83 g) was obtained as a white solid.

$^1$H-NMR (500 MHz, CDCl$_3$, 55° C., mixture of rotamers) δ: 2.28 (s, 3H), 3.68 (br.s, 3H), 6.45 (br.s, 1H), 7.02 (s, 1H), 7.23-7.34 (m, 3H), 7.50 (t, J=8 Hz, 1H), 7.76 (br.s, 1H), 7.85 (br.s, 1H).

(11e) Synthesis of 2-(((3R*,4S*)-1-(5-(4-chloro-3-fluorophenyl)-7-((2-chloro-6-methylphenyl)(methyl)amino)pyrazolo[1,5-a]pyrimidine-2-carbonyl)-3-methoxypiperidin-4-yl)acetic acid ethyl ester HOBT (57 mg), WSC (72 mg), 2-((3R*,4S*)-3-methoxypiperidin-4-yl)acetic acid ethyl ester hydrochloride (77 mg) (Production Example 2) and triethylamine (101 mg) were added sequentially to a solution of 5-(4-chloro-3-fluorophenyl)-7-((2-chloro-6-methylphenyl(methyl)amino)pyrazolo[1,5-a]pyrimidine-2-carboxylic acid (111 mg) in DMF (5 mL) and stirred at room temperature for 15 hours. Ethyl acetate (50 mL) and water were added to the reaction mixture, and the organic layer was washed with water (25 mL×2) and dried over anhydrous magnesium sulfate. The drying agent was filtered off and the filtrate was concentrated under reduced pressure. The residue was purified by silica gel column chromatography (heptane-ethyl acetate system), to obtain the title compound (120 mg).

$^1$H-NMR (400 MHz, CD$_3$OD, mixture of rotamers) δ: 1.24 (m, 3H), 1.24-1.58 (m, 2H), 2.03-2.48 (m, 6H), 2.60-3.08 (m, 3H), 3.30-3.34 (m, 3H), 3.52-3.55 (m, 3H), 3.99-4.52 (m, 2H), 4.12 (q, J=7 Hz, 2H), 6.79-6.82 (m, 1H), 6.96-6.98 (m, 1H), 7.23-7.39 (m, 3H), 7.64 (t, J=8 Hz, 1H), 8.01 (d, J=8 Hz, 1H), 8.09 (d, J=8 Hz, 1H).

(11f) Synthesis of 2-((3R*,4S*)-1-(5-(4-chloro-3-fluorophenyl)-7-((2-chloro-6-methylphenyl)(methyl)amino)pyrazolo[1,5-a]pyrimidine-2-carbonyl)-3-methoxypiperidin-4-yl)acetic acid A 4N lithium hydroxide aqueous solution (0.057 mL) was added to a mixture of 2-((3R*,4S*)-1-(5-(4-chloro-3-fluorophenyl)-7-((2-chloro-6-methylphenyl)(methyl)amino)pyrazolo[1,5-a]pyrimidine-2-carbonyl)-3-methoxypiperidin-4-yl)acetic acid ethyl ester (36 mg), water (2 mL), THF (2 mL) and methanol (2 mL) and stirred at room temperature for 15 hours. Acetic acid (0.057 mL) was added to the reaction mixture, which was concentrated under reduced pressure. The residue was purified by reverse phase high performance liquid chromatography (acetonitrile-water, 0.1% acetic acid system), to obtain the title compound (30 mg) as a white solid.

$^1$H-NMR (400 MHz, CD$_3$OD, mixture of rotamers) δ: 1.20-1.58 (m, 2H), 2.00-2.48 (m, 6H), 2.55-3.10 (m, 3H), 3.29-3.58 (m, 6H), 3.99-4.54 (m, 2H), 6.79-6.81 (m, 1H), 6.95-6.97 (m, 1H), 7.22-7.38 (m, 3H), 7.63 (t, J=8 Hz, 1H), 8.01 (d, J=9 Hz, 1H), 8.09 (d, J=11 Hz, 1H).

Example 12

Synthesis of 2-((3R*,4S*)-1-(5-(4-chloro-3,5-difluorophenyl)-7-((2-chloro-6-methylphenyl)(methyl)amino)pyrazolo[1,5-a]pyrimidine-2-carbonyl)-3-methoxypiperidin-4-yl)acetic acid

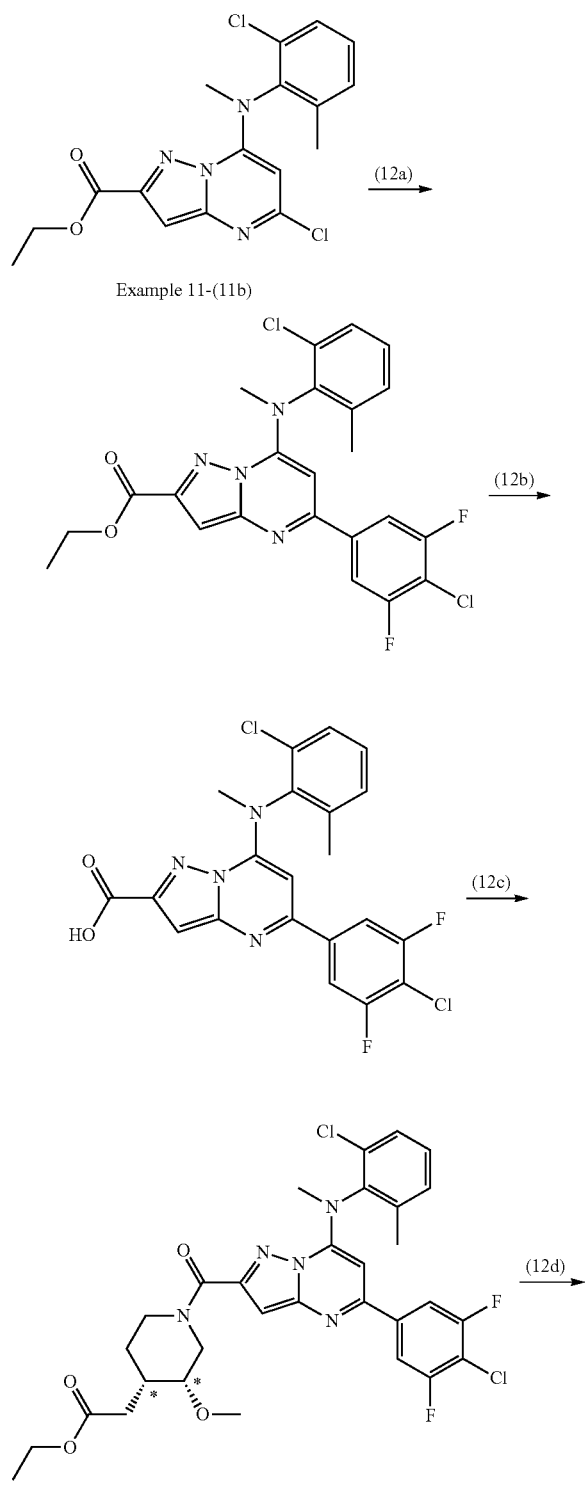

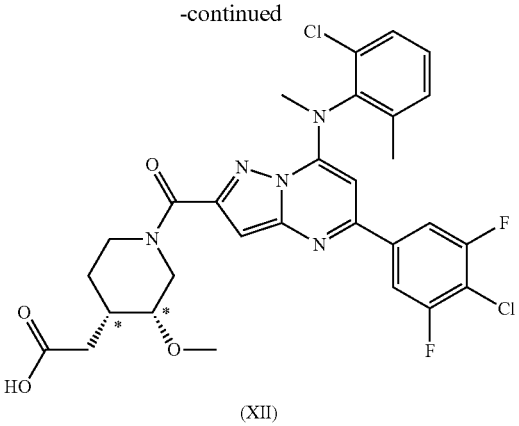

(XII)

(12a) Synthesis of 5-(4-chloro-3,5-difluorophenyl)-7-((2-chloro-6-methylphenyl)(methyl)amino)pyrazolo[1,5-a]pyrimidine-2-carboxylic acid ethyl ester Under a nitrogen atmosphere, water (5 mL), sodium carbonate (0.63 g), 4-chloro-3,5-difluorophenylboronic acid (0.57 g) and tetrakis(triphenylphosphine)palladium (0) (0.14 g) were added to a mixture of 5-chloro-7-((2-chloro-6-methylphenyl)(methyl)amino)pyrazolo[1,5-a]pyrimidine-2-carboxylic acid ethyl ester (0.94 g) (Example 11-(11b)) and 1,4-dioxane (40 mL) and stirred at 90° C. for 18 hours. After bringing the reaction mixture back to room temperature, ethyl acetate (200 mL) and water (100 mL) were added to it, and the organic layer was separated and dried over anhydrous magnesium sulfate. The drying agent was filtered off and the filtrate was concentrated under reduced pressure. The residue was purified by silica gel column chromatography (heptane-ethyl acetate system), to obtain the title compound (0.99 g) as a solid.
$^1$H-NMR (500 MHz, CDCl$_3$, 55° C., mixture of rotamers) δ: 1.37 (t, J=7 Hz, 3H), 2.29 (s, 3H), 3.89 (s, 3H), 4.37 (q, J=7 Hz, 2H), 6.02 (br.s, 1H), 6.99 (s, 1H), 7.25-7.29 (m, 2H), 7.34 (m, 1H), 7.55 (br.d, J=7 Hz, 2H).

(12b) Synthesis of 5-(4-chloro-3,5-difluorophenyl)-7-((2-chloro-6-methylphenyl)(methyl)amino)pyrazolo[1,5-a]pyrimidine-2-carboxylic acid Water (5 mL) and a 4N lithium hydroxide aqueous solution (0.98 mL) were added to a mixture of 5-(4-chloro-3,5-difluorophenyl)-7-((2-chloro-6-methylphenyl)(methyl)amino)pyrazolo[1,5-a]pyrimidine-2-carboxylic acid ethyl ester (0.96 g) and 1,4-dioxane (40 mL) and stirred at room temperature for 15 hours. Acetic acid (0.2 mL) and 5N hydrochloric acid (0.5 mL) were added and the reaction mixture was concentrated under reduced pressure to a volume of about 5 mL. The solid was collected by filtration, washed with water (5 mL) and dried under reduced pressure. The title compound (0.88 g) was obtained as a white solid.
$^1$H-NMR (500 MHz, CDCl$_3$, 55° C., mixture of rotamers) δ: 2.28 (s, 3H), 3.68 (br.s, 3H), 6.40 (br.s, 1H), 7.03 (s, 1H), 7.25-7.35 (m, 3H), 7.68 (br.s, 2H).

(12c) Synthesis of 2-((3R*,4S*)-1-(5-(4-chloro-3,5-difluorophenyl)-7-((2-chloro-6-methylphenyl)(methyl)amino)pyrazolo[1,5-a]pyrimidine-2-carbonyl)-3-methoxypiperidin-4-yl)acetic acid ethyl ester HOBT (57 mg), WSC (72 mg), 2-((3R*,4S*)-3-methoxypiperidin-4-yl)acetic acid ethyl ester hydrochloride (77 mg) (Production Example 2) and triethylamine (101 mg) were added sequentially to a solution of 5-(4-chloro-3,5-difluorophenyl)-7-((2-chloro-6-methylphenyl(methyl)amino)-pyrazolo[1,5-a]pyrimidine-2-carboxylic acid (116 mg) in DMF (5 mL) and stirred at room temperature for 15 hours. Ethyl acetate (50 mL) and water (25 mL) were added to the reaction mixture, and the organic layer was washed with water (25 mL×2) and dried over anhydrous magnesium sulfate. The drying agent was filtered off and the filtrate was concentrated under reduced pressure. The residue was purified by silica gel column chromatography (heptane-ethyl acetate system), to obtain the title, compound (125 mg).

$^1$H-NMR (400 MHz, CD$_3$OD, mixture of rotamers) δ: 1.24 (m, 3H), 1.24-1.58 (m, 2H), 2.00-2.48 (m, 6H), 2.55-3.07 (m, 3H), 3.30-3.40 (m, 3H), 3.52-3.56 (m, 3H), 3.98-4.52 (m, 2H), 4.12 (q, J=7 Hz, 2H), 6.80-83 (m, 1H), 6.98 (m, 1H), 7.21-7.39 (m, 3H), 7.32 (br.d, J=9 Hz, 2H).

(12d) Synthesis of 2-((3R*,4S*)-1-(5-(4-chloro-3,5-difluorophenyl)-7-((2-chloro-6-methylphenyl(methyl)amino)pyrazolo[1,5-a]pyrimidine-2-carbonyl)-3-methoxypiperidin-4-yl)acetic acid A 4N lithium hydroxide aqueous solution (0.053 mL) was added to a mixture of 2-((3R*,4S*)-1-(5-(4-chloro-3,5-difluorophenyl)-7-((2-chloro-6-methylphenyl)(methyl)amino)pyrazolo[1,5-a]pyrimidine-2-carbonyl)-3-methoxypiperidin-4-yl)acetic acid ethyl ester (34 mg), water (2 mL), THF (2 mL) and methanol (2 mL) and stirred at room temperature for 15 hours. Acetic acid (0.053 mL) was added to the reaction mixture, which was concentrated under reduced pressure. The residue was purified by reverse phase high performance liquid chromatography, (acetonitrile-water, 0.1% acetic acid system), to obtain the title compound (36 mg).

$^1$H-NMR (400 MHz, CD$_3$OD, mixture of rotamers) δ: 1.20-1.58 (m, 2H), 2.00-2.48 (m, 6H), 2.55-3.08 (m, 3H), 3.29-3.58 (m, 6H), 3.99-4.54 (m, 2H), 6.81-6.84 (m, 1H), 6.99-7.01 (m, 1H), 7.25-7.39 (m, 3H), 8.03 (d, J=9 Hz, 2H).

Example 13

Synthesis of 2-((3R*,4S*)-1-(7-((2-chloro-6-fluorophenyl)(methyl)amino)-5-(3,4,5-trifluorophenyl)pyrazolo[1,5-a]pyrimidine-2-carbonyl)-3-fluoropiperidin-4-yl)acetic acid

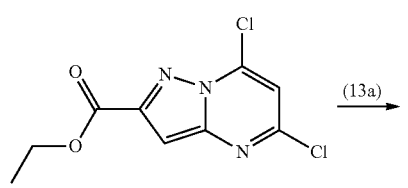

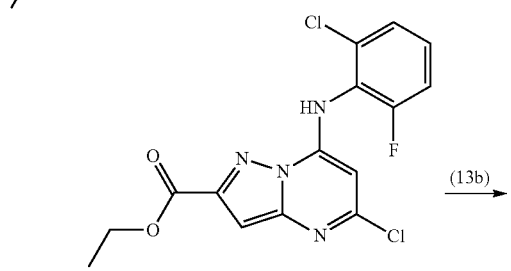

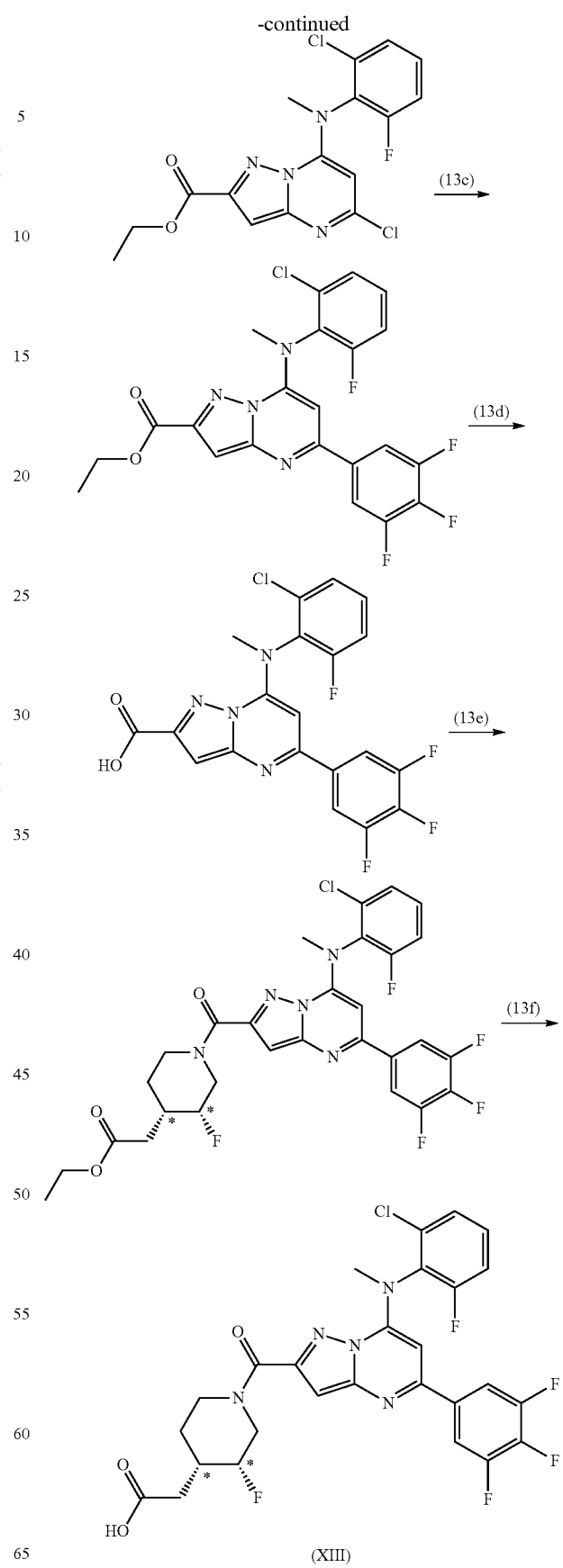

(13a) Synthesis of 5-chloro-7-((2-chloro-6-fluorophenyl)amino)pyrazolo[1,5-a]pyrimidine-2-carboxylic acid ethyl ester Potassium t-butoxide (0.070 g) was added to a mixture of 2-chloro-6-fluoroaniline (CAS No. 363-51-9) (0.090 g) and THF (5 mL) and stirred at room temperature for 15 minutes. 5,7-Dichloropyrazolo[1,5-a]pyrimidine-2-carboxylic acid ethyl ester (CAS No. 1232224-62-2) (0.100 g) was added and stirred with heating at 50° C. for 1 hour. A saturated ammonium chloride aqueous solution was added to separate the organic layer from the aqueous layer. The aqueous layer was extracted with ethyl acetate, the organic layers were combined and dried over anhydrous sodium sulfate. The drying agent was filtered off and the filtrate was concentrated under reduced pressure. The residue was purified by silica gel column chromatography (heptane-ethyl acetate system), to obtain the title compound (0.063 g) as a light yellow solid.
$^1$H-NMR (400 MHz, CDCl$_3$) δ: 1.46 (t, J=7 Hz, 3H), 4.30 (q, J=7 Hz, 2H), 5.87 (s, 1H), 7.04 (s, 1H), 7.23-7.27 (m, 1H), 7.40-7.43 (m, 2H), 7.98 (br.s, 1H).

(13b) Synthesis of 5-chloro-7-((2-chloro-6-fluorophenyl)(methyl)amino)pyrazolo[1,5-a]pyrimidine-2-carboxylic acid ethyl ester Potassium carbonate (0.050 g) and methyl iodide (0.050 mL) were added to a solution of 5-chloro-7-((2-chloro-6-fluorophenyl)amino)pyrazolo[1,5-a]pyrimidine-2-carboxylic acid ethyl ester (0.063 g) in DMF (2 mL) and stirred at 50° C. for 3 hours. A saturated ammonium chloride aqueous solution and ethyl acetate were added to the reaction mixture to separate the organic layer from the aqueous layer. The aqueous layer was extracted with ethyl acetate, the organic layers were combined and dried over anhydrous sodium sulfate. The drying agent was filtered off and the filtrate was concentrated under reduced pressure. The residue was purified by silica gel column chromatography (heptane-ethyl acetate system), to obtain the title compound (0.047 g).
$^1$H-NMR (400 MHz, CDCl$_3$) δ: 1.31 (t, J=7 Hz, 3H), 3.64 (br.s, 3H), 4.28 (q, J=7 Hz, 2H), 6.11 (br.s, 1H), 6.87 (s, 1H), 7.12 (td, J=9, 2 Hz, 1H), 7.28 (br.d, J=9 Hz, 1H), 7.34 (td, J=9, 6 Hz, 1H).

(13c) Synthesis of 7-((2-chloro-6-fluorophenyl)(methyl)amino)-5-(3,4,5-trifluorophenyl)pyrazolo[1,5-a]pyrimidine-2-carboxylic acid ethyl ester Under a nitrogen atmosphere, water (0.2 mL), potassium carbonate (0.030 g), 3,4,5-trifluorophenylboronic acid (0.025 g) and tetrakis(triphenylphosphine)palladium (0) (0.010 g) were added to a mixture of 5-chloro-7-((2-chloro-6-fluorophenyl)(methyl)amino)pyrazolo[1,5-a]pyrimidine-2-carboxylic acid ethyl ester (0.047 g) and 1,4-dioxane (2 mL) and stirred at 80° C. for 3 hours. The reaction mixture was concentrated under reduced pressure and the residue was purified by silica gel column chromatography (heptane-ethyl acetate system), to obtain the title compound (0.052 g) as a white solid.
$^1$H-NMR (400 MHz, CDCl$_3$) δ: 1.32 (t, J=7 Hz, 3H), 3.72 (br.s, 3H), 4.30 (q, J=7 Hz, 2H), 6.42 (br.s, 1H), 7.00 (s, 1H), 7.13 (td, J=9, 2 Hz, 1H), 7.28 (br.d, J=9 Hz, 1H), 7.34 (td, J=9, 6 Hz, 1H), 7.70 (m, 2H).

(13d) Synthesis of 7-((2-chloro-6-fluorophenyl)(methyl)amino)-5-(3,4,5-trifluorophenyl)pyrazolo[1,5-a]pyrimidine-2-carboxylic acid A 5N sodium hydroxide aqueous solution (0.10 mL) was added to a mixture of 7-((2-chloro-6-fluorophenyl)(methyl)amino)-5-(3,4,5-trifluorophenyl)pyrazolo[1,5-a]pyrimidine-2-carboxylic acid ethyl ester (0.052 g), THF (1 mL) and ethanol (1 mL) and stirred at room temperature for 1 hour. 5N hydrochloric acid, ethyl acetate and water were added to the reaction mixture to separate the organic layer from the aqueous layer. The aqueous layer was extracted with ethyl acetate, the organic layers were combined and dried over anhydrous sodium sulfate. The drying agent was filtered off and the filtrate was concentrated under reduced pressure, to obtain the title compound (0.047 g) as a white solid.
$^1$H-NMR (400 MHz, CDCl$_3$) δ: 3.66 (s, 3H), 6.62 (s, 1H), 7.08 (s, 1H), 7.14 (td, J=8, 1 Hz, 1H), 7.32 (br.d, J=8 Hz, 1H), 7.39 (td, J=8, 6 Hz, 1H), 7.76 (dd, J=9, 7 Hz, 2H).

(13e) Synthesis of 2-((3R*,4S*)-1-(7-((2-chloro-6-fluorophenyl)(methyl)amino)-5-(3,4,5-trifluorophenyl)pyrazolo[1,5-a]pyrimidine-2-carbonyl)-3-fluoropiperidin-4-yl)acetic acid ethyl ester HOBT (0.063 g), WSC (0.079 g), 2-((3R*,4S*)-3-fluoropiperidin-4-yl)acetic acid ethyl ester hydrobromide (0.082 g) (Production Example 1) and triethylamine (0.111 g) were added sequentially to a solution of 7-((2-chloro-6-fluorophenyl)(methyl)amino)-5-(3,4,5-trifluorophenyl)pyrazolo[1,5-a]pyrimidine-2-carboxylic acid (0.124 g) in DMF (5 mL) and stirred at room temperature for 15 hours. Ethyl acetate (60 mL) and water (30 mL) were added to the reaction mixture, and the organic layer was washed with water (30 mL×2) and dried over anhydrous magnesium sulfate. The drying agent was filtered off and the filtrate was concentrated under reduced pressure. The residue was purified by silica gel column chromatography (heptane-ethyl acetate system), to obtain the title compound (0.125 g) as a white solid.
$^1$H-NMR (500 MHz, CDCl$_3$, mixture of rotamers) δ: 1.26-1.32 (m, 3H), 1.40-1.52 (m, 1H), 1.60-1.71 (m, 1H), 2.08-2.23 (m, 1H), 2.30 (td, J=14, 6 Hz, 1H), 2.53 (m, 1H), 2.65-2.90 (m, 2H), 3.60 (m, 3H), 4.10-4.21 (m, 2H), 4.36-5.04 (m, 3H), 6.54-7.09 (m, 3H), 7.24-7.31 (m, 2H), 7.71-7.79 (m, 2H).

(13f) Synthesis of 2-(((3R*,4S*)-1-(7-((2-chloro-6-fluorophenyl)(methyl)amino)-5-(3,4,5-trifluorophenyl)pyrazolo[1,5-a]pyrimidine-2-carbonyl)-3-fluoropiperidin-4-yl)acetic acid An aqueous solution (2 mL) of lithium hydroxide (0.0096 g) was added to a solution of 2-((3R*,4S*)-1-(7-((2-chloro-6-fluorophenyl)(methyl)amino)-5-(3,4,5-trifluorophenyl)pyrazolo[1,5-a]pyrimidine-2-carbonyl)-3-fluoropiperidin-4-yl)acetic acid ethyl ester (0.125 g) in 1,4-dioxane (6 mL) and stirred at room temperature for 15 hours. DMSO (2 mL) and acetic acid (0.1 mL) were added to the reaction mixture, which was concentrated under reduced pressure. The residue was purified by reverse phase silica gel column chromatography (acetonitrile-water, 0.1% acetic acid system), the fractions containing the title compound were combined and concentrated under reduced pressure to a volume of 5 mL. The precipitate was collected by filtration, washed with water (5 mL) and dried under reduced pressure, to obtain the title compound (0.104 g) as a white solid.
$^1$H-NMR (500 MHz, CDCl$_3$, mixture of rotamers) δ: 1.43-1.51 (m, 1H), 1.62-1.73 (m, 1H), 2.09-2.22 (m, 1H), 2.34-2.42 (m, 1H), 2.58-2.91 (m, 3H), 3.60 (s, 1.5H), 3.61 (s, 1.5H), 4.38-5.05 (m, 3H), 6.54 (s, 0.5H), 6.56 (s, 0.5H), 6.99 (s, 0.5H), 7.02 (s, 0.5H), 7.02-7.09 (m, 1H), 7.25-7.30 (m, 2H), 7.72-7.78 (m, 2H).
Mass spectrum (ESI) m/z: 594/596 (M+H)$^+$

Example 14

Synthesis of 2-((3R*,4S*)-1-(5-(4-chloro-3,5-difluorophenyl)-7-((2-chlorophenyl)(methyl)amino)pyrazolo[1,5-a]pyrimidine-2-carbonyl)-3-fluoropiperidin-4-yl)acetic acid

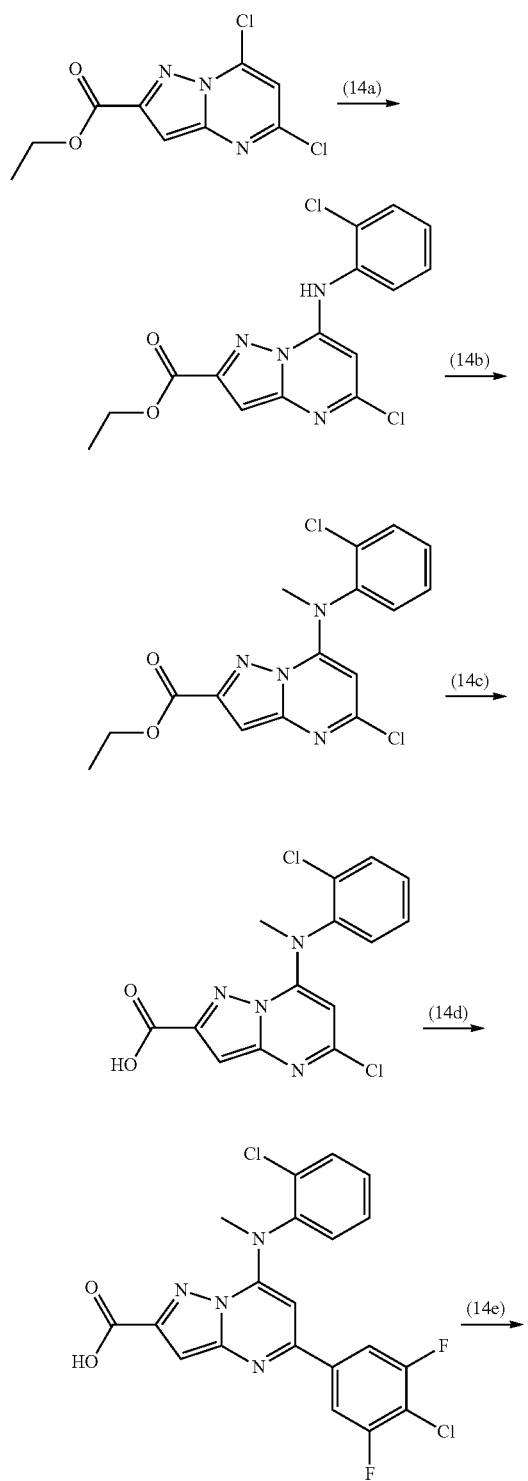

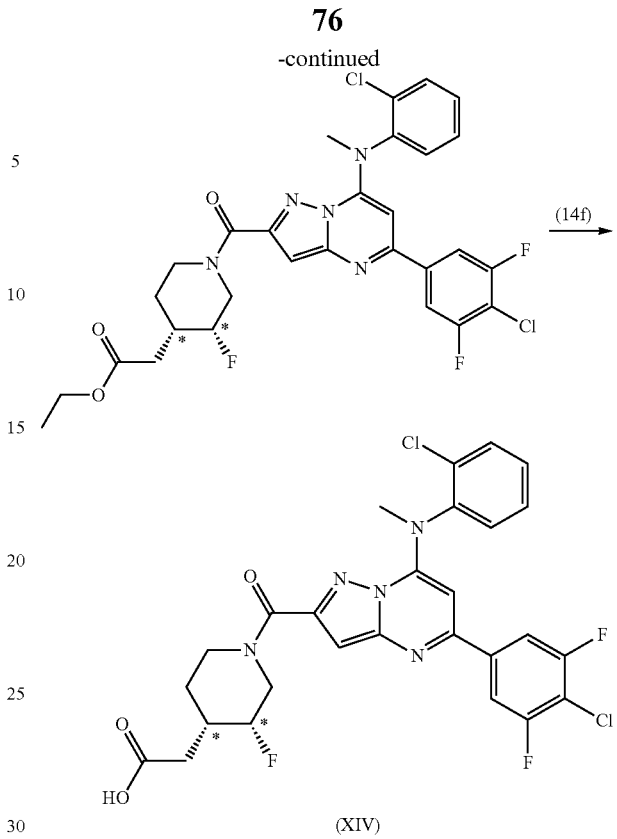

(14a) Synthesis of 5-chloro-7-((2-chlorophenyl)amino)pyrazolo[1,5-a]pyrimidine-2-carboxylic acid ethyl ester A solution of 5,7-dichloropyrazolo[1,5-a]pyrimidine-2-carboxylic acid ethyl ester (CAS No. 1232224-62-2) (1.7 g) and 2-chloroaniline (CAS No. 95-51-2) (0.92 g) in NMP (1.3 mL) was stirred with heating at 120° C. for 1 hour and 130° C. for 2 hours. The reaction mixture was cooled, subsequently diluted with ethyl acetate and sonicated. The solid was collected by filtration, washed with ethyl acetate and dried under reduced pressure, to obtain the title compound (1.3 g) as a light yellow solid.

$^1$H-NMR (400 MHz, CDCl$_3$) δ: 1.46 (t, J=7 Hz, 3H), 4.50 (q, J=7 Hz, 2H), 6.20 (s, 1H), 7.03 (s, 1H), 7.36 (td, J=8, 2 Hz, 1H), 7.44 (td, J=8, 2 Hz, 1H), 7.53 (dd, J=8, 2 Hz, 1H), 7.59 (dd, J=8, 2 Hz, 1H), 8.29 (br.s, 1H).

(14b) Synthesis of 5-chloro-7-((2-chlorophenyl)(methyl)amino)pyrazolo[1,5-a]pyrimidine-2-carboxylic acid ethyl ester Potassium carbonate (0.61 g) and methyl iodide (0.46 mL) were added to a solution of 5-chloro-7-((2-chlorophenyl)amino)pyrazolo[1,5-a]pyrimidine-2-carboxylic acid ethyl ester (1.30 g) in DMF (10 mL) and stirred with heating at 50° C. for 3 hours. Ethyl acetate was added to the reaction mixture, which was washed twice with a saturated sodium chloride aqueous solution. The organic layer was dried over anhydrous magnesium sulfate. The drying agent was filtered off and the filtrate was concentrated under reduced pressure. The residue was purified by silica gel column chromatography (heptane-ethyl acetate system), to obtain the title compound (1.21 g) as a light yellow solid.

¹H-NMR (400 MHz, CDCl₃) δ: 1.35 (t, J=7 Hz, 3H), 3.83 (s, 3H), 4.35 (q, J=7 Hz, 2H), 5.85 (s, 1H), 6.89 (s, 1H), 7.34-7.41 (m, 3H), 7.49-7.52 (m, 1H).

Mass spectrum (ESI) m/z: 365/367 (M+H)⁺

(14c) Synthesis of 5-chloro-7-((2-chlorophenyl)(methyl)amino)pyrazolo[1,5-a]pyrimidine-2-carboxylic acid A 5N sodium hydroxide aqueous solution (2.0 mL) was added to a solution of 5-chloro-7-((2-chlorophenyl)(methyl)amino)pyrazolo[1,5-a]pyrimidine-2-carboxylic acid ethyl ester (1.2 g) in 1,4-dioxane and stirred with heating at 105° C. for 2 hours. The reaction mixture was cooled, made weakly acidic with 5N hydrochloric acid and extracted with ethyl acetate. The organic layer was dried over anhydrous magnesium sulfate. The drying agent was filtered off and the filtrate was concentrated under reduced pressure, to obtain a crude product of the title compound (1.2 g) as a light yellow solid.

¹H-NMR (400 MHz, DMSO-d₆) δ: 3.64 (s, 3H), 6.34 (s, 1H), 6.83 (s, 1H), 7.38-7.45 (m, 2H), 7.51-7.57 (m, 2H), 13.10 (br.s, 1H).

Mass spectrum (ESI) m/z: 337/339 (M+H)⁺

(14d) Synthesis of 5-(4-chloro-3,5-difluorophenyl)-7-((2-chlorophenyl)(methyl)amino)pyrazolo[1,5-a]pyrimidine-2-carboxylic acid Water (2 mL), sodium carbonate (0.20 g), 4-chloro-3,5-difluorophenylboronic acid (0.14 g) and tetrakis(triphenylphosphine)palladium (0) (0.048 g) were added to a mixture of 5-chloro-7-((2-chlorophenyl)(methyl)amino)pyrazolo[1,5-a]pyrimidine-2-carboxylic acid (0.19 g) and 1,4-dioxane (10 mL) and stirred at 95° C. for 2 hours. Ethyl acetate (100 mL), water (50 mL) and 5N hydrochloric acid (50 mL) were added to the reaction mixture, and the organic layer was separated and dried over anhydrous magnesium sulfate. The drying agent was filtered off, the reaction mixture was concentrated under reduced pressure and the residue was purified by reverse phase silica gel column chromatography (acetonitrile-water, 0.1% acetic acid system), to obtain the title compound (0.188 g).

¹H-NMR (400 MHz, CDCl₃) δ: 3.74 (s, 3H), 6.53 (s, 1H), 7.08 (s, 1H), 7.34-7.43 (m, 3H), 7.51-7.54 (m, 1H), 7.71 (d, J=8 Hz, 2H).

(14e) Synthesis of 2-((3R,4S*)-1-(5-(4-chloro-3,5-difluorophenyl)-7-((2-chlorophenyl)(methyl)amino)pyrazolo[1,5-a]pyrimidine-2-carbonyl)-3-fluoropiperidin-4-yl)acetic acid ethyl ester HOBT (0.063 g), WSC (0.079 g), 2-((3R*,4S*)-3-fluoropiperidin-4-yl)acetic acid ethyl ester hydrobromide (0.082 g) (Production Example 1) and triethylamine (0.111 g) were added sequentially to a solution of 5-(4-chloro-3,5-difluorophenyl)-7-((2-chlorophenyl(methyl)amino)pyrazolo[1,5-a]pyrimidine-2-carboxylic acid (0.124 g) in DMF (5 mL) and stirred at room temperature for 15 hours. Ethyl acetate (60 mL) and water (30 mL) were added to the reaction mixture, and the organic layer was washed with water (30 mL×2) and dried over anhydrous magnesium sulfate. The drying agent was filtered off and the filtrate was concentrated under reduced pressure. The residue was purified by silica gel column chromatography (heptane-ethyl acetate system), to obtain the title compound (163 mg) as a white solid.

¹H-NMR (500 MHz, CDCl₃, mixture of rotamers) δ: 1.26-1.32 (m, 3H), 1.40-1.52 (m, 1H), 1.60-1.71 (m, 1H), 2.08-2.23 (m, 1H), 2.26-2.35 (m, 1H), 2.53 (m, 1H), 2.66-2.91 (m, 2H), 3.65 (s, 1.2H), 3.66 (s, 1.8H), 4.10-4.21 (m, 2H), 4.39-5.06 (m, 3H), 6.48 (s, 0.6H), 6.50 (s, 0.4H), 7.01 (s, 0.4H), 7.03 (s, 0.6H), 7.15-7.23 (m, 1H), 7.26-7.32 (m, 2H), 7.47-7.52 (m, 1H), 7.68-7.72 (m, 2H).

(14f) Synthesis of 2-(((3R*,4S*)-1-(5-(4-chloro-3,5-difluorophenyl)-7-chlorophenyl)(methyl)amino)pyrazolo[1,5-a]pyrimidine-2-carbonyl)-3-fluoropiperidin-4-yl)acetic acid An aqueous solution (2 mL) of lithium hydroxide (0.0126 g) was added to a solution of 2-((3R*,4S*)-1-(5-(4-chloro-3,5-difluorophenyl)-7-((2-chlorophenyl)(methyl)amino)pyrazolo[1,5-a]pyrimidine-2-carbonyl)-3-fluoropiperidin-4-yl)acetic acid ethyl ester (0.163 g) in 1,4-dioxane (6 mL) and stirred at room temperature for 15 hours. DMSO (2 mL) and acetic acid (0.1 mL) were added to the reaction mixture, which was concentrated under reduced pressure. The residue was purified by reverse phase silica gel column chromatography (acetonitrile-water, 0.1% acetic acid system), the fractions containing the title compound were combined and concentrated under reduced pressure to a volume of 5 mL. The precipitate was collected by filtration, washed with water (5 mL) and dried under reduced pressure, to obtain the title compound (0.132 g) as a white solid.

¹H-NMR (500 MHz, CDCl₃, mixture of rotamers) δ: 1.44-1.54 (m, 1H), 1.63-1.73 (m, 1H), 2.09-2.23 (m, 1H), 2.38 (ddd, J=17, 11, 7 Hz, 1H), 2.60 (ddd, J=17, 10, 7 Hz, 1H), 2.67-2.92 (m, 2H), 3.65 (s, 1.2H), 3.67 (s, 1.8H), 4.42-5.07 (m, 3H), 6.48 (s, 0.6H), 6.51 (s, 0.4H), 7.02 (s, 0.4H), 7.04 (s, 0.6H), 7.15-7.23 (m, 1H), 7.26-7.32 (m, 2H), 7.47-7.52 (m, 1H), 7.68-7.72 (m, 2H).

Mass spectrum (ESI) m/z: 592/594 (M+H)⁺

Example 15

Synthesis of 2-(1α,5α,6α)-3-(5-(4-chloro-3,5-difluorophenyl)-7-(isopropyl(propyl)amino)pyrazolo[1,5-a]pyrimidine-2-carbonyl)-3-azabicyclo[3.1.0]hexan-6-yl)acetic acid

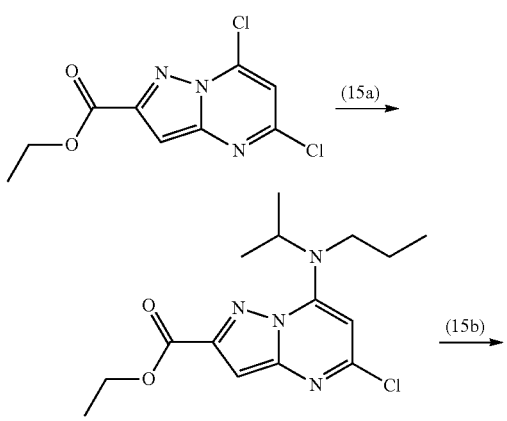

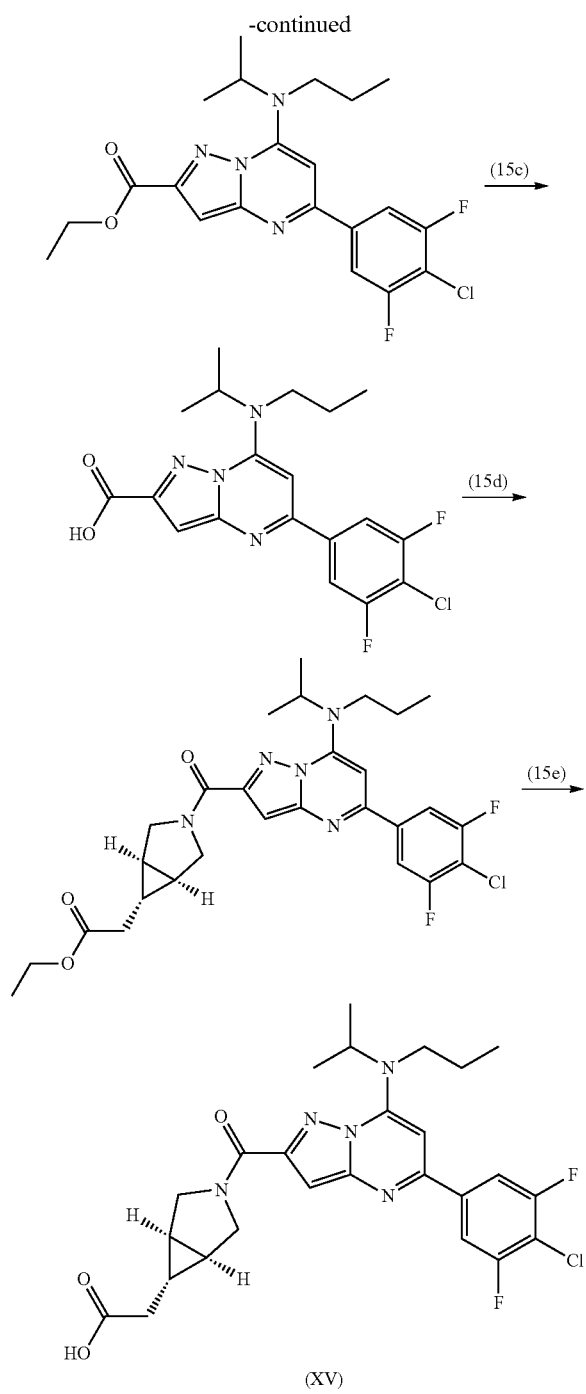

(15a) Synthesis of 5-chloro-7-(isopropyl(propyl)amino)pyrazolo[1,5-a]pyrimidine-2-carboxylic acid ethyl ester N-Isopropylpropylamine (CAS No. 21968-17-2) (0.32 g) was added to a mixture of 5,7-dichloropyrazolo[1,5-a]pyrimidine-2-carboxylic acid ethyl ester (CAS No. 1232224-62-2) (0.78 g), triethylamine (1.47 mL) and THF (15 mL) and stirred at room temperature overnight. Ethyl acetate (100 mL) and a saturated ammonium chloride aqueous solution (50 mL) were added to the reaction mixture, and the organic layer was separated and dried over anhydrous magnesium sulfate. The drying agent was filtered off and the filtrate was concentrated under reduced pressure. The residue was purified by silica gel column chromatography (heptane-ethyl acetate system), to obtain the title compound (0.71 g) as a light yellow liquid.

$^1$H-NMR (500 MHz, CDCl$_3$) δ: 0.94 (t, J=7 Hz, 3H), 1.35 (d, J=7 Hz, 6H), 1.42 (t, J=7 Hz, 3H), 1.60 (m, 2H), 3.55 (m, 2H), 4.43 (q, J=7 Hz, 2H), 4.95 (m, 1H), 6.06 (s, 1H), 6.89 (s, 1H).

(15b) Synthesis of 5-(4-chloro-3,5-difluorophenyl)-7-(isopropyl(propyl)amino)pyrazolo[1,5-a]pyrimidine-2-carboxylic acid ethyl ester A mixture of 5-chloro-7-(isopropyl(propyl)amino)pyrazolo[1,5-a]pyrimidine-2-carboxylic acid ethyl ester (0.64 g), 1,4-dioxane (9 mL), water (1 mL), sodium carbonate (0.31 g), 4-chloro-3,5-difluorophenyl boronic acid (0.42 g) and tetrakis(triphenylphosphine)palladium (0) (0.23 g) was stirred at 80° C. for 3 hours. The reaction mixture was filtered through NH silica gel and concentrated under reduced pressure. The residue was purified by silica gel column chromatography (heptane-ethyl acetate system), to obtain the title compound (0168 g).

$^1$H-NMR (400 MHz, CDCl$_3$) δ: 0.96 (t, J=7 Hz, 3H), 1.39 (d, J=7 Hz, 6H), 1.44 (t, J=7 Hz, 3H), 1.62 (m, 2H), 3.61 (m, 2H), 4.45 (q, J=7 Hz, 2H), 5.01 (m, 1H), 6.41 (s, 1H), 7.05 (s, 1H), 7.67 (d, J=7 Hz, 2H).

(15c) Synthesis of 5-(4-chloro-3,5-difluorophenyl)-7-(isopropyl(propyl)amino)pyrazolo[1,5-a]pyrimidine-2-carboxylic acid A mixture of 5-(4-chloro-3,5-difluorophenyl)-7-(isopropyl(propyl)amino)pyrazolo[1,5-a]pyrimidine-2-carboxylic acid ethyl ester (0.68 g), 1,4-dioxane (20 mL), water (4 mL) and a 4N lithium hydroxide aqueous solution (1.5 mL) was stirred at room temperature overnight. 2N Hydrochloric acid (3 mL) was added, the reaction mixture was concentrated under reduced pressure and the precipitate was collected by filtration. The residue was washed with water and dried under reduced pressure, to obtain the title compound (0.60 g).

$^1$H-NMR (400 MHz, DMSO-d$_6$) δ: 0.86 (t, J=7 Hz, 3H), 1.30 (d, J=7 Hz, 6H), 1.48 (m, 2H), 3.69 (t, J=7 Hz, 2H), 5.02 (m, 1H), 6.91 (s, 1H), 6.99 (s, 1H), 8.17 (d, J=9 Hz, 2H).

Mass spectrum (ESI) m/z: 409 (M+H)$^+$ (15d) Synthesis of 2-((1α,5α,6α)-3-(5-(4-chloro-3,5-difluorophenyl)-7-(isopropyl(propyl)amino)pyrazolo[1,5-a]pyrimidine-2-carbonyl)-3-azabicyclo[3.1.0]hexan-6-yl)acetic acid ethyl ester HOBT (0.079 g), WSC (0.099 g), 2-((1α,5α,6α)-3-azabicyclo[3.1.0]hexan-6-yl)acetic acid ethyl ester hydrochloride (0.085 g) (2-(1α,5α,6α)-3-azabicyclo[3.1.0]hexan-6-yl)acetic acid ethyl ester (CAS No. 1251668-97-9) (WO 2010/116328) was converted to its hydrochloride by a conventional method) and triethylamine (0.105 g) were added sequentially to a solution of 5-(4-chloro-3,5-difluorophenyl)-7-(isopropyl(propyl)amino)pyrazolo[1,5-a]pyrimidine-2-carboxylic acid (141 mg) in DMF (5 mL) and stirred at room temperature for 15 hours. Ethyl acetate (100 mL) and water (50 mL) were added to the reaction mixture, and the organic layer was washed with water (50 mL×2) and dried over anhydrous magnesium sulfate. The drying agent was filtered off and the filtrate was concentrated under reduced pressure. The residue was purified by silica gel column chromatography (heptane-ethyl acetate system), to obtain the title compound (0.127 g) as a colorless liquid.

$^1$H-NMR (500 MHz, CDCl$_3$) δ: 0.95 (t, J=7 Hz, 3H), 0.95-1.00 (m, 1H), 1.26 (t, J=7 Hz, 3H), 1.35 (d, J=7 Hz, 3H), 1.36 (d, J=7 Hz, 3H) 1.50-1.53 (m, 1H), 1.55-1.57 (m, 1H), 1.61 (m, 2H), 2.24 (dd, J=16, 8 Hz, 1H), 2.36 (dd, J=16, 7 Hz, 1H), 3.47-3.57 (m, 2H), 3.65 (dd, J=13, 4 Hz, 1H), 3.97 (dd, J=12, 4 Hz, 1H), 4.14 (q, J=7 Hz, 2H), 4.19 (d, J=13 Hz, 1H), 4.36 (d, J=12 Hz, 1H), 5.11 (m, 1H), 6.40 (s, 1H), 7.03 (s, 1H), 7.67 (d, J=8 Hz, 2H).

(15e) Synthesis of 2-((1α,5α,6α)-3-(5-(4-chloro-3,5-difluorophenyl)-7-(isopropyl(propyl)amino)pyrazolo[1,5-a]pyrimidine-2-carbonyl)-3-azabicyclo[3.1.0]hexan-6-yl)acetic acid An aqueous solution (2 mL) of lithium hydroxide (0.0109 g) was added to a solution of 2-((1α,5α,6α)-3-(5-(4-chloro-3,5-difluorophenyl)-7-(isopropyl(propyl)amino)pyrazolo[1,5-a]pyrimidine-2-carbonyl)-3-azabicyclo[3.1.0]hexan-6-yl) acetic acid ethyl ester (0.127 g) in 1,4-dioxane (6 mL) and stirred at room temperature for 16 hours. DMSO (1 mL) and acetic acid (0.06 mL) were added to the reaction mixture, which was concentrated under reduced pressure. The residue was purified by reverse phase silica gel column chromatography (acetonitrile-water, 0.1% acetic acid system), to obtain the title compound (0.111 g) as a yellow solid.

$^1$H-NMR (400 MHz, CDCl$_3$, mixture of rotamers) δ: 0.95 (t, J=7 Hz, 3H), 0.94-1.00 (m, 1H), 1.34-1.37 (m, 6H), 1.53-1.65 (m, 4H), 2.30 (dd, J=16, 8 Hz, 1H), 2.42 (dd, J=16, 7 Hz, 1H), 3.50-3.53 (m, 2H), 3.65 (dd, J=13, 4 Hz, 1H), 3.97 (dd, J=12, 4 Hz, 1H), 4.21 (d, J=13 Hz, 1H), 4.38 (d, J=12 Hz, 1H), 5.11 (m, 1H), 6.39 (s, 1H), 7.03 (s, 1H), 7.67 (d, J=8 Hz, 2H).

Example 16

Synthesis of 2-((1α,5α,6α)-3-(7-(isobutyl((S)-1-phenylethyl)amino)-5-(3,4,5-trifluorophenyl)pyrazolo[1,5-a]pyrimidine-2-carbonyl)-3-azabicyclo[3.1.0]hexan-6-yl)acetic acid

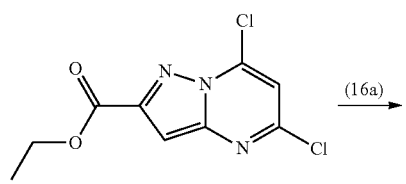

(16a)

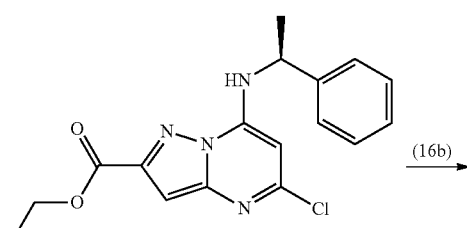

(16b)

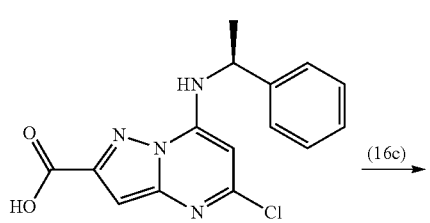

(16c)

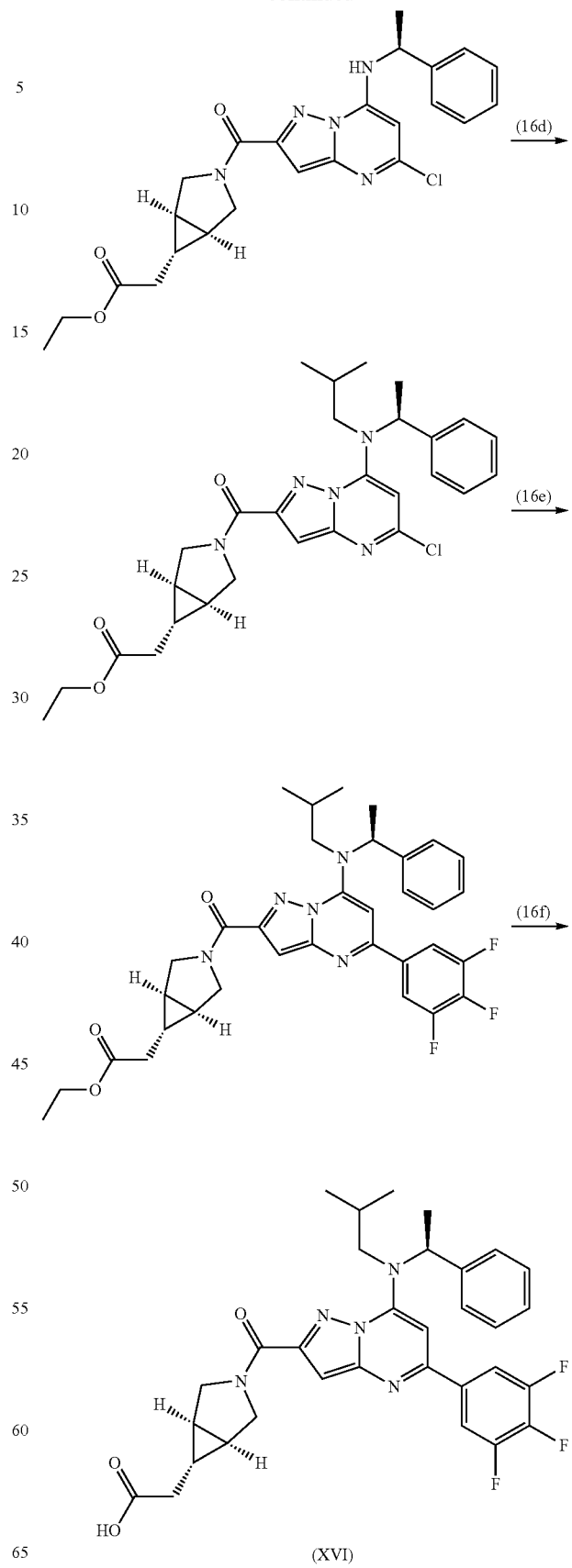

(XVI)

(16a) Synthesis of (S)-5-chloro-7-((1-phenylethyl)amino)pyrazolo[1,5-a]pyrimidine-2-carboxylic acid ethyl ester Triethylamine (10 mL) was added to a mixture of 5,7-dichloropyrazolo[1,5-a]pyrimidine-2-carboxylic acid ethyl ester (CAS No. 1232224-62-2) (5 g), THF (75 mL) and (S)-(−)-α-methylbenzyl amine (CAS No. 2627-86-3) (2.50 g) and stirred at room temperature overnight. Ethyl acetate and water were added to the reaction mixture, and the organic layer was washed with a saturated sodium chloride aqueous solution and dried over anhydrous sodium, sulfate. The drying agent was filtered off and the filtrate was concentrated under reduced pressure. The residue was purified by NH silica gel column chromatography (heptane-ethyl acetate system), to obtain the title compound (6.47 g) as a colorless liquid.

$^1$H-NMR (400 MHz, DMSO-d$_6$) δ: 1.35 (t, J=7 Hz, 3H), 1.66 (d, J=7 Hz, 3H), 4.39 (q, J=7 Hz, 2H), 5.03 (q, J=7 Hz, 1H), 6.25 (s, 1H), 6.86 (s, 1H), 7.27 (t, J=7 Hz, 1H), 7.36 (t, J=7 Hz, 2H), 7.54 (d, J=7 Hz, 2H).

(16b) Synthesis of (S)-5-chloro-7-((1-phenylethyl)amino)pyrazolo[1,5-a]pyrimidine-2-carboxylic acid A 5N sodium hydroxide aqueous solution (15 mL) was added to a mixture of (S)-5-chloro-7-((1-phenylethyl)amino)pyrazolo[1,5-a]pyrimidine-2-carboxylic acid ethyl ester (6.45 g) and ethanol (100 mL) and stirred with heating at 50° C. for 30 minutes. After cooling, 5N hydrochloric acid (14 mL) and water were added and stirred at room temperature. The precipitate was collected by filtration, washed with water and dried under reduced pressure. The title compound (5.81 g) was obtained as a white solid.

$^1$H-NMR (400 MHz, DMSO-d$_6$) δ: 1.66 (d, J=7 Hz, 3H), 5.03 (quintet, J=7 Hz, 1H), 6.23 (s, 1H), 6.81 (s, 1H), 7.27 (t, J=8 Hz, 1H), 7.36 (t, J=8 Hz, 2H), 7.53 (d, J=8 Hz, 2H), 8.79 (d, J=7 Hz, 1H), 13.40 (br.s, 1H).

(16c) Synthesis of 2-((1α,5α,6α)-3-(5-chloro-7-(((S)-1-phenylethyl)amino)pyrazolo[1,5-a]pyrimidine-2-carbonyl)-3-azabicyclo[3.1.0]hexan-6-yl)acetic acid ethyl ester Triethylamine (2.5 mL) was added to a mixture of (S)-5-chloro-7-((1-phenylethyl)(amino)pyrazolo[1,5-a]pyrimidine-2-carboxylic acid (1 g), DMF (20 mL), HOBT (0.7 g), WSC (1 g) and 2-((1α,5α,6α)-3-azabicyclo[3.1.0]hexan-6-yl)acetic acid ethyl ester hydrochloride (0.7 g) and stirred at room temperature for 23 hours. Ethyl acetate and water were added to the reaction mixture. The organic layer was washed with a saturated sodium chloride aqueous solution and dried over anhydrous sodium sulfate. The drying agent was filtered off and the filtrate was concentrated under reduced pressure. The residue was purified by silica gel column chromatography (heptane-ethyl acetate system), to obtain the title compound (1.02 g) as a colorless liquid.

$^1$H-NMR (400 MHz, DMSO-d$_6$) δ: 0.72-0.79 (m, 1H), 1.18 (t, J=7 Hz, 3H), 1.50-1.60 (m, 2H), 1.66 (d, J=7 Hz, 3H), 2.27-2.39 (m, 2H), 3.47-3.52 (m, 1H), 3.84-4.09 (m, 5H), 5.01-5.08 (m, 1H), 6.19 (s, 1H), 6.85 (s, 1H), 7.27 (t, J=8 Hz, 1H), 7.36 (td, J=8, 2 Hz, 2H), 7.51 (d, J=8 Hz, 2H), 8.58 (br.s, 1H).

(16d) Synthesis of 2-(1α,5α,6α)-3-(5-chloro-7-(isobutyl((S)-1-phenylethyl)amino)pyrazolo[1,5-a]pyrimidine-2-carbonyl)-3-azabicyclo[3.1.0]hexan-6-yl)acetic acid ethyl ester 1-Iodo-2-methylpropane (1.5 mL) was added to a mixture of 2-((1α,5α,6α)-3-(5-chloro-7-(((S)-1-phenylethyl)amino)pyrazolo[1,5-a]pyrimidine-2-carbonyl)-3-azabicyclo[3.1.0]hexan-6-yl)acetic acid ethyl ester (1.02 g), DMF (10 mL) and cesium carbonate (2 g) and stirred with heating at 70° C. for 14 hours. The reaction mixture was cooled and ethyl acetate and water were added. The organic layer was washed with a saturated sodium chloride aqueous solution and dried over anhydrous sodium sulfate. The drying agent was filtered off and the filtrate was concentrated under reduced pressure. The residue was purified by silica gel column chromatography (heptane-ethyl acetate system), to obtain the title compound (0.46 g) as a yellow solid.

$^1$H-NMR (400 MHz, DMSO-d$_6$, mixture of rotamers) δ: 0.71 (m, 3H), 0.73 (m, 1H), 0.80 (m, 3H), 1.15 (m, 3H), 1.48-1.56 (m, 2H), 1.73 (m, 3H), 1.81 (m, 1H), 2.24-2.35 (m, 2H), 2.79-2.87 (m, 1H), 2.95 (dd, J=15, 5 Hz, 1H), 3.50 (dt, 12, 5 Hz, 1H), 3.84-3.94 (m, 2H), 4.00-4.07 (m, 2H), 4.21 (dd, J=11, 4 Hz, 1H), 6.20 (m, 1H), 6.57 (s, 0.5H), 6.58 (s, 0.5H), 6.84 (m, 1H), 7.28-7.41 (m, 5H).

(16e) Synthesis of 2-((1α,5α,6α)-3-(7-(isobutyl)-1-phenylethyl)amino)-5-(3,4,5-trifluorophenyl)pyrazolo[1,5-a]pyrimidine-2-carbonyl)-3-azabicyclo[3.1.0]hexan-6-yl)acetic acid ethyl ester A mixture of 2-((1α,5α,6α)-3-(5-chloro-7-(isobutyl((S)-1-phenylethyl)amino)pyrazolo[1,5-a]pyrimidine-2-carbonyl)-3-azabicyclo[3.1.0]hexan-6-yl)acetic acid ethyl ester (0.050 g), toluene (0.9 mL), a 2N sodium carbonate aqueous solution (0.12 mL), 3,4,5-trifluorophenyl boronic acid (0.020 g) and tetrakis(triphenylphosphine)palladium (0) (0.015 g) was stirred at 100° C. for 17 hours. The reaction mixture was concentrated under reduced pressure, the residue was purified by silica gel column chromatography (heptane-ethyl acetate system), to obtain a crude product of the title compound.

$^1$H-NMR (500 MHz, CDCl$_3$, mixture of rotamers) δ: 0.78 (m, 3H), 0.89 (m, 3H), 0.92-0.96 (m, 1H), 1.24 (m, 3H), 1.47-1.56 (m, 2H), 1.77 (m, 3H), 1.96 (m, 1H), 2.21-2.34 (m, 2H), 2.81-2.93 (m, 2H), 3.64 (dt, J=12, 4 Hz, 1H), 3.96 (dt, J=12, 4 Hz, 1H), 4.12 (m, 2H), 4.19 (d, J=12 Hz, 1H), 4.35 (dd, J=12, 7 Hz, 1H), 6.25-6.36 (m, 2H), 7.13 (s, 0.5H), 7.14 (s, 0.5H), 7.28-7.54 (m, 5H), 7.66 (m, 2H).

(16f) Synthesis of 2-((1α,5α,6α)-3-(7-(isobutyl((S)-1-phenylethyl)amino)-5-(3,4,5-trifluorophenyl)pyrazolo[1,5-a]pyrimidine-2-carbonyl)-3-azabicyclo[3.1.0]hexan-6-yl)acetic acid A 5N sodium hydroxide aqueous solution (0.15 mL) was added to a mixture of the crude product of 2-((1α,5α,6α)-3-(7-(isobutyl((S)-1-phenylethyl)amino)-5-(3,4,5-trifluorophenyl)pyrazolo[1,5-a]pyrimidine-2-carbonyl)-3-azabicyclo[3.1.0]hexan-6-yl)acetic acid ethyl ester obtained in (16e) and ethanol (1 mL) and stirred at room temperature for 1 hour. 5N Hydrochloric acid (0.15 mL) and water were added, the precipitate was collected by filtration, washed with water and dried under reduced pressure. The title compound (0.042 g) was obtained as a white solid.

$^1$H-NMR (500 MHz, CDCl$_3$, mixture of rotamers) δ: 0.78 (m, 3H), 0.90 (m, 3H), 0.93-0.98 (m, 1H), 1.48-1.54 (m, 2H), 1.76 (m, 3H), 1.91-1.98 (m, 1H), 2.27-2.38 (m, 2H), 2.82-2.93 (m, 2H), 3.64 (dt, J=13, 4 Hz, 1H), 3.96 (br.d, J=12 Hz, 1H), 4.20 (d, J=13 Hz, 1H), 4.37 (t, J=12 Hz, 1H), 6.32 (m, 1H), 6.35 (s, 0.5H), 6.36 (s, 0.5H), 7.12 (s, 0.5H), 7.13 (s, 0.5H), 7.27-7.34 (m, 5H), 7.66 (m, 2H).

Example 17

Synthesis of 2-(1-(7-((2-chloro-6-fluorophenyl)(methyl)amino)-5-(3,4,5-trifluorophenyl)pyrazolo[1,5-a]pyrimidine-2-carbonyl)piperidin-4-yl)acetic acid

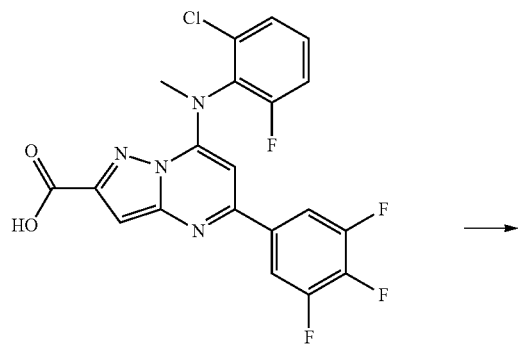

Example 13-(13d)

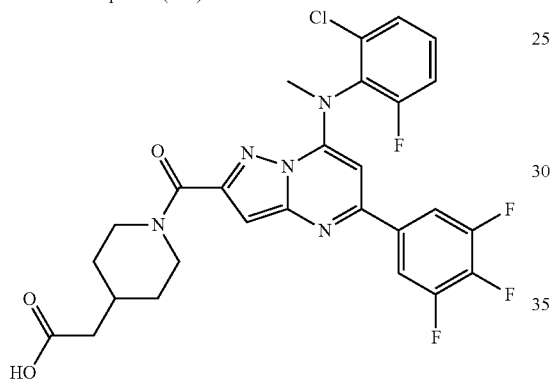

(XVII)

A mixture of 7-((2-chloro-6-fluorophenyl)(methyl)amino)-5-(3,4,5-trifluorophenyl)pyrazolo[1,5-a]pyrimidine-2-carboxylic acid (Example 13-(13d)) (0.023 g), 4-piperidine acetic acid ethyl ester (CAS No. 59184-90-6) (0.012 g), HOBT (0.012 g), WSC (0.015 g), triethylamine (0.030 mL) and DMF (2 mL) was stirred at 40° C. for 3 hours. The reaction mixture was concentrated under reduced pressure, the residue was purified by silica gel column chromatography (heptane-ethyl acetate system), to obtain a crude product of 2-(1-(7-((2-chloro-6-fluorophenyl)(methyl)amino)-5-(3,4,5-trifluorophenyl)pyrazolo[1,5-a]pyrimidine-2-carbonyl)piperidin-4-yl)acetic acid ethyl ester. Ethanol (1.5 mL) and a 5N sodium hydroxide aqueous solution (0.100 mL) were added thereto and stirred at room temperature for 1 hour, to which 5N hydrochloric acid was added. The reaction mixture was concentrated under reduced pressure and the residue was purified by reverse phase high performance liquid chromatography (acetonitrile-water system), to obtain the title compound (22 mg).

$^1$H-NMR (400 MHz, CD$_3$OD) δ: 0.83-0.97 (m, 1H), 1.13 (qd, J=12, 4 Hz, 1H), 1.63 (d, J=13 Hz, 1H), 1.81 (d, J=13 Hz, 1H), 1.91-2.05 (m, 1H), 2.15-2.32 (m, 2H), 2.67-2.70 (m, 2H), 3.60 (s, 3H), 4.11 (d, J=13 Hz, 1H), 4.54 (d, J=13 Hz, 1H), 6.81 (s, 1H), 7.06 (s, 1H), 7.18 (br.t, J=8 Hz, 1H), 7.33-7.42 (m, 2H), 8.00-8.09 (m, 2H).

Example 18

Synthesis of 2-((3R*,4S*)-1-(5-(4-chloro-3,5-difluorophenyl)-7-(isopropyl(propyl)amino)pyrazolo[1,5-a]pyrimidine-2-carbonyl)-3-methylpiperidin-4-yl)acetic acid

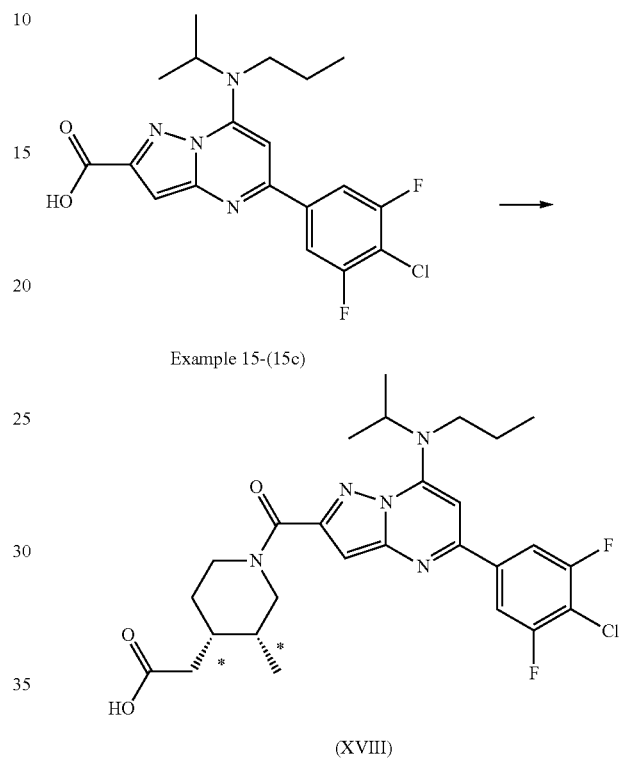

Example 15-(15c)

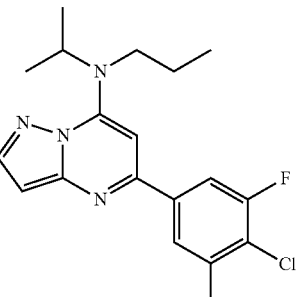

(XVIII)

Triethylamine (0.060 mL) was added to a mixture of 5-(4-chloro-3,5-difluorophenyl)-7-(isopropyl(propyl)amino)pyrazolo[1,5-a]pyrimidine-2-carboxylic acid (0.030 g) (Example 15-(15c)), 2-((3R*,4S*)-3-methylpiperidin-4-yl)acetic acid isopropyl ester hydrochloride (0.020 g) (Production Example 5), HOBT (0.028 g), WSC (0.040 g) and DMF (0.6 mL) and stirred at room temperature for 17 hours. Water and ethyl acetate were added to the reaction mixture to separate the organic layer, which was concentrated under a nitrogen gas stream. The residue was purified by silica gel column chromatography (heptane-ethyl acetate system), to obtain a crude product of 2-((3R*,4S*)-1-(5-(4-chloro-3,5-difluorophenyl)-7-(isopropyl(propyl)amino)pyrazolo[1,5-a]pyrimidine-2-carbonyl)-3-methylpiperidin-4-yl)acetic acid isopropyl ester. Ethanol (0.700 mL) and a 5N sodium hydroxide aqueous solution (0.100 mL) were added thereto and stirred at room temperature for 3.5 hours, to which 5N hydrochloric acid (0.100 mL) was added. The precipitate was collected by filtration, washed with water and dried under reduced pressure, to obtain the title compound (36 mg).

$^1$H-NMR (400 MHz, DMSO-d$_6$, mixture of rotamers) δ: 0.73-0.87 (m, 6H), 1.23-1.29 (m, 6H), 1.40-1.58 (m, 4H), 1.83-2.22 (m, 4H), 2.99-3.44 (m, 2H), 3.60-3.71 (m, 2H), 3.99-4.31 (m, 2H), 4.95-5.06 (m, 1H), 6.72 (s, 0.45H), 6.74 (s, 0.55H), 6.99 (s, 1H), 8.17 (d, J=9 Hz, 2H).

Mass spectrum (ESI) m/z: 548 (M+H)$^+$

Reference Example 1

Synthesis of (S)-2-(1-(7-(methyl(1-phenylethyl)amino)-5-(3,4,5-trifluorophenyl)pyrazolo[1,5-a]pyrimidine-2-carbonyl)piperidin-4-yl)acetic

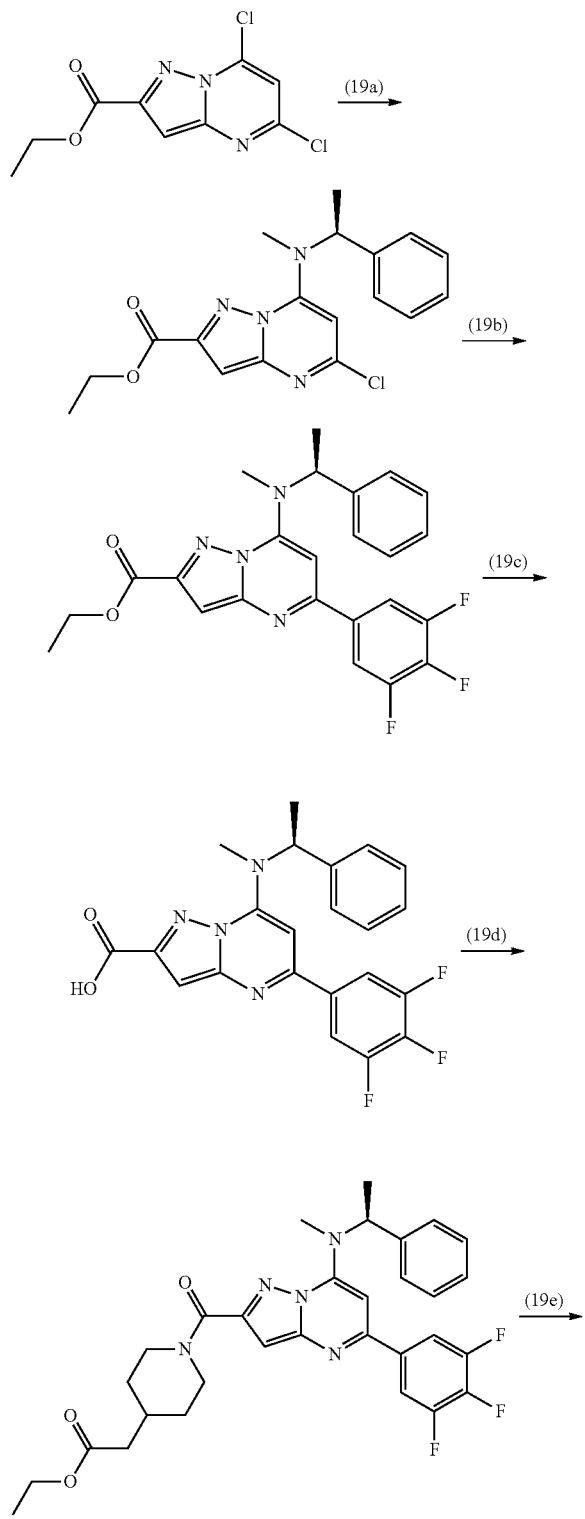

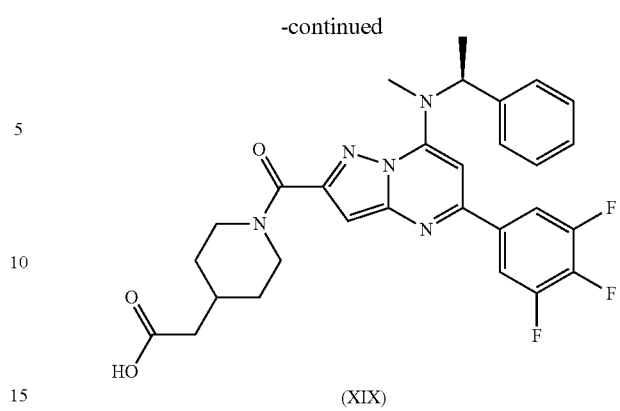

(XIX)

(19a) Synthesis of (S)-5-chloro-7-(methyl(1-phenylethyl)amino)pyrazolo[1,5-a]pyrimidine-2-carboxylic acid ethyl ester (S)—N-Methyl-1-phenylethanamine (CAS No. 19131-99-8) (1.716 g) and triethylamine (3.22 mL) were added to a solution of 5,7-dichloropyrazolo[1,5-a]pyrimidine-2-carboxylic acid ethyl ester (3 g) in THF (95 mL) and stirred at room temperature overnight. Ethyl acetate and water were added to separate the solution. The organic layer was washed with saline and dried over anhydrous magnesium sulfate. The drying agent was filtered off and the filtrate was concentrated under reduced pressure. The residue was purified by silica gel column chromatography (heptane-ethyl acetate system), to obtain the title compound (4.08 g).
$^1$H-NMR (400 MHz, CDCl$_3$) δ: 1.41 (t, J=7 Hz, 3H), 1.75 (d, J=7 Hz, 3H), 2.83 (s, 3H), 4.43 (qd, J=7, 1 Hz, 2H), 6.03 (s, 1H), 6.60 (q, J=7 Hz, 1H), 6.97 (s, 1H), 7.28-7.45 (m, 5H).

(19b) Synthesis of (S)-7-(methyl)(1-phenylethyl)amino)-5-(3,4,5-trifluorophenyl)pyrazolo[1,5-a]pyrimidine-2-carboxylic acid ethyl ester A 2N sodium carbonate aqueous solution (40 mL) was added to a mixture of (S)-5-chloro-7-(methyl(1-phenylmethyl)amino)pyrazolo[1,5-a]pyrimidine-2-carboxylic acid ethyl ester (13.95 g), toluene (150 mL), ethanol (15 mL), 3,4,5-trifluorophenylboronic acid (7.5 g) and tetrakis(triphenylphosphine)palladium (0) (2.5 g) and stirred at 100° C. for 75 minutes. Ethyl acetate and water were added to the reaction mixture, which was filtered to remove the precipitate. The filtrate was separated, the organic layer was washed with saline and subsequently dried over anhydrous magnesium sulfate. The drying agent was filtered off and the filtrate was concentrated under reduced pressure. The residue was purified by silica gel column chromatography (heptane-ethyl acetate system), to obtain the title compound (16.23 g).
$^1$H-NMR (400 MHz, CDCl$_3$) δ: 1.43 (t, J=7 Hz, 3H), 1.78 (d, J=7 Hz, 3H), 2.91 (s, 3H), 4.45 (qd, J=7, 3 Hz, 2H), 6.33 (s, 1H), 6.68 (q, J=7 Hz, 1H), 7.12 (s, 1H), 7.29-7.39 (m, 3H), 7.42-7.45 (m, 2H), 7.69 (dd, J=9, 7 Hz, 2H).

(19c) Synthesis of (S)-7-(methyl(1-phenylethyl)amino)-5-(3,4,5-trifluorophenyl)pyrazolo[1,5-a]pyrimidine-2-carboxylic acid Water (5 mL) and a 4N lithium hydroxide aqueous solution (0.653 mL) were added to a solution of (S)-7-

(methyl(1-phenylethyl)amino)-5-(3,4,5-trifluorophenyl)pyrazolo[1,5-a]pyrimidine-2-carboxylic acid ethyl ester (0.791 g) in 1,4-dioxane (40 mL) and stirred at room temperature for 3 days. The solvent was removed under reduced pressure, water (20 mL) was added to the residue, to which 5N hydrochloric acid (0.5 mL) was added while stirring. The precipitate was collected by filtration, dried under reduced pressure, to obtain the title compound (678 mg).

$^1$H-NMR (500 MHz, DMSO-d$_6$) δ: 1.69 (d, J=7 Hz, 3H), 2.91 (s, 3H), 6.77 (q, J=7 Hz, 1H), 6.89 (s, 1H), 7.01 (s, 1H), 7.31 (m, 1H), 7.39 (t, J=7 Hz, 2H), 7.46 (d, J=7 Hz, 2H), 8.18-8.22 (m, 2H), 13.30 (br.s, 1H).

(19d) Synthesis of (S)-2-(1-(7-(methyl(1-phenylethyl)amino)-5-(3,4,5-trifluorophenyl)pyrazolo[1,5-a]pyrimidine-2-carbonyl)piperidin-4-yl)acetic acid ethyl ester HOBT (2.68 g), WSC (3.35 g), 4-piperidine acetic acid ethyl ester (CAS No. 59184-90-6) (2.226 g) and triethylamine (4.18 mL) were added sequentially to a solution of (S)-7-(methyl(1-phenylethyl)amino)-5-(3,4,5-trifluorophenyl)pyrazolo[1,5-a]pyrimidine-2-carboxylic acid (4.26 g) in DMF (50 mL) and stirred at room temperature for 15 hours. Ethyl acetate (500 mL) was added to the reaction mixture, and the organic layer was washed 3 times with water (300 mL) and dried over anhydrous magnesium sulfate. The drying agent was filtered off and the filtrate was concentrated under reduced pressure. The residue was purified by silica gel column chromatography (heptane-ethyl acetate system), to obtain the title compound (5.175 g).

$^1$H-NMR (500 MHz, CDCl$_3$, mixture of rotamers) δ: 1.07-1.12 (m, 1H), 1.22-1.34 (m, 4H), 1.50-1.63 (m, 1H), 1.70-1.72 (m, 3H), 1.80-1.86 (m, 1H), 2.02-2.09 (m, 1H), 2.13-2.25 (m, 2H), 2.76-2.83 (m, 1H), 2.87 (s, 3H), 2.99-3.07 (m, 1H), 4.13 (q, J=7 Hz, 2H), 4.54-4.61 (m, 1H), 4.72-4.88 (m, 1H), 6.31 (s, 1H), 6.73-6.84 (m, 1H), 6.93-6.95 (m, 1H), 7.28-7.40 (m, 5H), 7.66-7.73 (m, 2H).

(19e) Synthesis of (S)-2-(1-(7-(methyl(1-phenylethyl)amino)-5-(3,4,5-trifluorophenyl)pyrazolo[1,5-a]pyrimidine-2-carbonyl)piperidin-4-yl)acetic acid A mixture of (S)-2-(1-(7-(methyl(1-phenylethyl)amino)-5-(3,4,5-trifluorophenyl)pyrazolo[1,5-a]pyrimidine-2-carbonyl)piperidin-4-yl)acetic acid ethyl ester (1.42 g), ethanol (10 mL) and a 4N lithium hydroxide aqueous solution (1.225 mL) was stirred at room temperature for 4 hours. The reaction mixture was concentrated under reduced pressure, the residue was diluted with 1,4-dioxane, a 4N lithium hydroxide aqueous solution (1.2 mL) was added thereto and the mixture was stirred with heating at 50° C. for 90 minutes. The reaction mixture was concentrated under reduced pressure and the residue was diluted with ethyl acetate to separate the solvents. The organic layer was extracted with a 1N sodium hydroxide aqueous solution, aqueous layers were combined and washed with ethyl acetate. The aqueous layer was neutralized with 2N hydrochloric acid and extracted with ethyl acetate. The organic layer was washed with saline and dried over anhydrous sodium sulfate. The drying agent was filtered off and the filtrate was concentrated under reduced pressure. The residue was diluted with a diethyl ether:methanol (3:1) solution and sonicated. The precipitate was collected by filtration and dried under reduced pressure, to obtain the title compound (1.134 g).

$^1$H-NMR (400 MHz, CDCl$_3$, mixture of rotamers) δ; 1.05-1.38 (m, 2H), 1.50-1.66 (m, 1H), 1.69-1.73 (m, 3H), 1.83-1.90 (m, 1H), 1.97-2.11 (m, 1H), 2.17-2.31 (m, 2H), 2.75-2.84 (m, 1H), 2.87 (s, 3H), 2.98-3.07 (m, 1H), 4.54-4.65 (m, 1H), 4.73-4.81 (m, 1H), 6.32 (s, 1H), 6.71-6.86 (m, 1H), 6.92-6.95 (m, 1H), 7.27-7.40 (m, 5H), 7.66-7.74 (m, 2H).

Reference Example 2

X-ray diffraction experiment on 2-((3R,4S)-1-(5-(4-chloro-3,5-difluorophenyl)-7-((2-fluoro-6-methylphenyl)(methylamino)pyrazolo[1,5-a]pyrimidine-2-carbonyl)-3-methoxypiperidin-4-yl)acetic acid Solid 2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid obtained in Example 10-(10n) was dissolved in methanol and recrystallized by the vapor diffusion method with acetonitrile as reservoir. An X-ray diffraction experiment was carried out using the obtained single crystal. Crystallographic data and structural analysis results are shown in Table 1 and the atomic coordinate data are shown in Table 2. These results identified the absolute structure of the title compound.

TABLE 1

| | |
|---|---|
| Measurement temperature | 100 K |
| Wavelength | 1.54187 Å |
| Crystal system, space group | Tetragonal system, P4$_1$2$_1$2 |
| Lattice constant | a = 10.07760 (8) Å |
| | c = 56.3508 (7) Å |
| Volume | 5722.88 (10) Å$^3$ |
| Z value, Calculated density | 8, 1.397 g/cm$^3$ |
| Crystal size | 0.2 × 0.2 × 0.1 mm |
| Number of total reflections/ Number of unique reflections | 36332/5658 |
| Completeness | 98.4% |
| Phase determination | Direct method (SHELXT Version 2014/5) |
| Refinement method | Least-squares method on F$^2$ |
| Number of data/Number of parameters | 5658/383 |
| Goodness of fit | 1.054 |
| R Value (All data) | 0.0558 |
| R Value (I > 2σ (I)) | 0.0549 |
| Flack parameter | 0.021 (5) |
| Maximum and minimum difference peaks | 1.09 and −0.50 e/Å$^3$ |

TABLE 2

| Atom | x | y | z | Beq |
|---|---|---|---|---|
| C18 | 0.22435 (12) | 1.18031 (10) | 0.76648 (2) | 3.54 (2) |
| F7 | 0.4747 (3) | 1.0360 (3) | 0.77268 (5) | 3.89 (5) |
| F9 | 0.0801 (3) | 1.0411 (3) | 0.72860 (4) | 3.56 (5) |
| F26 | 0.4086 (5) | 0.2758 (5) | 0.71424 (8) | 7.69 (11) |
| O30 | 0.8904 (3) | 0.5016 (3) | 0.64474 (5) | 2.82 (5) |
| O37 | 0.8890 (3) | 0.1675 (3) | 0.68629 (6) | 3.74 (6) |
| O41 | 1.0257 (3) | −0.2595 (3) | 0.68278 (6) | 3.65 (6) |
| O42 | 0.9183 (3) | −0.2401 (3) | 0.64825 (6) | 3.17 (5) |
| N13 | 0.5061 (3) | 0.5220 (3) | 0.68112 (6) | 2.31 (5) |
| N14 | 0.5701 (3) | 0.4396 (3) | 0.66596 (6) | 2.35 (5) |
| N18 | 0.5449 (3) | 0.7086 (3) | 0.70694 (6) | 2.49 (5) |
| N19 | 0.2959 (3) | 0.4237 (4) | 0.67562 (8) | 3.41 (7) |
| N31 | 0.7970 (3) | 0.2975 (3) | 0.64425 (6) | 2.41 (5) |
| C1 | 0.3639 (4) | 0.8225 (4) | 0.72514 (7) | 2.43 (6) |
| C2 | 0.4429 (4) | 0.8765 (4) | 0.74272 (7) | 2.71 (6) |
| C3 | 0.3979 (4) | 0.9838 (4) | 0.75560 (7) | 2.75 (6) |
| C4 | 0.2756 (4) | 1.0421 (4) | 0.75118 (7) | 2.63 (6) |

TABLE 2-continued

| Atom | x | y | z | Beq |
|---|---|---|---|---|
| C5 | 0.1986 (4) | 0.9859 (4) | 0.73357 (7) | 2.73 (6) |
| C6 | 0.2383 (4) | 0.8765 (4) | 0.72066 (7) | 2.52 (6) |
| C10 | 0.4149 (4) | 0.7127 (4) | 0.71002 (7) | 2.50 (6) |
| C11 | 0.3251 (4) | 0.6201 (4) | 0.69996 (8) | 2.92 (7) |
| C12 | 0.3707 (4) | 0.5195 (4) | 0.68562 (8) | 2.83 (7) |
| C15 | 0.6980 (4) | 0.4784 (4) | 0.66795 (7) | 2.31 (6) |
| C16 | 0.7161 (4) | 0.5825 (4) | 0.68390 (7) | 2.44 (6) |
| C17 | 0.5904 (4) | 0.6122 (4) | 0.69233 (7) | 2.35 (6) |
| C20 | 0.3443 (4) | 0.2896 (4) | 0.67243 (9) | 3.28 (8) |
| C21 | 0.3962 (5) | 0.2189 (5) | 0.69117 (10) | 3.92 (9) |
| C22 | 0.4368 (5) | 0.0866 (5) | 0.68811 (12) | 4.72 (11) |
| C23 | 0.4222 (6) | 0.0297 (5) | 0.66631 (13) | 5.28 (14) |
| C24 | 0.3727 (5) | 0.0979 (5) | 0.64723 (12) | 4.75 (13) |
| C25 | 0.3334 (4) | 0.2318 (5) | 0.65018 (10) | 3.75 (9) |
| C27 | 0.2849 (4) | 0.3080 (4) | 0.63103 (7) | 2.51 (6) |
| C28 | 0.1509 (5) | 0.4311 (6) | 0.67950 (15) | 6.24 (18) |
| C29 | 0.8015 (4) | 0.4240 (3) | 0.65189 (7) | 2.30 (6) |
| C32 | 0.7215 (4) | 0.1909 (4) | 0.65550 (8) | 2.62 (6) |
| C33 | 0.8179 (4) | 0.0975 (4) | 0.66828 (8) | 3.03 (7) |
| C34 | 0.9203 (4) | 0.0409 (4) | 0.65113 (9) | 3.17 (7) |
| C35 | 0.9901 (4) | 0.1539 (4) | 0.63775 (8) | 3.13 (7) |
| C36 | 0.8918 (4) | 0.2507 (4) | 0.62672 (8) | 2.84 (7) |
| C38 | 0.8171 (6) | 0.1866 (6) | 0.70746 (10) | 4.94 (11) |
| C39 | 1.0218 (5) | −0.0476 (4) | 0.66358 (12) | 4.46 (11) |
| C40 | 0.9887 (4) | −0.1923 (4) | 0.66628 (8) | 3.07 (7) |

Test Example 1 Intracellular Calcium Concentration Measurement

Human embryonic kidney cell line HEK293 cells cultured using DMEM culture medium (Invitrogen) with 3% fetal bovine serum (3% FBS)-added was prepared to have a concentration of $2 \times 10^5$ cells/mL, and plated in a type I collagen-coated 384-well black plate (clear bottom) (Greiner) so as to be 25 μL/well and cultured in a CO2 incubator overnight. FLIPR Calcium Assay Kit (Molecular Devices) prepared with Hanks-20 mM Hepes buffer (pH 7.4) was added to the cells so as to be 25 μL/well and cultured in the CO2 incubator for 1 hour. Trypsin (SIGMA-ALDRICH, catalog number: T8816, Enzyme Commission Number 3.4.21.4) prepared so as to be 5 U/mL as final concentration (BAEE unit) with Hanks-20 mM Hepes buffer (pH 7.4) was added to a 384-well deep well polypropylene plate (Greiner) to be an agonist reagent plate. Thirty minutes before the measurement using FDSS6000 (Hamamatsu Photonics K.K.), a test compound prepared with Hanks-20 mM Hepes buffer (pH 7.4) was added to the cell so as to be 8 μL/well. The cell plate to which the test compound was added and the reagent plate were set on FDSS6000, 22 μL/well of the agonist solution was added from the reagent plate, and the change in intracellular calcium concentration was measured with a CCD camera. The measurement was carried out at 37° C. for 120 seconds and the addition of reagent from the reagent plate to the cell plate was carried out using a built-in 384-well automatic dispenser of FDSS6000.

Table 3 shows the inhibitory activity on intracellular calcium elevation (IC50 (nM)) of the test compounds. Note that Reference Example 1 in Table 3 is the compound represented by formula (XIX) synthesized in the above Reference Example 1 (hereinafter, also referred to as Compound (XIX)). Additionally, the "Comparative Compound" in Table 3 is the compound described in Patent Literature 4 represented by the following formula (XX) (I-343; hereinafter, also referred to as Compound (XX)).

(XX)

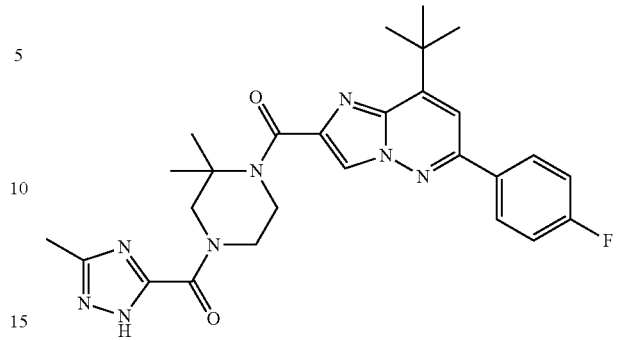

TABLE 3

| Examples | Inhibitory activity on intracellular calcium elevation (IC50 (nM)) |
|---|---|
| 1 | 2.57 |
| 2 | 7.54 |
| 3 | 8.73 |
| 4 | 7.32 |
| 5 | 2.45 |
| 6 | 2.79 |
| 7 | 1.74 |
| 8 | 25.11 |
| 9 | 4.90 |
| 10 | 3.46 |
| 11 | 6.88 |
| 12 | 4.77 |
| 13 | 4.00 |
| 14 | 5.08 |
| 15 | 12.82 |
| 16 | 26.32 |
| 17 | 3.27 |
| 18 | 7.38 |
| Reference Example 1 | 8.27 |
| Comparative Compound | 24.21 |

Test Example 2 Measurement of PAR2 Agonist-Induced Salivation in Mouse

The test compound was added to a 0.5% carboxymethyl cellulose solution to which 2% DMSO was added, so as to have the final concentration of 0.3 mg/mL, thereby preparing an administration solution containing the test compound. The administration solution containing the test compound (10 mL/kg) was orally administered to C57BL/6J male mice (Charles River), 6-10 weeks of age, using an oral sonde and a syringe. Forty-five minutes after the administration of the test compound, 10 mL/kg of a 20% (w/v) urethane solution was intraperitoneal administered to the mice which were then anesthetized. Sixty minutes after the administration of the test compound, 10 mL/kg of a 0.1 mg/mL SLIGRL-NH2 (SEQ ID NO: 2) solution was intraperitoneally administered as the PAR2 agonist and a cotton ball was immediately placed in the oral cavity of the mouse to collect the saliva. Ten minutes after the administration of the PAR2 agonist, the cotton ball was removed and weighed to measure the amount of saliva secreted.

Table 4 shows the inhibitory activity on the PAR2-dependent saliva secretion (%) of the test compounds. Note that Reference Example 1 in Table 4 is Compound (XIX). Additionally, Comparative Compound in Table 4 is Compound (XX).

TABLE 4

| Examples | Inhibitory activity on the PAR2-dependent saliva secretion (%) |
|---|---|
| 1 | 91.5 |
| 2 | 91.3 |
| 3 | 86.7 |
| 4 | 87.1 |
| 5 | 94.5 |
| 6 | 97.0 |
| 7 | 96.0 |
| 8 | 98.1 |
| 9 | 96.0 |
| 10 | 92.2 |
| 11 | 97.8 |
| 12 | 98.8 |
| 13 | 95.0 |
| 14 | 92.5 |
| 15 | 91.1 |
| 16 | 98.2 |
| 17 | 94.9 |
| 18 | 95.1 |
| Reference Example 1 | 95.9 |
| Comparative Compound | 98.0 |

Test Example 3 Evaluation in Mouse Dermatitis Model

The test compound was added to a 0.5% carboxymethyl cellulose solution so as to have the final concentration of 0.3 mg/mL, thereby preparing an administration solution containing the test compound. Hapten used was 2,4-dinitrofluorobenzene (DNFB, Wako Pure Chemical Industries).

Twenty-five (25) μL of a solution of DNFB diluted to 0.4% with a mixed solvent of acetone and an olive oil in a volume ratio of 2:1 was applied twice to the shaved abdominal region of BALB/c male mice (Charles River), 6-10 weeks of age, over a period of 2 days to create the sensitization. Four days after the sensitization, on the first day, 20 μL of a solution of DNFB diluted to 0.2% with a mixed solvent of acetone and an olive oil in a volume ratio of 2:1 was applied to the right auricle of the mouse to induce dermatitis. Eight hours after the induction of dermatitis, the administration solution containing the test compound (10 mL/kg) was orally administered to the mouse. On the day following the induction of dermatitis, the right auricle thickness of the mouse was measured using a thickness gauge to evaluate the action of the test compound.

Table 5 shows the inhibitory activity (%) of the test compound on the auricular swelling. Note that Reference Example 1 in Table 5 is Compound (XIX).

TABLE 5

| Examples | Inhibitory activity on auricle swelling (%) |
|---|---|
| 7 | 61.6 |
| 10 | 52.9 |
| 15 | 17.4 |
| Reference Example 1 | 22.3 |

Test Example 4 Evaluation in Model Mouse for Enteritis

Generally, the bowel length is known to be shorter during enteritis (Maxwell, J. R. et al. Curr. Protoc. Pharmacol. Chapter 5: Unit 5.58, 2009). The bowel length in an enteritis model was measured to evaluate the effect of the test compound.

The test compound was added to a 0.5% carboxymethyl cellulose solution so as to have a final concentration of 0.1 mg/mL, thereby preparing an administration solution containing the test compound. Hapten used was 4-ethoxymethylene-2-phenyloxazol-5-one (OXA, SIGMA-ALDRICH).

One hundred (100) μL of a solution of OXA diluted to 0.3% with ethanol was applied to the shaved abdominal region of BALB/c male mice (Charles River), 6-10 weeks of age, to create the sensitization. Five days after the sensitization, OXA was intrarectally administered to induce an enteritis reaction. More specifically, a syringe equipped with a sonde for oral administration was inserted into the anus of the mouse anesthetized by the inhalation of isoflurane at a concentration of 4-5% and 50 μL of the OXA solution adjusted to 1% with a solvent of 50% ethanol/50% distilled water was administered into the rectum.

One hour before and on the day following the induction of enteritis, the administration solution containing the test compound (10 mL/kg) was orally administered twice in total to the mice. Two days after the induction of enteritis, the mice were euthanized by cervical dislocation and subsequently the cecum to the anus was collected to measure the combined length of the colon and the rectum using a ruler, thereby evaluating the action of the test compound.

Table 6 shows the inhibitory activity (%) of the test compound on the shortening of the bowel. Note that Reference Example 1 in Table 6 is Compound (XIX).

TABLE 6

| Examples | Inhibitory activity on bowel shortening (%) |
|---|---|
| 1 | 60.4 |
| 2 | 69.7 |
| 5 | 105.5 |
| 6 | 79.6 |
| 8 | 55.0 |
| 13 | 62.2 |
| 16 | 74.5 |
| Reference Example 1 | 37.3 |

Test Example 5 Model for Mite Antigen-Induced Atopic Dermatitis

The dermatitis model induced by the application of a mite antigen to Nc mouse is known to demonstrate clinical symptoms and histological findings highly analogous to human atopic dermatitis (Allergology International, 56, p 139-148 (2007)). The dermatitis condition of the model was observed to evaluate the effect of the test compound on the dermatitis.

<Method>

A 4 w/v % SDS solution (0.15 mL/mouse) was first applied to the dorsal region and auricle region of 8-week old male NC/NgaTndCrlj mice (Charles River Laboratories Japan, Inc.) under isoflurane inhalation anesthesia. About 3 hours after the application of the 4 w/v % SDS solution (0.15 mL/mouse), a 1 mL-polypropylene disposable syringe (Terumo Corporation) was filled with Bio stir AD (Biostir Inc.) as a mite antigen ointment which was applied to the dorsal region and auricle region (0.1 mL/mouse). Every 2 or 3 days, the 4 w/v % SDS solution (0.15 mL/mouse) and Biostir AD were applied to a total of 8 times including the initial application by the same method to induce dermatitis. After inducing the dermatitis, the conditions of the skin at the application sites (assessments other than itching behavior) were observed and the dermatitis findings 1) to 5) described below were scored based on the evaluation criteria for the clinical symptoms of human atopic dermatitis. Note that the scoring of the dermatitis findings 1) to 5) has 0 for no symptom, 1 for mild, 2 for moderate and 3 for severe. The dermatitis score of each individual is the total of the dermatitis findings 1) to 5). Grouping (15 mice per group) was carried out randomly so that each group had substantially the same (no statistically significant difference) average dermatitis score (total) and average body weight.

For 14 days from the day on which the grouping was carried out, an administration solution containing the test compound (10 mL/kg) was orally administered to the mouse once a day (14 times in total). The administration solution was a 0.5% carboxymethyl cellulose solution containing 10 mmol/L sodium hydroxide and made up into three types of solution having test compound concentrations of 0.3, 1 or 3 mg/mL. In the morning on the day of grouping (day 0), 4 days, 7 days, 11 days and 14 days after starting the administration, the skin condition at the mite antigen administered sites was observed for all cases to score again the findings of dermatitis.

Table 7 shows the scores 0 day, 4 days, 7 days, 11 days and 14 days after starting the administration.

<Findings of Dermatitis>

1) Itching behavior: Behavior was observed for 2 minutes, during which the itching behavior at the induced sites was observed.
   0: No symptoms: Condition with no itching behavior at the induced sites.
   1: Mild: Continuous itching behavior seen two or more times during the period but not exceeding about 1 minute cumulatively.
   2: Moderate: Behavior exceeding about 1 minute but not exceeding about 1 minute and a half cumulatively.
   3: Severe: Behavior of continuous itching exceeding about 1 minute and a half or for 2 minutes cumulatively.
2) Redness-bleeding: Redness and bleeding symptoms at the induced sites were observed.
   0: No symptoms: Condition with no redness or bleeding symptom at the induced sites.
   1: Mild: Localized conditions with redness and bleeding symptoms identified at the induced sites or with no bleeding identified caused by continuous scratching.
   2: Moderate: Conditions with redness and bleeding symptoms identified scattered around the induced sites or redness and bleeding symptoms caused by continuous scratching identified locally.
   3: Severe: Conditions with redness and bleeding symptoms identified throughout the induced sites or redness and bleeding symptoms with continuous scratching spreading over a wide range.
3) Swelling: Quantitative observation of the auricle induced site was carried out.
   0: No symptoms: Condition with no thickening identified of the right or left auricle.
   1: Mild: Condition with a slight thickening of either the right or left auricle
   2: Moderate: Condition with distinct thickening and puffiness of both auricles.
   3: Severe: Condition with distinct thickening, puffiness and deformation identified for both auricles and hardening sensed when touched with fingers.
4) Scratch-tissue loss: Scratch and tissue loss symptoms at the induced sites were observed.
   0: No symptoms: Condition with no scratches or tissue loss identified at the induced sites.
   1: Mild: Condition with localized scratches and tissue loss identified at the induced sites, non-continuous scratches are identified but tissue loss is not identified.
   2: Moderate: Condition with scratches and tissue loss identified scattered around the induced sites or small-scale continuous scratches are identified but tissue loss is not identified.
   3: Severe: Condition with scratches and tissue loss symptoms identified throughout the induced sites or continuous scratches are spread over a wide range and tissue loss is identified.
5) Scab formation-dryness: Scab formation and dryness symptoms at the induced sites were observed.
   0: No symptom: Condition with no scab formation or dryness symptoms at the induced sites.
   1: Mild: Condition with localized scab formation and dryness symptoms identified at the induced sites and slight skin-whitening and keratinous peeling identified at the induced sites.
   2: Moderate: Condition with scab formation and dryness symptoms scattered around, or keratinous peeling clearly identifiable at the induced sites.
   3: Severe: Condition with scab formation and dryness symptoms identified, or keratinous peeling clearly identifiable throughout the induced sites.

TABLE 7

| | | Date of evaluation (after starting administration) | | | | |
|---|---|---|---|---|---|---|
| | | 0 | 4 | 7 | 11 | 14 |
| Vehicle | | 9.8 ± 0.5 | 9.5 ± 0.5 | 9.4 ± 0.6 | 8.1 ± 0.8 | 8.2 ± 0.8 |
| Example 10 | 3 mg/kg | 9.7 ± 0.5 | 9.1 ± 0.5 | 8.6 ± 0.7 | 6.7 ± 0.7 | 5.4 ± 0.7 |
| | 10 mg/kg | 9.3 ± 0.6 | 8.6 ± 0.9 | 7.7 ± 0.8 | 7.1 ± 1.0 | 5.9 ± 0.9 |
| | 30 mg/kg | 9.3 ± 0.6 | 8.7 ± 0.7 | 7.8 ± 0.8 | 6.5 ± 0.8 | 5.0 ± 0.8 |

Test Example 6 Mouse Model of Skin Barrier Disruption Induced by Tape Stripping The effect of the test compounds on the skin barrier functions was evaluated using a model with skin barrier disruption induced by tape stripping. Trans-epidermal water loss (TEWL) is an evaluation indicator of the skin barrier functions (Journal of Investigative Dermatology, 126, p 2074-2086 (2006)).

<Method>

Seven-week old male Hos: HR-1 mice (Hoshino Laboratory Animals, Inc.) were subjected to the test (n=10 for each treatment). For oral administration, solutions of test compounds with different concentrations were prepared as follows.

(1) Using a 0.5% methylcellulose solution containing 1.7 mmol/L sodium hydroxide, a solution of the test compound was prepared so that the concentration of the test compound was 1 mg/mL.

(2) The solution of the test compound prepared in (1) was diluted with a 0.5% methylcellulose solution to prepare a solution of the test compound so that the concentration of the test compound was 0.3 mg/mL. TEWL was measured before the test compound was administered (termed as TEWL [pre]). After the TEWL [pre] was measured, the solution of the test compound adjusted as in (1) or (2) was administered orally (dose: 10 mL/kg). One hour after the test compound administration, the skin barrier at the mouse abdominal region was disrupted by tape stripping treatment. TEWL immediately after and 1 hour after the tape stripping were measured (termed as TEWL [0 hour], TEWL [1 hour], respectively), % Barrier recovery was calculated in accordance with the following formula.

% Barrier Recovery={(TEWL [0 hour]−TEWL [1 hour])/(TEWL [0 hour]−TEWL [pre])}*100

The result was expressed as the average ± standard deviation of the % barrier recovery. For the statistical analysis, Dunnett's multiple comparison test was used and $p<0.05$ was determined as the statistically significant difference.

<Result>

Table 8 shows the results. The administration of the compound of the present invention increased the % barrier recoveries. The results demonstrate the effectiveness of the compounds of the present invention in skin barrier disrupted models.

TABLE 8

| Treatment | | % Barrier recovery |
|---|---|---|
| Vehicle | | 13.1 ± 3.0 |
| Example 10 | 3 mg/kg | 24.2 ± 8.1 |
| | 10 mg/kg | 53.5 ± 4.9* |

*$p < 0.05$ versus Vehicle (Dunnett Test)

INDUSTRIAL APPLICABILITY

As described above, the pyrazolo[1,5-a]pyrimidine compounds according to the present invention or pharmaceutically acceptable salts thereof have the PAR2 inhibitory action. Additionally, the compounds according to the present invention demonstrated the suppressive action on PAR2-dependent saliva secretion and the suppressive activity on the auricular swelling associated with dermatitis on the mice. Thus, the compounds according to the present invention have the potential to be used as the treatment agent for the inflammatory skin diseases to which PAR2 is involved such as atopic dermatitis, contact dermatitis, skin eczema, psoriasis and dry skin dermatitis. Further, the compounds according to the present invention demonstrated the suppressive action on the shortening of the bowel in the mouse enteritis model. Thus, the compounds according to the present invention also have the potential to be used as the treatment agent for the inflammatory bowel diseases to which PAR2 is involved such as ulcerative colitis, Crohn's disease and infectious enteritis.

---

What is claimed is:

1. A compound selected from the group consisting of:

2-((3R*,4S*)-1-(7-((2,6-dimethylphenyl)(methyl)amino)-5-(3,4,5-trifluorophenyl)pyrazolo[1,5-a]pyrimidine-2-carbonyl)-3-fluoropiperidin-4-yl)acetic acid represented by chemical formula (I)

(I)

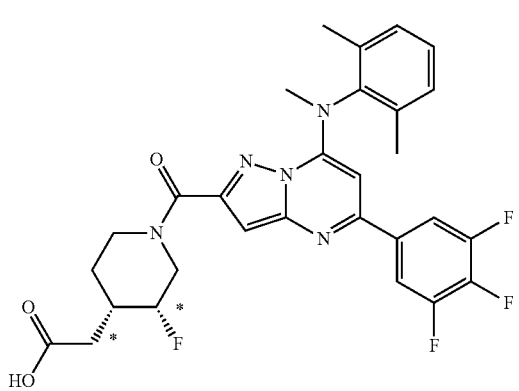

2-((3R*,4S*)-1-(7-((2,6-dimethylphenyl)(methyl)amino)-5-(3,4,5-trifluorophenyl)pyrazolo[1,5-a]pyrimidine-2-carbonyl)-3-methoxypiperidin-4-yl)acetic acid represented by chemical formula (II)

(II)

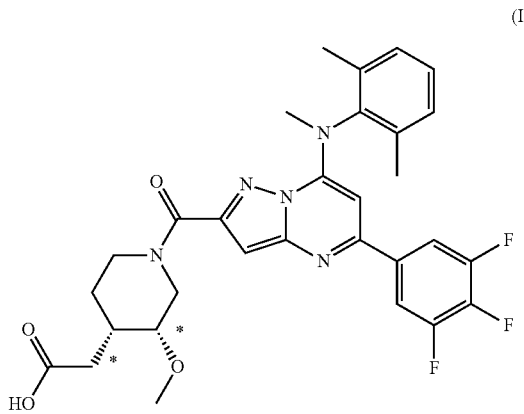

2-((3R*,4S*)-1-(5-(4,4-dimethylcyclohexyl)-7-((2,6-dimethylphenyl)(methyl)amino)pyrazolo[1,5-a]pyrimidine-2-carbonyl)-3-fluoropiperidin-4-yl)acetic acid represented by chemical formula (III)

(III)

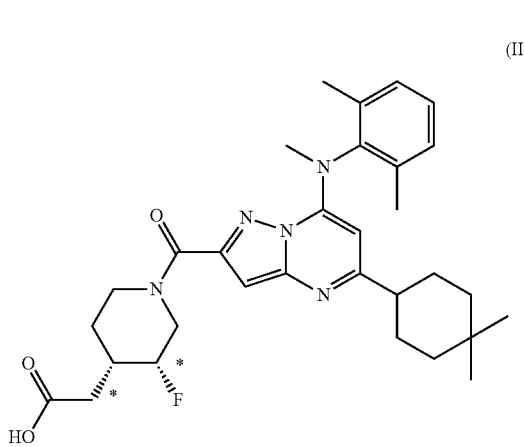

2-((3R*,4S*)-1-(5-(3-chloro-4-fluorophenyl)-7-((2,6-dimethylphenyl)(methyl)amino)pyrazolo[1,5-a]pyrimidine-2-carbonyl)-3-methoxypiperidin-4-yl)acetic acid represented by chemical formula (IV)

(IV)

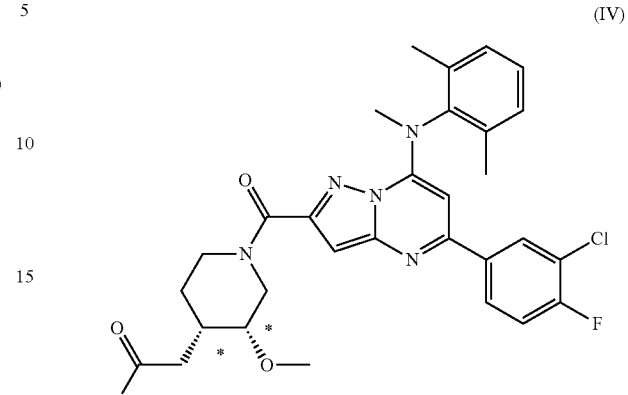

2-((3R*,4S*)-3-fluoro-1-(7-((2-methoxy-6-methylphenyl)(methyl)amino)-5-(3,4,5-trifluorophenyl)pyrazolo[1,5-a]pyrimidine-2-carbonyl)piperidin-4-yl)acetic acid represented by chemical formula (V)

(V)

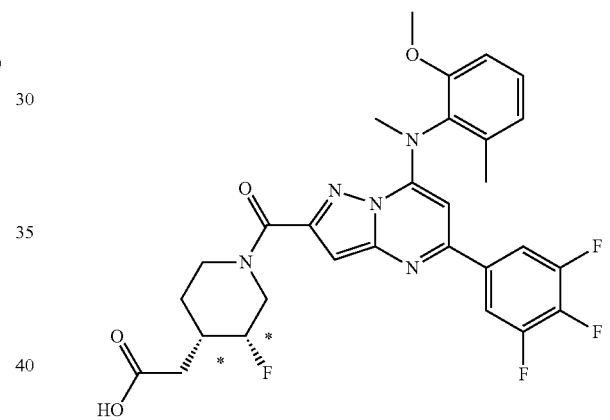

2-((3R*,4S*)-3-methoxy-1-(7-((2-methoxy-6-methylphenyl)(methyl)amino)-5-(3,4,5-trifluorophenyl)pyrazolo[1,5-a]pyrimidine-2-carbonyl)piperidin-4-yl)acetic acid represented by chemical formula (VI)

(VI)

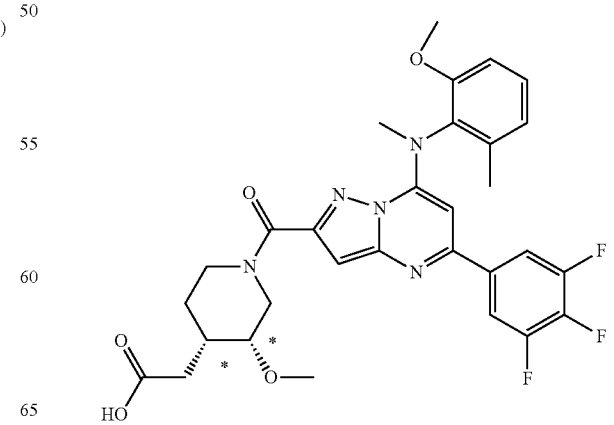

101

(R)-3-(7-((2-fluoro-6-methoxyphenyl)(methyl)amino)-N-methyl-5-(3,4,5-trifluorophenyl)pyrazolo[1,5-a]pyrimidine-2-carboxamide)butanoic acid represented by chemical formula (VII)

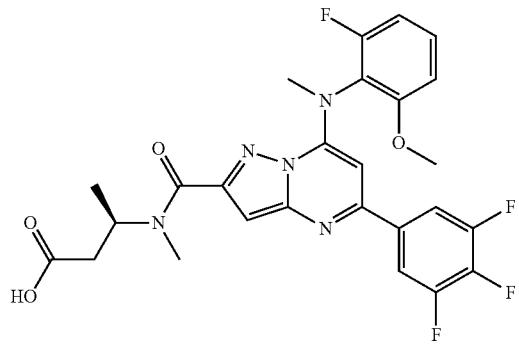

(VII)

2-((1α,5α,6α)-3-(5-(4-chloro-3,5-difluorophenyl)-7-(isobutyl((R)-3-methylbutan-2-yl)amino)pyrazolo[1,5-a]pyrimidine-2-carbonyl)-3-azabicyclo[3.1.0]hexan-6-yl)acetic acid represented by chemical formula (VIII)

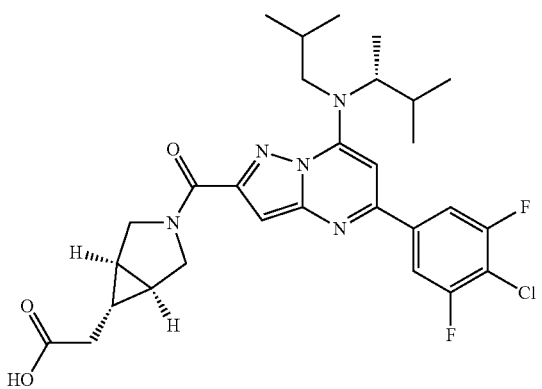

(VIII)

(R)-3-(7-(isobutyl((R)-3-methylbutan-2-yl)amino)-N-methyl-5-(3,4,5-trifluorophenyl)pyrazolo[1,5-a]pyrimidine-2-carboxamide)butanoic acid represented by chemical formula (IX)

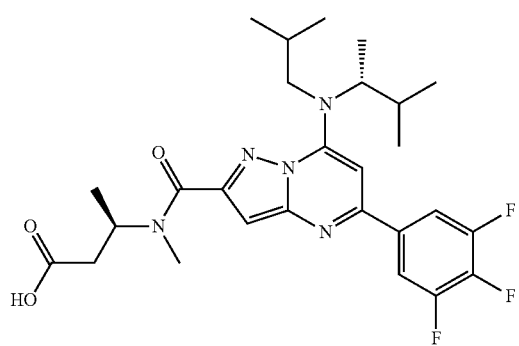

(IX)

102

2-((3R,4S)-1-(5-(4-chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid represented by chemical formula (X)

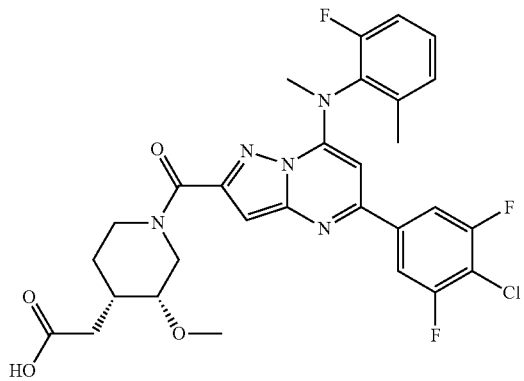

(X)

2-((3R*,4S*)-1-(5-(4-chloro-3-fluorophenyl)-7-((2-chloro-6-methylphenyl)(methyl)amino)pyrazolo[1,5-a]pyrimidine-2-carbonyl)-3-methoxypiperidin-4-yl)acetic acid represented by chemical formula (XI)

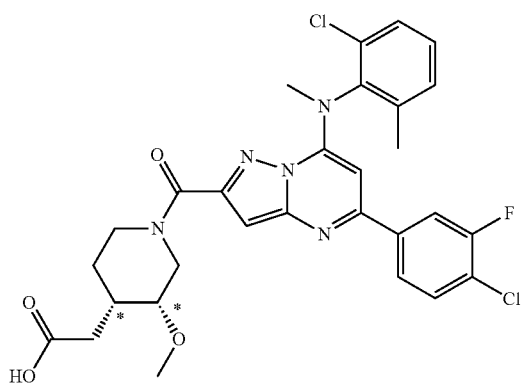

(XI)

2-((3R*,4S*)-1-(5-(4-chloro-3,5-difluorophenyl)-7-((2-chloro-6-methylphenyl)(methyl)amino)pyrazolo[1,5-a] pyrimidine-2-carbonyl)-3-methoxypiperidin-4-yl)acetic acid represented by chemical formula (XII)

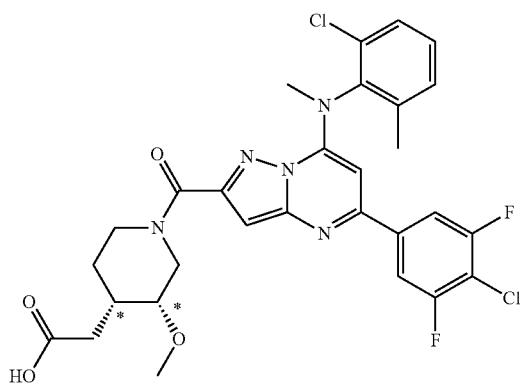

(XII)

2-((3R*,4S*)-1-(7-((2-chloro-6-fluorophenyl)(methyl)
amino)-5-(3,4,5-trifluorophenyl)pyrazolo[1,5-a]py-
rimidine-2-carbonyl)-3-fluoropiperidin-4-yl)acetic
acid represented by chemical formula (XIII)

(XIII)

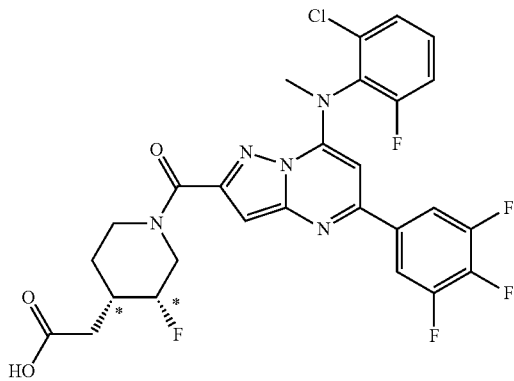

2-((3R*,4S*)-1-(5-(4-chloro-3,5-difluorophenyl)-7-((2-
chlorophenyl)(methyl)amino)pyrazolo[1,5-a]pyrimi-
dine-2-carbonyl)-3-fluoropiperidin-4-yl)acetic acid
represented by chemical formula (XIV)

(XIV)

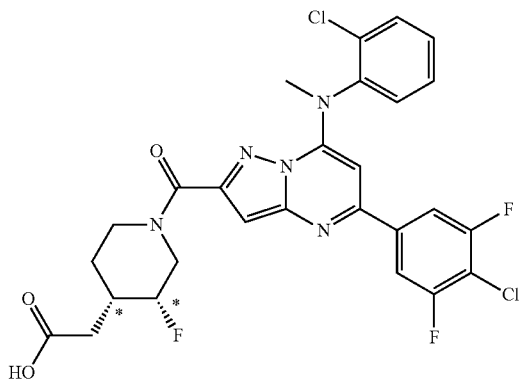

2-((1α,5α,6α)-3-(5-(4-chloro-3,5-difluorophenyl)-7-(iso-
propyl(propyl)amino)pyrazolo[1,5-a]pyrimidine-2-car-
bonyl)-3-azabicyclo[3.1.0]hexan-6-yl)acetic acid rep-
resented by chemical formula (XV)

(XV)

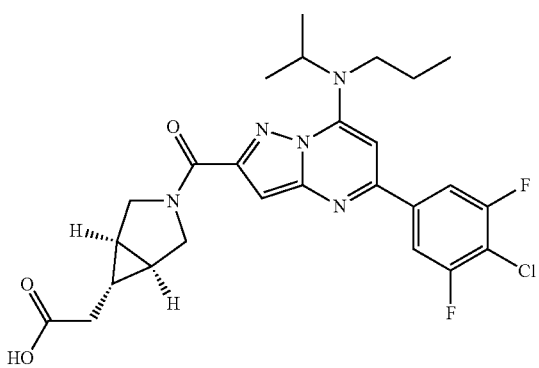

2-((1α,5α,6α)-3-(7-(isobutyl((S)-1-phenylethyl)amino)-
5-(3,4,5-trifluorophenyl)pyrazolo[1,5-a]pyrimidine-2-
carbonyl)-3-azabicyclo[3.1.0]hexan-6-yl)acetic acid
represented by chemical formula (XVI)

(XVI)

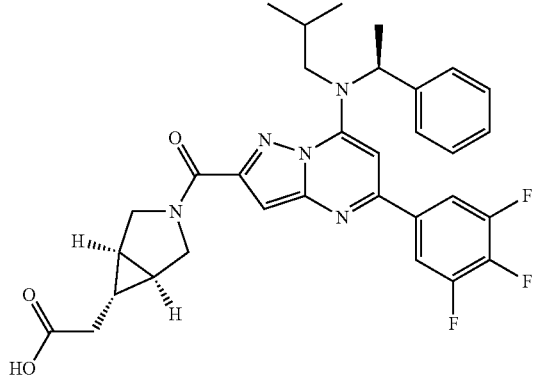

2-(1-(7-((2-chloro-6-fluorophenyl)(methyl)amino)-5-(3,
4,5-trifluorophenyl)pyrazolo[1,5-a]pyrimidine-2-car-
bonyl)piperidin-4-yl)acetic acid represented by chemi-
cal formula (XVII)

(XVII)

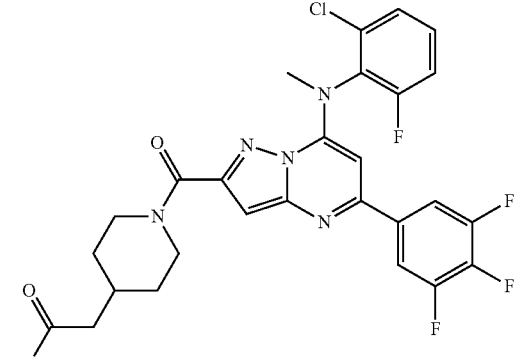

and
2-((3R*,4S*)-1-(5-(4-chloro-3,5-difluorophenyl)-7-(iso-
propyl(propyl)amino)pyrazolo[1,5-a]pyrimidine-2-car-
bonyl)-3-methylpiperidin-4-yl)acetic acid represented
by chemical formula (XVIII)

(XVIII)

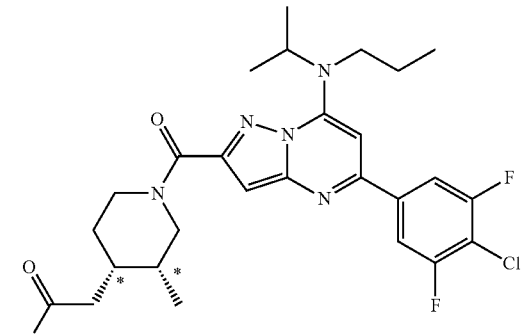

or a pharmaceutically acceptable salt thereof.

2. 2-((3R,4S)-1-(5-(4-Chloro-3,5-difluorophenyl)-7-((2-fluoro-6-methylphenyl)(methyl)amino)pyrazolo[1,5-a]pyrimidine-2-carbonyl)-3-methoxypiperidin-4-yl)acetic acid represented by chemical formula (X)

(X)

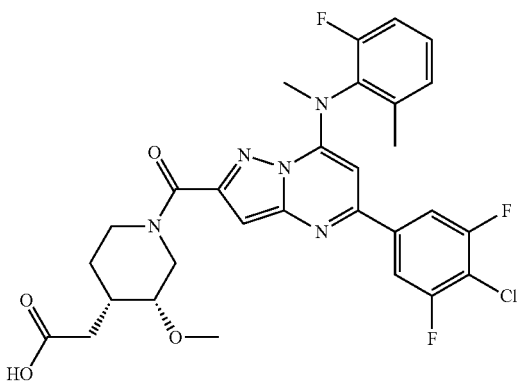

or a pharmaceutically acceptable salt thereof.

3. 2-((3R*,4S*)-3-Methoxy-1-(7-((2-methoxy-6-methylphenyl)(methyl)amino)-5-(3,4,5-trifluorophenyl)pyrazolo[1,5-a] pyrimidine-2-carbonyl)piperidin-4-yl)acetic acid represented by chemical formula (VI)

(VI)

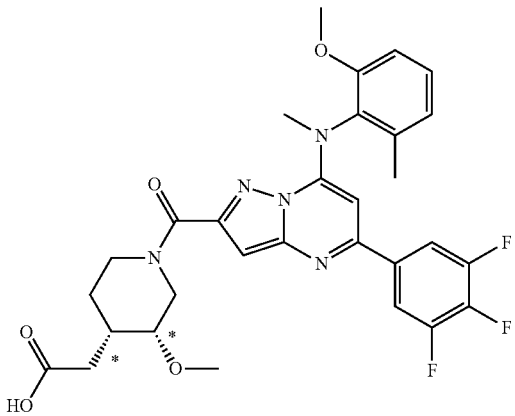

or a pharmaceutically acceptable salt thereof.

4. (R)-3-(7-((2-Fluoro-6-methoxyphenyl)(methyl)amino)-N-methyl-5-(3,4,5-trifluorophenyl)pyrazolo[1,5-a]pyrimidine-2-carboxamide)butanoic acid represented by chemical formula (VII)

(VII)

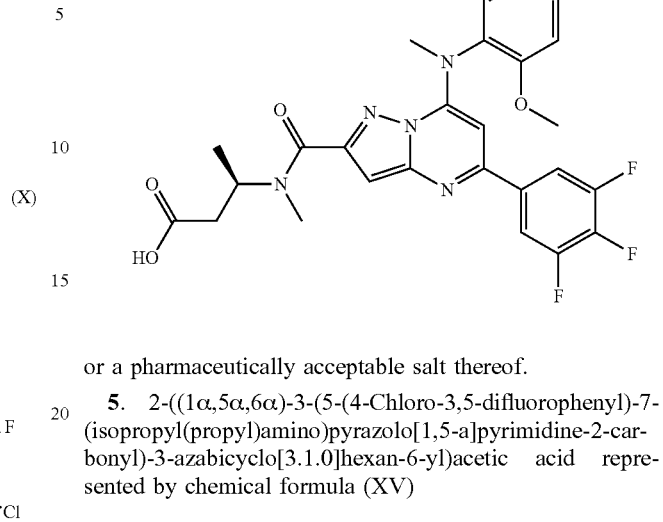

or a pharmaceutically acceptable salt thereof.

5. 2-((1α,5α,6α)-3-(5-(4-Chloro-3,5-difluorophenyl)-7-(isopropyl(propyl)amino)pyrazolo[1,5-a]pyrimidine-2-carbonyl)-3-azabicyclo[3.1.0]hexan-6-yl)acetic acid represented by chemical formula (XV)

(XV)

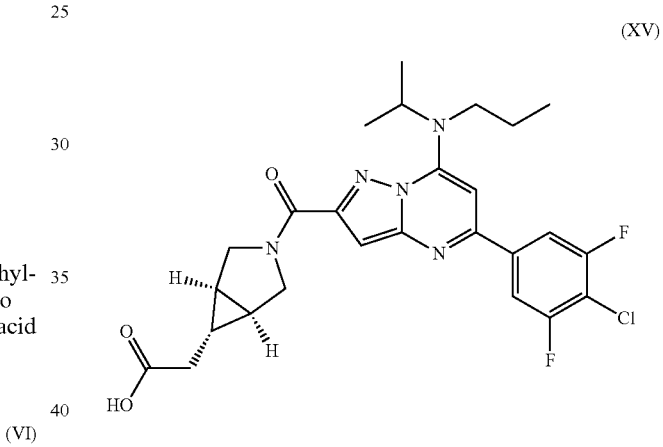

or a pharmaceutically acceptable salt thereof.

6. A pharmaceutical composition comprising the compound or pharmaceutically acceptable salt thereof according to claim 1.

7. A method for treating an inflammatory skin disease, comprising administering the compound or pharmaceutically acceptable salt thereof according to claim 1 to a patient in need thereof.

8. The method according to claim 7, wherein the inflammatory skin disease is atopic dermatitis.

9. The method according to claim 7, wherein the inflammatory skin disease is contact dermatitis.

10. The method according to claim 7, wherein the inflammatory skin disease is skin eczema.

11. The method according to claim 7, wherein the inflammatory skin disease is psoriasis.

12. The method according to claim 7, wherein the inflammatory skin disease is dry skin dermatitis.

13. A method for treating an inflammatory bowel disease, comprising administering the compound or pharmaceutically acceptable salt thereof according to claim 1 to a patient in need thereof.

14. The method according to claim 13, wherein the inflammatory bowel disease is ulcerative colitis.

15. The method according to claim 13, wherein the inflammatory bowel disease is Crohn's disease.

16. The method according to claim 13, wherein the inflammatory bowel disease is infectious enteritis.

\* \* \* \* \*

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: PAR2 agonist

<400> SEQUENCE: 1

Val Lys Gly Ile Leu Ser
1               5

<210> SEQ ID NO 2
<211> LENGTH: 6
<212> TYPE: PRT
<213> ORGANISM: Artificial Sequence
<220> FEATURE:
<223> OTHER INFORMATION: PAR2 agonist

<400> SEQUENCE: 2

Leu Arg Gly Ile Leu Ser
1               5
```